(12) United States Patent
Behzadi et al.

(10) Patent No.: US 11,458,021 B2
(45) Date of Patent: Oct. 4, 2022

(54) ANISOTROPIC MATERIALS IN MEDICAL DEVICES

(71) Applicant: Kambiz Behzadi, Pleasanton, CA (US)

(72) Inventors: Kambiz Behzadi, Pleasanton, CA (US); Michael E. Woods, Brisbane, CA (US)

(73) Assignee: Kambiz Behzadi, Pleasanton, CA (US)

( * ) Notice: Subject to any disclaimer, the term of this patent is extended or adjusted under 35 U.S.C. 154(b) by 423 days.

(21) Appl. No.: 16/693,214

(22) Filed: Nov. 22, 2019

(65) Prior Publication Data

US 2020/0205988 A1 Jul. 2, 2020

Related U.S. Application Data

(60) Continuation-in-part of application No. 16/588,991, filed on Sep. 30, 2019, which is a continuation-in-part
(Continued)

(51) Int. Cl.
*A61F 2/34* (2006.01)
*A61B 17/60* (2006.01)
(Continued)

(52) U.S. Cl.
CPC .............. *A61F 2/34* (2013.01); *A61B 17/60* (2013.01); *A61B 17/7283* (2013.01); *A61F 2/28* (2013.01); *A61F 2/30771* (2013.01); *A61B 17/66* (2013.01); *A61B 34/10* (2016.02); *A61B 2017/00526* (2013.01); *A61B 2017/00862* (2013.01); *A61B 2017/00964* (2013.01); *A61B 2017/564* (2013.01); *A61B 2034/105* (2016.02); *A61F 2/3094* (2013.01); *A61F 2/4609* (2013.01); *A61F 2002/2825* (2013.01); *A61F 2002/30224* (2013.01); *A61F 2002/30688* (2013.01); *A61F 2002/30881* (2013.01); *A61F 2002/30891* (2013.01); *A61F 2002/30985* (2013.01); *A61F 2002/4627* (2013.01); *A61F 2002/4681* (2013.01)

(58) Field of Classification Search
CPC ...... A61F 2/30; A61F 2/28; A61F 2/34; A61F 2/38
See application file for complete search history.

(56) References Cited

U.S. PATENT DOCUMENTS

| 4,608,053 A | 8/1986 | Keller |
| 5,358,532 A | 10/1994 | Evans et al. |

(Continued)

FOREIGN PATENT DOCUMENTS

| WO | 2007096476 | 8/2007 |
| WO | 2007096476 A2 | 8/2007 |

OTHER PUBLICATIONS

PCT International Search Report for International application No. PCT/US17/26417, dated Jul. 3, 2017.
(Continued)

*Primary Examiner* — Jason-Dennis N Stewart
(74) *Attorney, Agent, or Firm* — Patent Law Offices Of Michael E. Woods; Michael Woods

(57) ABSTRACT

A system and method for improving upon an ability of a surgeon to repair traumatic bone injury using new materials, components, and structures. A structure may be used as an implant or a component of an external fixator for a fractured long bone with that structure having anisotropic and viscoelastic properties, such as through additive manufacturing techniques.

18 Claims, 41 Drawing Sheets

Related U.S. Application Data of application No. 16/588,416, filed on Sep. 30, 2019, which is a continuation-in-part of application No. 16/532,448, filed on Aug. 5, 2019, now abandoned, application No. 16/693,214, which is a continuation-in-part of application No. 16/271,860, filed on Feb. 10, 2019, now abandoned, and a continuation-in-part of application No. 16/267,345, filed on Feb. 4, 2019, which is a continuation-in-part of application No. 16/258,635, filed on Jan. 27, 2019, now abandoned, said application No. 16/532,448 is a division of application No. 15/592,233, filed on May 11, 2017, now abandoned, said application No. 16/258,635 is a division of application No. 15/458,586, filed on Mar. 14, 2017, now Pat. No. 10,299,930, said application No. 15/592,233 is a continuation-in-part of application No. 15/406,752, filed on Jan. 15, 2017, now abandoned, which is a continuation-in-part of application No. 15/234,927, filed on Aug. 11, 2016, now Pat. No. 10,864,083, said application No. 16/271,860 is a continuation-in-part of application No. 15/234,927, filed on Aug. 11, 2016, now Pat. No. 10,864,083.

(60) Provisional application No. 62/348,987, filed on Jun. 12, 2016, provisional application No. 62/319,377, filed on Apr. 7, 2016.

(51) Int. Cl.
*A61F 2/30* (2006.01)
*A61F 2/28* (2006.01)
*A61B 17/72* (2006.01)
*A61F 2/46* (2006.01)
*A61B 34/10* (2016.01)
*A61B 17/56* (2006.01)
*A61B 17/00* (2006.01)
*A61B 17/66* (2006.01)

(56) References Cited

U.S. PATENT DOCUMENTS

| | | | |
|---|---|---|---|
| 5,702,473 A | 12/1997 | Albrektsson et al. | |
| 5,713,901 A | 2/1998 | Tock | |
| 6,048,365 A | 4/2000 | Burrows et al. | |
| 6,197,062 B1 | 3/2001 | Fenlin | |
| 6,231,612 B1 | 5/2001 | Balay et al. | |
| 7,875,083 B2 | 1/2011 | Sudmann | |
| 10,299,930 B2 | 5/2019 | Behzadi | |
| 2005/0004680 A1 | 1/2005 | Saladino et al. | |
| 2005/0015154 A1 | 1/2005 | Lindsey et al. | |
| 2007/0219641 A1 | 9/2007 | Dorr et al. | |
| 2008/0091271 A1 | 4/2008 | Bonitati et al. | |
| 2008/0234833 A1 | 9/2008 | Bandoh et al. | |
| 2008/0255560 A1 | 10/2008 | Myers et al. | |
| 2013/0211535 A1 | 8/2013 | Cueille | |
| 2014/0012391 A1 | 1/2014 | Gugler et al. | |
| 2014/0058526 A1 | 2/2014 | Meridew et al. | |
| 2014/0128986 A1 | 5/2014 | Podolsky | |
| 2014/0303743 A1 | 10/2014 | Choudhury et al. | |
| 2014/0363481 A1 | 12/2014 | Pasini et al. | |
| 2014/0370462 A1 | 12/2014 | Porter et al. | |
| 2014/0371897 A1 | 12/2014 | Lin et al. | |
| 2015/0216668 A1 | 8/2015 | Smith | |
| 2017/0290666 A1 | 10/2017 | Behzadi | |
| 2017/0290667 A1 | 10/2017 | Behzadi | |
| 2017/0340448 A1 | 11/2017 | Behzadi | |
| 2017/0354505 A1 | 12/2017 | Behzadi | |

OTHER PUBLICATIONS

PCT Written Opinion of The International Searching Authority for International application No. PCT/US17/26417 dated Jul. 3, 2017.
International Search Report regarding International application No. PCT/US2017/037042 dated Oct. 6, 2017.
Written Opinion of the International Searching Authority regarding International application No. PCT/US2017/037042 dated Oct. 6, 2017.
U.S. Appl. No. 16/267,345, filed Feb. 4, 2019, Kambiz Behzadi.
U.S. Appl. No. 16/267,813, filed Feb. 5, 2019, Kambiz Behzadi.
U.S. Appl. No. 16/532,448, filed Aug. 5, 2019, Kambiz Behzadi.
U.S. Appl. No. 16/588,416, filed Sep. 30, 2019, Kambiz Behzadi.
U.S. Appl. No. 16/588,991, filed Sep. 30, 2019, Kambiz Behzadi et al.
U.S. Appl. No. 62/319,377, filed Apr. 7, 2016, Kambiz Behzadi.
U.S. Appl. No. 62/348,987, filed Jun. 12, 2016, Kambiz Behzadi.
U.S. Appl. No. 15/234,927, filed Aug. 11, 2016, Kambiz Behzadi.
U.S. Appl. No. 15/406,752, filed Jan. 15, 2017, Kambiz Behzadi.
U.S. Appl. No. 15/458,586, filed Mar. 14, 2017, Kambiz Behzadi.
U.S. Appl. No. 15/592,233, filed May 11, 2017, Kambiz Behzadi.
U.S. Appl. No. 16/032,867, filed Jul. 11, 2018, Kambiz Behzadi.
U.S. Appl. No. 16/258,635, filed Jan. 27, 2019, Kambiz Behzadi.
U.S. Appl. No. 16/271,860, filed Feb. 10, 2019, Kambiz Behzadi.
U.S. Appl. No. 16/842,470, filed Apr. 7, 2020, Kambiz Behzadi et al.

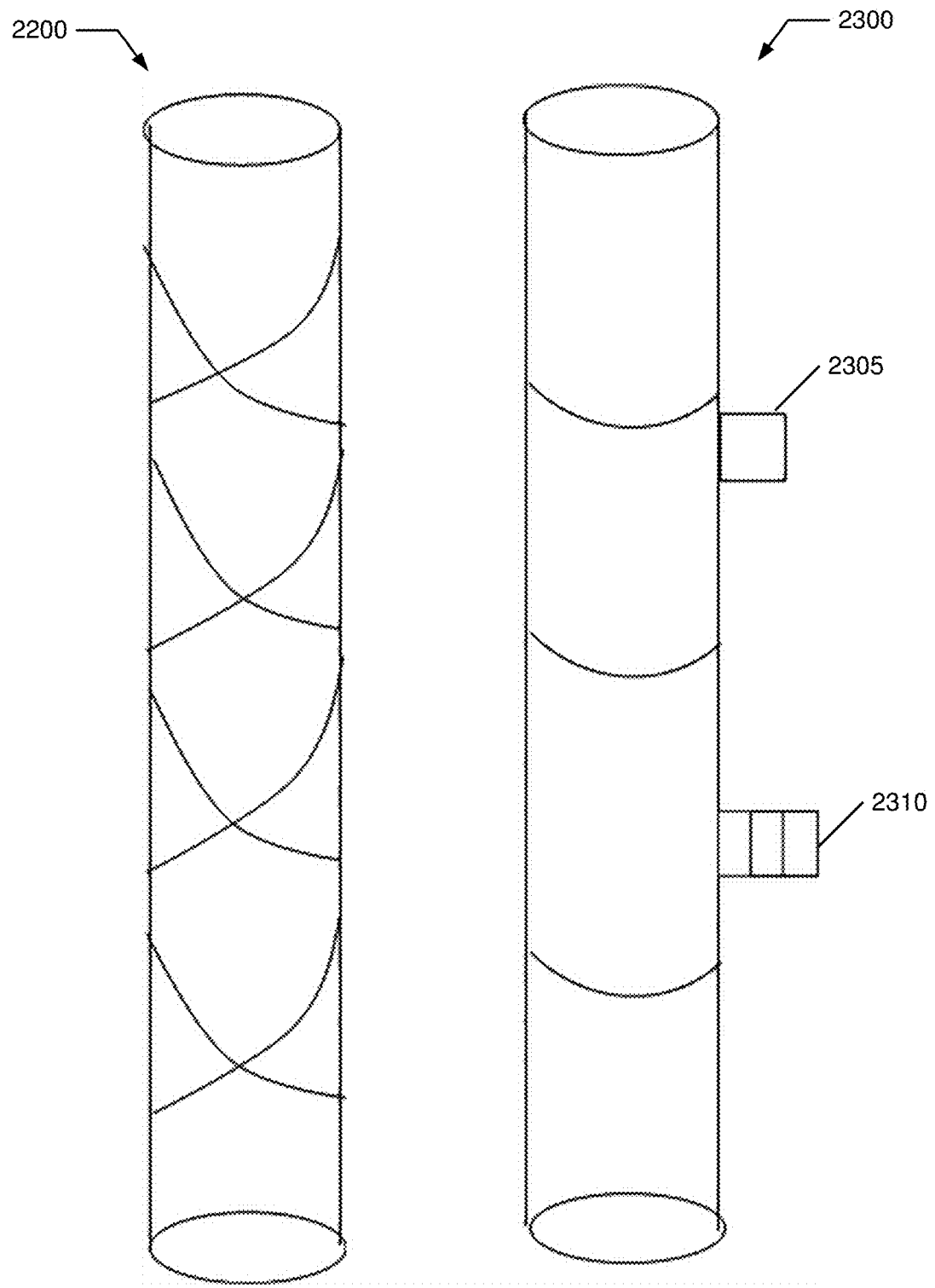
FIG. 22  FIG. 23

ANISOTROPIC MATERIALS IN MEDICAL DEVICES

CROSS REFERENCE TO RELATED APPLICATIONS

This Application is a Continuation-in-part of application Ser. No. 16/588,991 filed on Sep. 30, 2019; application Ser. No. 16/588,991 is a Continuation-in-part of application Ser. No. 16/588,416 filed on Sep. 30, 2019; application Ser. No. 16/588,416 is a Continuation-in-part of application Ser. No. 16/532,448 filed on Aug. 5, 2019; application Ser. No. 16/532,448 is a Division of application Ser. No. 15/592,233 filed on May 11, 2017; application Ser. No. 15/592,233 is a Continuation-in-part of application Ser. No. 15/406,752 filed on Jan. 15, 2017; application Ser. No. 15/406,752 is a Continuation-in-part of application Ser. No. 15/234,927 filed on Aug. 11, 2016; application Ser. No. 15/234,927 claims the benefit of U.S. Provisional Application 62/319,377 filed on Apr. 7, 2016; This Application is a Continuation-in-part of application Ser. No. 16/271,860 filed on Feb. 10, 2019; application Ser. No. 16/271,860 is a Continuation-in-part of application Ser. No. 15/234,927 filed on Aug. 11, 2016; This Application is a Continuation-in-part of application Ser. No. 16/267,345 filed on Feb. 4, 2019; application Ser. No. 16/267,345 is a Continuation-in-part of application Ser. No. 16/258,635 filed on Jan. 27, 2019; application Ser. No. 16/258,635 is a Division of application Ser. No. 15/458,586 filed on Mar. 14, 2017; application Ser. No. 15/458,586 claims the benefit of U.S. Provisional Application 62/348,987 filed on Jun. 12, 2016; and all the contents of which are all hereby expressly incorporated in their entireties by reference thereto for all purposes.

FIELD OF THE INVENTION

The present invention relates generally to medical devices and assemblies, including mechanical assembly and assemblies for bone fracture repair, and more specifically, but not exclusively, to a reducing and fixating a bone fracture using adjustable/variable anisotropic components having a set of tuned/tunable stiffness elements, and including, generally, mechanical assemblies installed into living tissue, and more specifically, but not exclusively, to improvements in prostheses and prosthetic assemblies installed into bone tissue and medical implants and implant assemblies installed into a body.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

The incorporated patents and applications often address a problem of applied forces in the assembly and installation of mechanical systems, such as a prosthesis used in orthopedic surgery.

There are many considerations regarding the use of applied impact forces in orthopedic surgery and in particular the use of a hammer or a mallet to apply an impact force. Much work has been done to help understand, control, modulate, and replace the impaction forces created by the surgeon's mallet. Some of the incorporated references have described various components of these applied forces, often using orthopedics as an example though the invention is not required to be so limited. The use of a mallet in orthopedics creates a momentum or an impulse and effects of the impulse in creating an impaction force can be broken down into its components, including magnitude, frequency and dwell time. Some of the incorporated references include systems and methods of substituting an installation force for the impaction force in orthopedic surgery. Embodiments of the incorporated references may allow the surgeon to perform some of these surgeries in a safer and more controlled fashion by rethinking conventional procedures related to a prosthesis. Further, some of the incorporated references relate to assembly of a prosthesis for use in an orthopedic procedure.

The collection of incorporated references includes multiple embodiments of multiple inventions, with some of these embodiments including a use of vibratory force/energy that disclosed as important for addressing problems with application of impaction forces.

In some of the embodiments of the incorporated patents and applications, there is a discussion that there may be significant advantage to use of controlled installation forces communicated to a prosthesis or prosthesis component at higher (including ultrasonic) frequencies. Some or a significant portion of these advantages may relate to differences between kinetic and static coefficients of friction, and/or vibratory modes of the installation site (bone) or mating component for a prosthetic assembly, among other possible explanations. These features may allow a prosthesis (or portion thereof) vibrating at an appropriate mode to diminish, sometimes significantly, forces resisting installation or assembly, respectively. With these diminished forces, the surgeon may be able to employ decreased installation forces which allow easier and safer insertions. In some embodiments, the embodiment may allow for a concurrent ability to align the prosthesis during/after installation as part of the same procedure with the same tools. This is in contrast to conventional systems which employ one set of tools for insertion and then another set of tools after insertion to correction malpositioning. Some embodiments of the present invention may allow for concurrent insertion and desired positioning.

Current surface treatment of a prosthesis is designed for porous metal ingrowth bonding of a prosthesis to bone (in contrast to a use of cement to bond a prosthesis to bone). In general the porous implants are typically created as "composite structures" consisting of a substrate typically made of either cobalt chrome or titanium alloy (which carries the patient's weight), and a porous surface which is designed to enhance osseointegration of the implant (referred to as "porous coating"). The porous coating includes microstructural features such as peaks, valleys and deep caves. This mimics the structure of trabecular/cancellous bone with its three-dimensional and interconnecting network of pores and capillary properties. The porous coating aids in initial scratch fixation as well as long term fixation through osseointegration of bone with the surface of the bone. Recently, there have been many advances in the creation of the porous coating that more accurately resemble the trabecular bone. These techniques all involve multiple steps in the creation of the porous coating surface and subsequent bonding of this surface to the alloy substrate. Today, the majority of porous coatings are made of titanium or tantalum. These porous coatings are textured with desirable mechanical properties closer to bone and with desirable porosity. They are created separately and applied to the actual implant (as a composite structure) via variety of bonding methods including plasma spray, chemical etching thin films and plates, chemical and/or physical vapor disposition, sintering, brazing, diffusion bonding, gluing or cementing, and the like). Thus, the porous coating that is seen on the surface of a typical conventional prosthesis is: i) a composite structure that must to be added to the substrate, and ii) a randomized pattern with no preferential orientation and or design.

Fixation of hip and knee replacement implants to bone is critical to the success of the procedure. A variety of roughened surfaces and three-dimensional (3-D) porous surfaces have been used to enhance biological fixation on orthopedic implants for over 30 years. More recently, highly porous metals have emerged as versatile biomaterials that may enhance fixation to bone and are suitable to a number of applications in hip and knee replacement surgery. The advantages provided by these newly developed porous metals may improve cementless fixation and long-term patient outcomes in hip and knee replacement.

Thermal spray technologies involving the melting and subsequent spraying of metal feedstock have been leveraged by various implant manufacturers to apply highly roughened commercially pure titanium (CPTi) and titanium (Ti) alloy coatings onto implants used in hip and knee arthroplasty. These include wire arc deposition, plasma spray, sintering porous beads, diffusion bonding of titanium coatings, advanced highly porous coating technologies using tantalum and titanium, among other procedures.

Current installation procedures for some prosthesis, such as for an acetabular cup, include attachment of a rod axially aligned with a longitudinal axis of the prosthesis that is used to apply the impacting forces and impact the prosthesis into the bone to the desired depth.

Repair to traumatic bone injury is complex and each repair modality may offer various advantages and disadvantages.

Historically, early hip replacement consisted of a non-modular femoral head with a single neck option, the so-called "monobloc". This meant that restoring the leg length and offset was difficult and may have resulted in instability and abductor dysfunction. As a result, modularity was introduced into the design of hip prosthesis and has become increasingly common in the last two decades. Modularity can be exhibited at the junction between the head and the neck, and at the junction between the trunnion (neck) and the body. The neck head junction typically consists of a trunnion, which has a machined taper allowing for an interference fit. The taper interface is where the femoral head (female taper surface) attaches to the trunnion (male taper) of the femoral stem. This optionality is extremely attractive to the surgeon allowing the ability to more accurately restore leg length, offset, and produce good stability independent of femoral stem fixation. Taper corrosion however, has recently become a clinical issue.

Trunnionosis is defined as wear of the femoral head-neck interface and has been acknowledged as a source of total hip arthroplasty (THA) failure. This phenomenon appears to have gained prevalence with newer THA implant designs, particularly when modularity was introduced.

Modularity allows for better intraoperative restoration of leg length and control of hip offset, but while this enables a more customized fit for the patient, it may have untoward effects. This modularity at times may play a role in increased wear and mechanical insufficiency at the trunnion, ultimately leading to revision. By some estimates, trunnionosis accounts for up to 3% of all revision procedures. The exact cause of trunnionosis, which is likely multifactorial, currently remains poorly understood. It is postulated that contributing factors include wear between metal on metal modular junctions, corrosion and fretting damage, and release of metal ions from affected components. Additionally, different implant designs and geometries have demonstrated a predisposition to trunnion failure. Although the exact cause of the recent increase of corrosion related complications is unknown, some have hypothesized that having differing alloys at the modular junction, which are under high loads, may lead to increased corrosion and fretting, i.e.: use of cobalt chrome femoral head (CoCr) on Titanium trunnion.

It may be advantageous for a system and method to improve upon an ability of a surgeon to repair traumatic bone injury using new materials, components, and structures.

BRIEF SUMMARY OF THE INVENTION

Disclosed is a system and method for improving upon an ability of a surgeon to repair traumatic bone injury using new materials, components, and structures and/or improving mechanical assemblies, such as prosthetic implants, intended to be installed in living tissue such as bone.

The following summary of the invention is provided to facilitate an understanding of some of the technical features related to surface treatment for mating/contacting surfaces of a prosthesis or a prosthesis component, and/or technical features related to prosthesis manufacture and assembly, and is not intended to be a full description of the present invention. A full appreciation of the various aspects of the invention can be gained by taking the entire specification, claims, drawings, and abstract as a whole. The present invention is applicable to other prosthesis devices in addition to acetabular cups, to other mechanical systems for reduced force insertion of one structure into another, and to other configurations and arrangements of exterior surface structures than those presented or described herein. Embodiments of the invention may include materials used in a structure that may be used as an implant or a component of an external fixator for a fractured long bone with that structure having anisotropic and viscoelastic properties, such as through additive manufacturing techniques.

In an embodiment of the present invention, an implant may include a surface treatment for aiding operations with the implant. For example, some surface treatments provide an asymmetry in installation versus removal to bias the associated implant deeper into an installation site.

An embodiment of the present invention includes a surface treatment, whether produced as an innate outer surface feature of the device during manufacture or added to a surface (e.g., an outer surface) of a device, such as, for example, a retrofit solution. The surface treatment provides an asymmetric relative force for the device in cooperation with material of an installation side (e.g., easier to push the prosthesis into a bone than to extract the prosthesis from the bone). For example, the treatment includes provision of various exterior structures that interact with material of the installation site more strongly in one relative direction (e.g., removal or disassembly from the installation site) than in another direction (e.g., insertion or assembly into the installation site). For example, the surface treatment of the prosthesis collectively offers less resistance to installation than removal.

An embodiment of the present invention may implement two-dimensional asymmetric biasing such as described with insertion of a prosthesis into an undersized cavity for Intra-medullary nails (IM) nails or rods used for fixation of long bones in traumatic situations, including femur, tibia and humerus as well as radius and ulna.

An embodiment of the present invention may provide for both asymmetric relative forces while also including enough randomization for porous ingrowth of bone for post-installation bonding enhancement. The surface treatment and/or the ingrowth structures may be microscopic and/or macroscopic.

An embodiment of the present invention may include exterior surface structures and configurations that provide an acute angle relative to an insertion path. For example, when installing an acetabular cup into a prepared installation site of an acetabulum, the cup follows a path as it is inserted into the desired location and depth. Exterior surface portions of the cup are in contact with, and move past, the bone of the walls of the installation site. For one type of surface treatment, exterior surface structures of the surface treatment could be angled relative to the walls. The angles could be angled acutely forward (e.g., towards a bottom of the installation site) which may increase installation forces and decrease removal forces, angled perpendicularly which may be neutral as to directionally, and/or angled backward (e.g., away from the bottom of the installation site) which may increase removal forces and decrease installation forces. The magnitude, and differences, of these asymmetric forces may be influenced by many different factors including materials of the exterior surface elements and complementary material of the contacting surfaces of the installation site, characteristic size and arrangement of the exterior surface elements, design goals, and/or intended use.

An embodiment of the present invention may include exterior surface structures and configurations that provide pitched structures, relative to an insertion path, that vary over the surface that provide for asymmetric relative installation forces.

An embodiment of the present invention may include a specially configured exterior surface to present a two-dimensional or a three-dimensional variable stiffness that is more conducive for transmission of force and energy longitudinally (e.g., parallel to the insertion path) and less conducive to circumferential transmission (e.g., perpendicular to the insertion path). That is, there is an asymmetry of the structural response of the surface treatment to make it easier to move along the path while retaining the circumferential integrity for being held in place once installed.

An embodiment of the present invention may include use of additive manufacturing techniques to produce a final prosthesis having an integrated surface treatment that may not require a multi-step process of applying a porous surface treatment to an underlying prosthetic foundation.

An embodiment of the present invention may include use of subtractive manufacturing techniques to produce a final prosthesis having an integrated surface treatment that may not require a multi-step process of applying a porous surface treatment to an underlying prosthetic foundation.

An embodiment of the present invention may include a different installation adaptor for applying forces used to locate a prosthesis within a bone. The conventional method of using an apex-attached rod to apply the forces may be thought of as "pulling" the prosthesis through the installation site. In contrast, an embodiment may include an attachment modality or adaptor that operates on the perimeter and/or inside surfaces to push the prosthesis through the bone. These embodiments may implicate other embodiments regarding 2D/3D wall configuration for interacting the prosthesis with the installation site.

An embodiment of the present invention may be adapted for impact installation and is not limited to other non-impactful installation procedures which may reduce a magnitude of the impact force needed and which may reduce risks of shattering bone at the installation site.

An embodiment of the present invention may include a cream, paste, gel, or other substance that may be applied to contacting surfaces of a prosthesis to be forced into an installation site. This surface treatment may function similar to a lubricant or "shaving cream" to allow to contacting surfaces to more easily move past each other and reduce a magnitude of forces used for an installation. This surface treatment may be combined with other disclosed embodiments and may be dynamically applied as the prosthesis is about to be installed at the installation site.

An embodiment of the present invention may include use of the disclosed embodiments and implementations for assembling a prosthesis (inserting one component of a modular prosthesis into a mating receptacle of another component of the modular prosthesis).

An embodiment of the present invention may include a method for producing a prosthesis for installation into a medullary cavity of a bone, the cavity providing a resistive force for installation, including a) manufacturing additively an elongate structure for the prosthesis, the elongate structure including a foundation and a surface; and b) during the manufacturing step a) establishing one or more portions of the structure with a bias for installation; wherein a first portion of the one or more portions includes a first region of the foundation, wherein a second portion of the one or more portions includes a second region of the foundation, and wherein the first portion and the second portion are cooperatively configured to produce a two-dimensional asymmetric stiffness implementing the bias for insertion into the medullary cavity.

An embodiment of the present invention may include an implant for insertion into a medullary cavity of a bone, the cavity providing a resistive force for installation, including an elongate structure including a proximal end, a distal end spaced apart from the proximal end, a longitudinal axis extending between the ends, and a portion having a foundational bias for installation into the cavity; and a first set of regions of the elongate structure and a second set of regions of the elongate structure; wherein the regions are cooperatively configured to produce a two-dimensional asymmetric stiffness implementing the foundational bias for insertion into the medullary cavity.

An embodiment of the present invention may include a method for repairing a fracture of a long bone, including a) producing a template of the long bone; b) reducing the fracture using said template to produce a reduced fractured long bone; and c) fixing said reduced fractured long bone using an exterior structure spanning a length of the fracture wherein said exterior structure includes an anisotropic and viscoelastic component.

An embodiment of the present invention may include an external fixator for a set of fractures in a long bone, including a spanning structure having a length spanning the set of fractures, said spanning structure including a rigid component including an anisotropic and viscoelastic material; and a set of couplers fixing said spanning structure to the long bone.

An embodiment of the present invention may include a bone implant, including an elongate core; and a set of concentric layers disposed around said core; wherein said elongate core and each layer of said set of concentric layers have varying moduli of elasticity.

An embodiment of the present invention may include a method for repairing a fracture of a long bone using a template of the long bone, including a) reducing the fracture using the template to produce a reduced fractured long bone; and b) fixing the reduced fractured long bone using an exterior structure spanning a length of the fracture wherein the exterior structure includes a first anisotropic component having a first stiffness profile; and c) replacing the first anisotropic component, after a period of healing of the long bone with the first anisotropic component, with a second anisotropic component having a second stiffness profile, the second stiffness profile different from the first stiffness profile.

An embodiment of the present invention may include an external fixator for a set of fractures in a long bone, including a spanning structure having a length spanning the set of fractures, the spanning structure compatible with a set of two or more rigid components, each the rigid component including an anisotropic component having a distinct stiffness profile, distinct within the set of two or more rigid components; and a set of couplers fixing the spanning structure to the long bone; wherein the spanning structure includes a rigid component engagement system configured to allow substitution of a first one rigid component of the set of rigid components with a second one rigid component of the set of rigid components while the spanning structure is coupled to the long bone.

An embodiment of the present invention may include a method of varying, over time and the course of fracture healing, the material properties of metallic and composite rods used as spanning devices for fixation of long bone fractures.

An embodiment of the present invention may include a method of varying, over time and course of fracture healing, the stiffness properties of metallic and composite rods used as spanning devices for fixation of long bone fractures.

An embodiment of the present invention may include a method for utilizing programmable smart composites to allow sensing of stress, strain, impact, acceleration, vibration and subsequent computation and communication through an actuation response within the composite to allow progressively more load sharing responsibilities by the long bone fracture over time.

An embodiment of the present invention may include a method to allow autonomous preprogrammed load sharing, over a defined period of time, between a spanning composite smart "robotic material rod" used for fracture fixation, and a healing long bone fracture.

An embodiment of the present invention may include a method of allowing the healing fractured long bone to be exposed to a variety and different combinations of types of stress including compression, shear, torsion, bending and tension, over various periods of time within the healing timeline.

An embodiment of the present invention may include a method of producing anisotropic rods for use in external fixation of long bones.

An embodiment of the present invention may include a method of producing "robotic material rods" for use in external fixation of long bones.

An embodiment of the present invention may include a method of rod exchange in clinic to allow increasing exposure to stress of a healing long bone.

An embodiment of the present invention may include a method of rapid fracture stabilization that minimizes blood loss, surgical dissection and maximizes healing potential of bone.

An embodiment of the present invention may include a method of fracture stabilization that allows manipulation of stresses (forces) experienced by the healing bone to promote either enchondral bone formation over intramembranous (primary) bone formation and vice versa.

An embodiment of the present invention may include a method of fracture stabilization with an external fixator that allows direct addition of subsonic or ultrasonic vibration to the external fixator apparatus to allow enhanced bone healing.

A method for repairing a fracture of a bone using a template of the bone, including a) reducing the fracture using the template to produce a reduced fractured bone; and b) fixing the reduced fractured bone using a structure spanning a length of the fracture wherein the structure includes an anisotropic component having a variable stiffness profile, the anisotropic component including a set of non-biodegradable/non-bioabsorbable stiffness elements, and the anisotropic component including a set of biodegradable/bioabsorbable stiffness elements with the variable stiffness profile changing in a predetermined manner responsive to a degradation/absorbtion of the set of degradable/absorbable stiffness elements; and c) degrading/absorbing selectively, in situ, the set of degradable/absorbable stiffness elements during healing of the fracture without a stiffness-affecting degradation/absorption of the set of non-biodegradable/non-bioabsorbable stiffness elements, while the structure spans the length of the fracture.

A method for repairing a fracture of a bone using a template of the bone, including a) reducing the fracture using the template to produce a reduced fractured bone; and b) fixing the reduced fractured bone using a structure spanning a length of the fracture wherein the structure includes an anisotropic component having a variable stiffness profile, the anisotropic component including a set of robotic materials with the variable stiffness profile changing in a predetermined manner responsive to a stiffness reconfiguration by the set of robotic materials; and c) adjusting, in situ, the stiffness profile using the set of robotic materials during healing of the fracture, while the structure spans the length of the fracture.

A fixator for a set of fractures in a bone, including a spanning structure having a length spanning the set of fractures, the spanning structure including an anisotropic component having a variable stiffness profile responsive to a selective degradation of a set of degradable/absorbable stiffness structures while not degrading/absorbing non-degradable/nonabsorbable stiffness structures; and an applicator, coupled to the spanning structure, configured to position and apply the spanning structure to the bone after a reduction of the set of fractures.

Any embodiment of the present invention may be superior through manipulation of the friction between contacting surfaces of the prosthesis relative to the material of the installation site. The BMD3 vibratory mechanism may contribute to shifting some or all of the frictional forces from a static coefficient of friction regime to a kinetic coefficient of friction regime. Other factors may also be contributing to a reduction in installation forces required. Similarly, some of the effects of the surface treatment and/or surface application may implicate, at least partially, a transformation of some or all of the resistive forces into the kinetic coefficient of friction regime.

Some embodiments of the present invention may include a system and method for improving mechanical assemblies, such as prosthetic implants, intended to be installed in living tissue such as bone. Force-imparting devices are adapted and may include angularity, which may be introduced with specialized additive manufacturing, which may impart congruent cross-sections while providing variable stiffness. In some cases, the variable stiffness may be "stretchy" in a longitudinal direction and "rigid" in a radial directional which may provide an assembly bias. Additive manufacturing may allow the material of a prosthesis to be varied (e.g., density/porosity) to create variable stiffness over a length.

Some embodiments of the present invention may include one or more of: a) an implementation of a force imparting machine that delivers standardized force impulses (e.g., magnitude and frequency) at a precise direction (co-axial); b) an implementation of a design for a trunnion head and trunnion stem interface, with the introduction of angularity (sharp angles) and hence "early guidance system" protecting against macro and (subsequently) micro mis-alignment; c) an implementation of a trunnion through a different manufacturing technique (e.g., additive manufacturing possibly including "3D printing" or preform) rather than subtractive techniques; d) an implementation of multidimensional differential stiffness of a trunnion that more closely resembles one or more mechanical properties of the replaced tissue (e.g., a human femoral neck that may be stiffer on a load bearing medial neck and more elastic on a tensile lateral side; e) an implementation of a femoral head that can be made with two-dimensional differential stiffness (e.g., cross-helical arrangement in the eel's skin) or (longitudinal struts that are more flexible and horizontal bands that are more rigid) in order to allow undulatory motion and a preference for insertion; and f) an implementation of a controlled stiffness of implants, such as by changing a modulus of elasticity of the prosthesis material (e.g., metal) by controlling a density and a porosity of the crystalline metal vis-à-vis 3D printing.

Multi-dimensional prosthesis can address many of current problems by mimicking natural engineering of the tissue receiving the mechanical assembly prosthesis. Specifically, certain parts of a proximal femur are very stiff and certain parts are less stiff and more flexible. Simulation of these properties in the prosthetic femoral stem/neck/head junction may alleviate many of the unwanted wear patterns currently experienced in installed base.

A mechanical interface between a first prosthesis component and a second prosthesis component, the first prosthesis component including a cavity and the second prosthesis component including an extension to engage the cavity and produce a mechanical join, including: a first mating taper wall of the cavity having a first cross-sectional profile wherein the first cross-sectional profile is non-circular; and a second mating taper wall of the extension having a second-cross-sectional profile wherein the second cross-sectional profile is complementary to the first cross-sectional profile.

A method for constructing a set of mating components of a modular prosthesis, including: a) producing a first component including a cavity; b) producing a second component including an extension configured to engage the cavity; c) defining, during the first component producing step a), the cavity having a first mating taper wall including a first cross-sectional profile wherein the first cross-sectional profile is non-circular; and d) defining, during the second component producing step b), the extension having a second mating taper wall including a second cross-sectional profile wherein the second cross-sectional profile is complementary to the first cross-sectional profile.

A structure for at least a partial insertion into a portion of a bone having a bone variable stiffness profile, including: a first portion configured for installation into the portion of bone, the first portion including a first portion variable stiffness profile simulating the bone variable stiffness profile.

A method for producing a prosthesis to be installed relative to a portion of a bone having a bone variable material properties profile configuring a stiffness profile for the bone, including: a) manufacturing additively a portion of the prosthesis; and b) changing a set of material properties during said manufacturing step a) to produce a variable material properties profile of said portion of the prosthesis simulating the bone variable material properties profile.

A modular implant for at least a partial insertion into a portion of a bone, the portion of bone having a bone variable material properties profile, including: a stem configured for installation into the portion of bone, the stem including a cavity; a neck configured for a first engagement with the cavity with the first engagement configured to mechanically join the neck to the stem, the neck including a trunnion; and a head configured for a second engagement with the trunnion with the second engagement configured to mechanically join the head to the neck; and wherein the neck includes a first reference location, a second reference location spaced apart from the first reference location, and a neck variable material properties profile including the reference locations with the neck variable material properties profile different from and generally compatible with the bone variable material properties profile and with the neck variable material properties profile between the reference locations including a monotonically changing stiffness when extending from the first reference location to the second reference location.

A modular implant for at least a partial insertion into a portion of a bone, the portion of bone having a bone variable material properties profile, including: a stem configured for installation into the portion of bone, the stem including a cavity; a neck configured for a first engagement with the cavity with the first engagement configured to mechanically join the neck to the stem, the neck including a trunnion; a head configured for a second engagement with the trunnion with the second engagement configured to mechanically join the head to the neck; and a support system disposed in a region of a foundation of the implant, the support system configured to provide a propensity for a resistance to a fracture of the region.

An implant for at least a partial insertion into a portion of a bone, the portion of bone having a bone variable material properties profile, including: an insertion portion and an attachment portion, the insertion portion configured for installation into the portion of bone and wherein the attachment portion extends beyond the portion of bone and configured to mechanically join to a prosthetic component; and wherein the insertion portion includes a first reference location, a second reference location spaced apart from the first reference location, and an insertion portion variable material properties profile including the reference locations with the insertion portion variable material properties profile different from and generally compatible with the bone variable material properties profile and with the insertion portion variable material properties profile between the reference locations including a monotonically changing stiffness when extending from the first reference location to the second reference location.

An implant for at least a partial insertion into a portion of a bone, the portion of bone having a bone variable material properties profile, including: an insertion portion and an attachment portion, the insertion portion configured for installation into the portion of bone and wherein the attachment portion extends beyond the portion of bone and configured to mechanically join to a prosthetic component; and a support system disposed in a region of a foundation of the implant, the support system configured to provide a propensity for a resistance to a fracture of the region.

An implant manufacturing process for producing an implant including an insertion portion configured for insertion into a prepared cavity of a live bone, the live bone at the cavity having a bone variable material properties profile, the method including: a) manufacturing additively at least an insertion portion of the implant, the insertion portion including a first set of structural regions and a second set of structural regions, each set of structural regions including a material properties profile; and b) altering, during the manufacturing step a), the material properties profile of each the structural region wherein the material properties profile of the first set of structural regions is different from the material properties profile of the second set of structural regions, wherein the material properties profiles of the sets of structural regions collectively define an implant material properties profile, and wherein the implant material properties profile is configured to produce one or both of a propensity for insertion and a propensity for a resistance to a fracture.

A structural medical device configured for installation into a prepared cavity, including a body including a body portion sized for a pressfit fixation into the prepared cavity; a framework disposed within said body portion; wherein said framework includes a set of one or more structural elements configured to produce an anisotropic bulk material property in said body portion.

A method for producing a structural medical device configured for installation into a prepared cavity, including a) manufacturing a body including a body portion sized for a pressfit fixation into the prepared cavity; and b) disposing a framework within said body portion during said manufacturing step a) wherein said framework includes a set of one or more structural elements configured to produce an anisotropic bulk material property in said body portion.

A method for repairing a fracture of a bone using a template of the bone, including a) reducing the fracture using the template to produce a reduced fractured bone; and b) fixing said reduced fractured bone using a structural medical device spanning a length of the fracture wherein said device includes a body including a body portion, a framework disposed within said body portion, and wherein said framework includes a set of one or more structural elements configured to produce an anisotropic bulk material property in said body portion, said framework including a set of non-biodegradable/non-bioabsorbable stiffness elements, and said anisotropic component including a set of biodegradable/bioabsorbable stiffness elements with said variable stiffness profile changing in a predetermined manner responsive to a degradation/absorbtion of said set of degradable/absorbable stiffness elements; and c) degrading/absorbing selectively, in situ, said set of degradable/absorbable stiffness elements during healing of the fracture without a stiffness-affecting degradation/absorption of said set of non-biodegradable/non-bioabsorbable stiffness elements, while said structure spans said length of the fracture.

A method for repairing a fracture of a bone using a template of the bone, including a) reducing the fracture using the template to produce a reduced fractured bone; and b) fixing said reduced fractured bone using a structural medical device spanning a length of the fracture wherein said device includes a body including a body portion, a framework disposed within said body portion, and wherein said framework includes a set of one or more structural elements configured to produce an anisotropic bulk material property in said body portion, said framework including an anisotropic component having a variable stiffness profile, said anisotropic component including a set of robotic materials with said variable stiffness profile changing in a predetermined manner responsive to a stiffness reconfiguration by said set of robotic materials; and c) adjusting, in situ, said stiffness profile using said set of robotic materials during healing of the fracture, while said structure spans said length of the fracture.

A fixator for a set of fractures in a bone, including a spanning structure having a length spanning the set of fractures, said spanning structure including a framework having an anisotropic component including a variable stiffness profile responsive to a selective degradation of a set of degradable/absorbable stiffness structures while not degrading/absorbing non-degradable/nonabsorbable stiffness structures; and an applicator, coupled to said spanning structure, configured to position and apply said spanning structure to the bone after a reduction of said set of fractures.

A modular structural medical device configured for installation into a prepared cavity, including a body including a body portion sized for a pressfit fixation into the prepared cavity, said body further including a neck socket; a neck configured for a pressfit fixation engagement with said neck socket, said neck including a trunnion portion; a head configured for a pressfit fixation engagement with said trunnion portion; and a framework disposed within said neck; wherein said framework includes a set of one or more structural elements configured to produce an anisotropic bulk material property in said neck.

Any of the embodiments described herein may be used alone or together with one another in any combination. Inventions encompassed within this specification may also include embodiments that are only partially mentioned or alluded to or are not mentioned or alluded to at all in this brief summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 13 illustrates an acquisition of an image for robotic reduction;

FIG. 14 illustrates a robotic reduction of a fracture of a long bone;

FIG. 15 illustrates use of an external fixator for securing a reconstructed long bone;

FIG. 16 illustrates that external fixators to be the stiffest construct and associated with the least amount of blood loss or surgical dissection;

FIG. 17 illustrates an external fixator that is made less stiff than plates and rods due to a change in material properties of a rod used in external fixation;

FIG. 18 illustrates an external fixator that includes a capacity to change/adjust its stiffness properties over time;

FIG. 19-FIG. 23 illustrate various anisotropic rods that may be use for external fixation of long bone fractures;

FIG. 19 illustrates an anisotropic rod for external fixation including a set of orthogonal stiffness structures;

FIG. 20 illustrates an anisotropic rod for external fixation similar to FIG. 19, including a different number of longitudinally extending stiffness structures;

FIG. 21 illustrates an anisotropic rod for external fixation similar to FIG. 19 and FIG. 20, including a different arrangement of longitudinally extending stiffness structures;

FIG. 22 illustrates an anisotropic rod for external fixation similar to FIG. 19-FIG. 21, including a different arrangement of orthogonal stiffness structures;

FIG. 23 illustrates an active anisotropic rod which may include a configuration similar to rods of FIG. 19-FIG. 22, or other arrangements of stiffness structures.

FIG. 43 illustrates a prosthesis including a femoral stem body having a first anisotropic-defining framework producing a desired stiffness profile;

FIG. 44 illustrates a prosthesis including a femoral stem body having a second anisotropic-defining framework producing a desired stiffness profile;

FIG. 45 illustrates a prosthesis including a femoral stem body having a third anisotropic-defining framework producing a desired stiffness profile;

FIG. 46 illustrates a prosthesis including a femoral stem body having a fourth anisotropic-defining framework producing a desired stiffness profile;

FIG. 47 illustrates a prosthesis including a femoral stem body having a fifth anisotropic-defining framework producing a desired stiffness profile;

FIG. 48 illustrates a first modular prosthesis including a body, a head, and a neck, the neck including an anisotropic-defining framework producing a first stiffness profile when assembled;

FIG. 49 illustrates a second modular prosthesis including a body, a head, and a neck, the neck including an anisotropic-defining framework producing a second stiffness profile when assembled;

FIG. 50 illustrates a third modular prosthesis including a body, a head, and a neck, the neck including an anisotropic-defining framework producing a third stiffness profile when assembled;

FIG. 51 illustrates a first acetabular cup with a first anisotropic-defining framework producing a first stiffness profile for the cup;

FIG. 52 illustrates a second acetabular cup with a second anisotropic-defining framework producing a second stiffness profile for the cup;

FIG. 53 illustrates a third acetabular cup with a third anisotropic-defining framework producing a third stiffness profile for the cup; and FIG. 54 illustrates a fourth acetabular cup with a fourth anisotropic-defining framework producing a third stiffness profile for the cup.

DETAILED DESCRIPTION OF THE INVENTION

Figure 1:
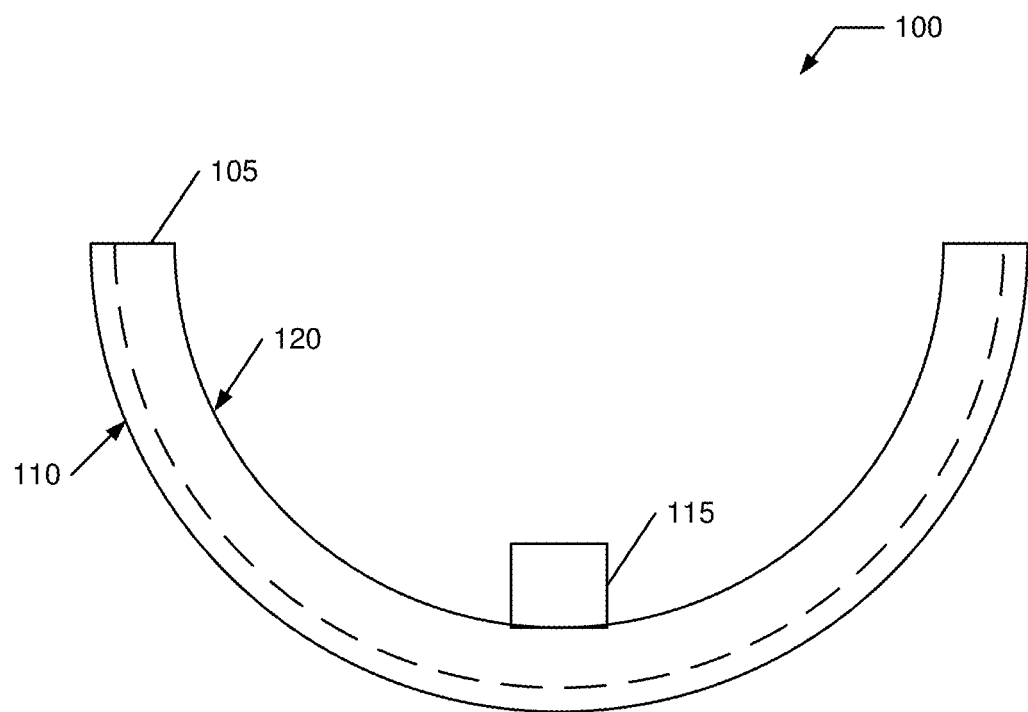
FIG. 1 illustrates a sectional side view of an embodiment of the present invention.

Embodiments of the present invention provide a system and method for improving upon an ability of a surgeon to repair traumatic bone injury using new materials, components, and structures. The following description is presented to enable one of ordinary skill in the art to make and use the invention and is provided in the context of a patent application and its requirements.

Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Definitions

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The following definitions apply to some of the aspects described with respect to some embodiments of the invention. These definitions may likewise be expanded upon herein.

As used herein, the term "or" includes "and/or" and the term "and/or" includes any and all combinations of one or more of the associated listed items. Expressions such as "at least one of," when preceding a list of elements, modify the entire list of elements and do not modify the individual elements of the list.

As used herein, the singular terms "a," "an," and "the" include plural referents unless the context clearly dictates otherwise. Thus, for example, reference to an object can include multiple objects unless the context clearly dictates otherwise.

Also, as used in the description herein and throughout the claims that follow, the meaning of "in" includes "in" and "on" unless the context clearly dictates otherwise. It will be understood that when an element is referred to as being "on" another element, it can be directly on the other element or intervening elements may be present therebetween. In contrast, when an element is referred to as being "directly on" another element, there are no intervening elements present.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common properties.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "connect," "connected," and "connecting" refer to a direct attachment or link. Connected objects have no or no substantial intermediary object or set of objects, as the context indicates.

As used herein, the terms "couple," "coupled," and "coupling" refer to an operational connection or linking. Coupled objects can be directly connected to one another or can be indirectly connected to one another, such as via an intermediary set of objects.

The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent of the given numeric value provided such a deviation does not alter the end function or result of the value. Therefore, a value of about 1% can be construed to be a range from 0.9% to 1.1%.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the terms "optional" and "optionally" mean that the subsequently described event or circumstance may or may not occur and that the description includes instances where the event or circumstance occurs and instances in which it does not.

As used herein, the term "material properties" means a set of measures of a material that may include a composition, an arrangement, a molecular structure, a crystalline structure, a porosity, a grain size, and other non-geometric bulk or macroscopic properties and attributes of the material that influence and set a stiffness profile or other bulk mechanical property. Gross, or bulk, modifications to geometry may be used to provide a varying stiffness profile but it lacks an ability to simulate that of bone with which a prosthesis, or portion thereof, interacts. Variation in material properties, may be accomplished a scale barely perceptible, if at all, to a naked eye, and that aggregation of varied material properties are better able to more closely simulate the material properties of the bone with which it interacts. It being possible that any mismatches, even potentially small localized stiffness mismatches, may contribute to problems experienced by various conventional prosthesis installations including stress shielding and bone resorption.

As used herein, the term "asymmetric" stiffness profile refers to a preestablished characterization of bulk anisotropic material properties of a medical structural device, with these material properties varied non-exclusively non-geometrically responsive to formation of a framework within or on the structural device and more preferably for structural devices bearing greater loads (e.g., acetabular cups, long bone implants and external fixators, and the like) at least partially disposed within a foundation of the structural device. The framework may be defined by one or more sets of ordered variations in homogenous materials and/or sets of organized structural homogenous material elements used in the structural device, and/or may be defined by one or more sets of ordered arrangements of non-homogenous materials used in and/or disposed on the structural device. The framework alters the bulk material properties anisotropically in a manner that is not a function exclusively of geometric variations in the structural device. Some or all of the framework elements may be disposed in a surface layer or on the surface provided it is capable of producing a bulk anisotropic characterization of the structural device. The framework components may be arrayed as one or more sets of structural elements in one-dimensional, two-dimensional, and three-dimensional arrangements, the structural elements may be uniform or non-uniform, homogenous or non-homogenous, the arrangements may be uniform or non-uniform, homogenous or non-homogenous. These sets of framework elements may be distributed in one or more locations within the structural devices.

As used herein, the term "size" refers to a characteristic dimension of an object. Thus, for example, a size of an object that is spherical can refer to a diameter of the object. In the case of an object that is non-spherical, a size of the non-spherical object can refer to a diameter of a corresponding spherical object, where the corresponding spherical object exhibits or has a particular set of derivable or measurable properties that are substantially the same as those of the non-spherical object. Thus, for example, a size of a non-spherical object can refer to a diameter of a corresponding spherical object that exhibits light scattering or other properties that are substantially the same as those of the non-spherical object. Alternatively, or in conjunction, a size of a non-spherical object can refer to an average of various orthogonal dimensions of the object. Thus, for example, a size of an object that is a spheroidal can refer to an average of a major axis and a minor axis of the object. When referring to a set of objects as having a particular size, it is contemplated that the objects can have a distribution of sizes around the particular size. Thus, as used herein, a size of a set of objects can refer to a typical size of a distribution of sizes, such as an average size, a median size, or a peak size.

FIG. 1 illustrates a sectional side view of an embodiment of the present invention represented using a prosthesis 100 including a foundation portion 105 and an exterior contacting portion 110. In some cases, prosthesis 100 may include an optional mounting structure 115 attached to, or integrated with, an interior wall 120.

Prosthesis 100 in FIG. 1 is an acetabular cup used in total hip replacement medical procedures. Prosthesis 100 is installed into a prepared installation site of an acetabulum that defines a reamed socket in a portion of bone of an acetabulum that is about equal to a diameter of the acetabular cup. When installed, exterior contacting portion 110 contacts the bone portion of the installation site. Installation of an acetabular cup requires that it be forced into the installation site while exterior contacting portion 110 is engaged, in varying degrees, with the living bone. Some of the disclosed embodiments provide materials, configuration, arrangement, and orientation of surface elements defined by exterior contacting portion 110 that provide, collectively, an overall asymmetric force with respect to one or more of the contacted portions of the bone portion. In this context, asymmetric force means that engagement forces between the bone portion and prosthesis 100 have a magnitude in one direction of motion (e.g. deeper into the installation) as compared to another direction (e.g., removal from the installation site) that are different. For example, contacting portion 110 may result in installation forces with respect to the installation site that are less than removal forces from the installation site once installed. Other directions and other asymmetries are possible that for some embodiment it may be desirable to have installation forces be greater than removal forces. A magnitude of the asymmetry may be determined by different factors appropriate for a particular embodiment.

Prosthesis 100 depicted as including at least two portions: foundation portion 105 and exterior contacting portion 110 which is not meant to imply any particular manufacturing process, configuration, or arrangement beyond the presence of two functional portions.

Foundation portion 105 may be thought of as providing structural integrity and strength for weight-bearing and loading, and support for exterior contacting portion 110. Exterior contacting portion 110 defines the surface elements that produce aggregate asymmetric forces during contacted motion with bone of the installation site.

Foundation portion 105 and exterior contacting portion 110 may be formed in many different ways. As illustrated in FIG. 1, exterior contacting portion 110 is integrally produced with foundation portion 105 during manufacturing of prosthesis 100. For example, additive manufacturing techniques may be used to define the different portions at different points during the manufacturing. Three-dimensional (3D) printing is a representative class of additive manufacturing equipment that may be used to seamlessly produce prosthesis 100 with exterior contacting portion 110 seamlessly integrated with foundation portion 105.

In other embodiments, prosthesis 100 may be produced using a two-step process in which foundation portion 105 is manufactured first and then in a separate manufacturing process exterior contacting portion 110 is added onto desired surfaces of foundation portion 105 to produce prosthesis 100. In some cases, exterior contacting portion 110 may be produced first as a template and then foundation portion added later.

For purposes of this invention, the term "surface treatment" is used to include all these implementations of exterior contacting portion 110. This term is not limited to any particular arrangement or configuration of exterior contacting portion 110.

As noted herein, one desirable feature of current prosthetic implants includes a surface arrangement for a randomized exterior that includes pores/cavities/voids of a particular characteristic that are used to promote bone in-growth for bonding prosthesis 100 at the installation site. Some configurations of exterior contacting portion 110 may be configured with such in-growth bonding features implemented consistent with the manufacturing technique for prosthesis 100. The surface treatment itself may include a microscopic and/or a macroscopic characteristic dimension for the implementing structural elements.

For example, with the use of additive manufacturing, the set of instructions for forming prosthesis 100 result from a set of instructions executed by the additive manufacturing equipment. That set of instructions may be defined by various 3D design tools and various mathematical instructions. Those instructions may include a superposition of asymmetric structural elements and randomized void-definition processes such that exterior contacting portion 110 includes both of these characteristics. In other embodiments, void-definition processes may be applied to prosthesis 100 after exterior contacting portion 110 is produced with asymmetric force producing structures. Similarly, asymmetric biasing structures may be later added to a device having existing ingrowth structures.

In some cases, prosthesis 100 may be provided with mounting structure 115 which may be implemented in many different ways and used as a mechanism to secure an external tool to prosthesis 100. In one case, structure 115 may include a solid structure attached at an apex of interior surface 120. That solid structure may further define an externally accessible cavity including threaded sidewalls. The external tool may include an extension having an exterior threaded surface complementary to the threaded sidewalls of structure 115.

In use, an operator may attach the external tool (an example is illustrated later in FIG. 8) to mounting structure 115 and begin to apply an inserting force prosthesis 100 into an installation site. That inserting force may be a non-impacting force applied by a BMD-type device as described in the incorporated patents and applications or it may be an impacting force applied by a mallet, hammer, or the like. Exterior contacting portion 110 may be configured so a net insertion-resisting force relative to the side walls of the installation is less than a net withdrawal-resisting force relative to the side walls. This arrangement may allow for decreased installation forces as opposed to a prosthesis having an outer surface with symmetric or randomized resisting forces. In some implementations, each incremental depth increase may be performed with less inserting force and each position may be thought of being anchored in place with a bias to increasing the installation depth responsive to forces applied to and by the external tool.

In some embodiments, when the asymmetric forces have enough differential, and when the installation site is prepared in an appropriate fashion, some embodiments may allow for insertion to result from generalized low-level vibration or periodic forces that bias prosthesis ever deeper into the installation site.

Figure 2:
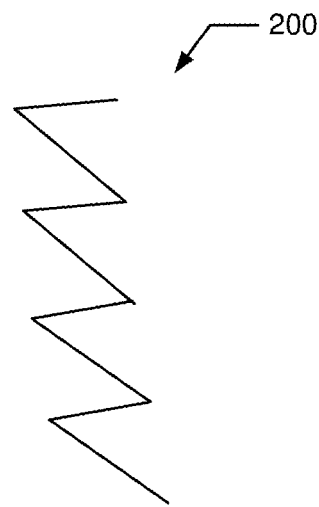
FIG. 2 illustrates a sectional side view of an embodiment of a surface treatment.
Figure 3:
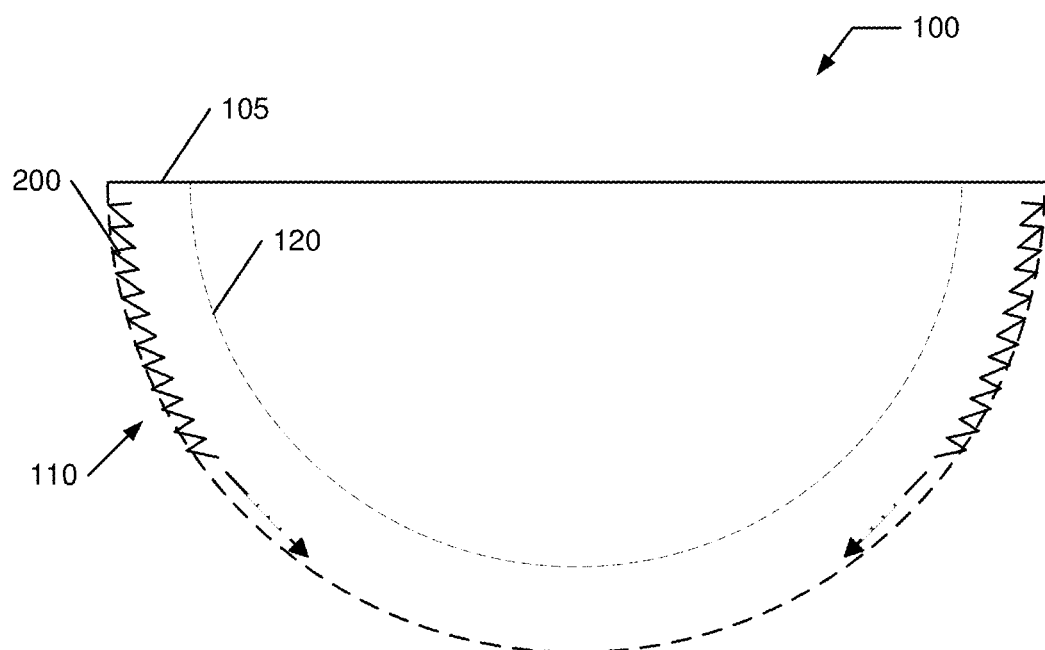
FIG. 3 illustrates a sectional side view of an embodiment of the surface treatment of FIG. 2 applied to a prosthesis of FIG. 1.

FIG. 2 illustrates a sectional side view of an embodiment of a surface treatment 200. Surface treatment 200 includes a series of asymmetric "steps" that may be included as all, or a portion of, exterior contacting portion 110, extending 360 degrees around foundation portion 105 when viewed from above. FIG. 3 illustrates a sectional side view of a surface treatment 200 included as part of prosthesis 100 as exterior contacting portion 110. In some embodiments, surface treatment 200 may not extend over an entire height of prosthesis 100. In some embodiments, surface treatment 200 may not include a regular step profile. The step profile of surface treatment 200 is representative of asymmetrically angled surface elements of the type that may be used for asymmetric resisting forces.

Figure 4:
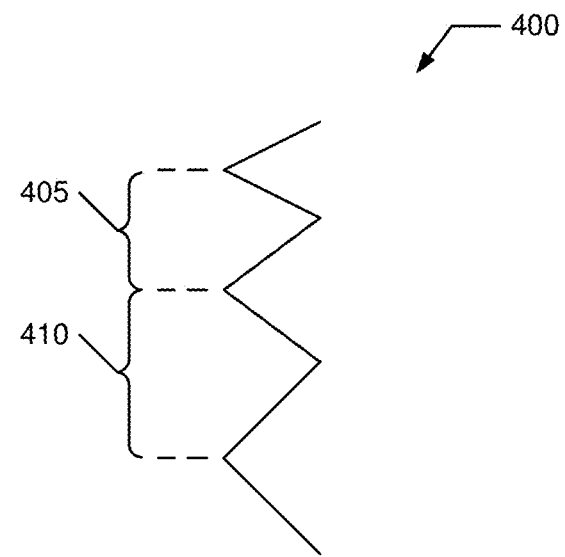
FIG. 4 illustrates a sectional side view of an alternative embodiment of a surface treatment.
Figure 5:
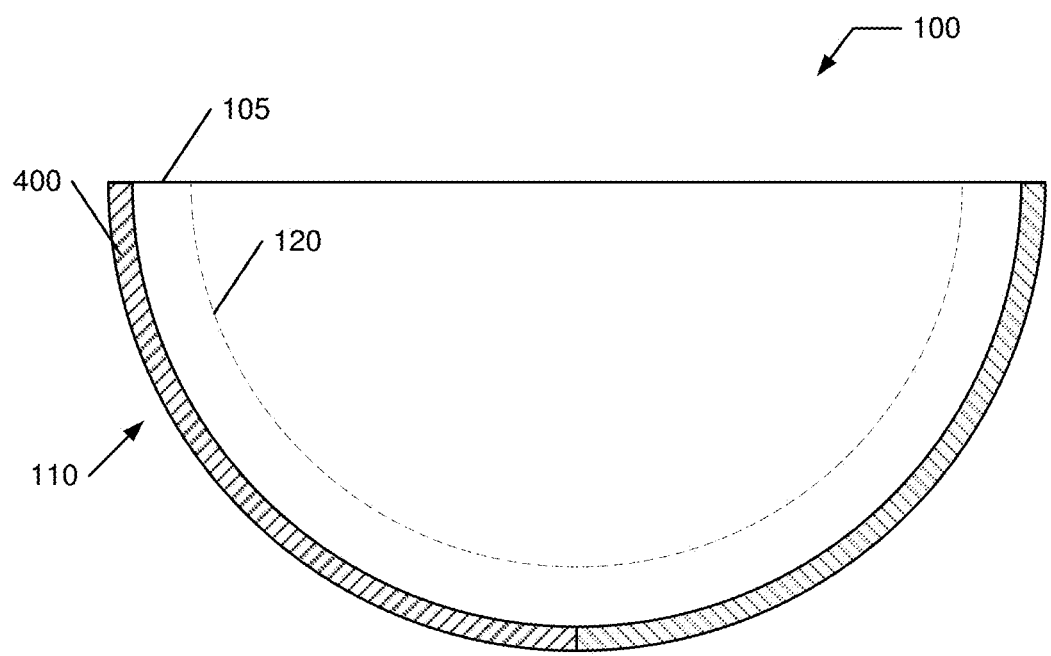
FIG. 5 illustrates a representative sectional side view of an embodiment of the alternative surface treatment of FIG. 4 applied to a prosthesis of FIG. 1.

FIG. 4 illustrates a sectional side view of an alternative embodiment of a surface treatment 400. Surface treatment 400 illustrates a concept of variable pitch in which a first distance 405 between a first set of adjacent peaks of surface treatment 400 is different than a second distance 410 between a second set of adjacent peaks of surface treatment 400. There are many different possible implementations for surface treatment 400. While surface treatment 400 is illustrated as having continuously variable distances between a pair of peaks, surface treatment 400 may also be implemented as having a first portion of substantially matching (or varying using a first variable peak profile) pitch distances and then having one or more additional portions, each portion including substantially matching (or varying using the same or additional variable peak profiles) pitch distances within its portion. That is to say, a top portion, perhaps a top quarter or a top third of prosthesis 100, for example, may include a first configuration for pitches as part of surface treatment 400 while a bottom portion, perhaps a bottom quarter or a bottom third of prosthesis 100, for example, may include a second configuration for pitches as part of surface treatment 400. FIG. 5 illustrates a representative sectional side view of surface treatment 400 included with prosthesis 100 as exterior contacting portion 110. The variable pitches may provide for asymmetric resisting forces. As illustrated, surface treatment 400 includes a generally symmetric peak pattern. In some embodiments, surface treatment 400 may include a modification of surface treatment 200 to include one or more regions of variably spaced "asymmetrically-angled peaks" when included as part of exterior contacting portion 110.

The distribution of these portions may be other than this example (top and bottom portions) and different regions and portions may have different expanses (e.g., a top third and a bottom quarter) for example. In other embodiments, exterior contacting portion 110 may include one or more regions of surface treatment 200 and one or more regions of surface treatment 400.

Figure 6:
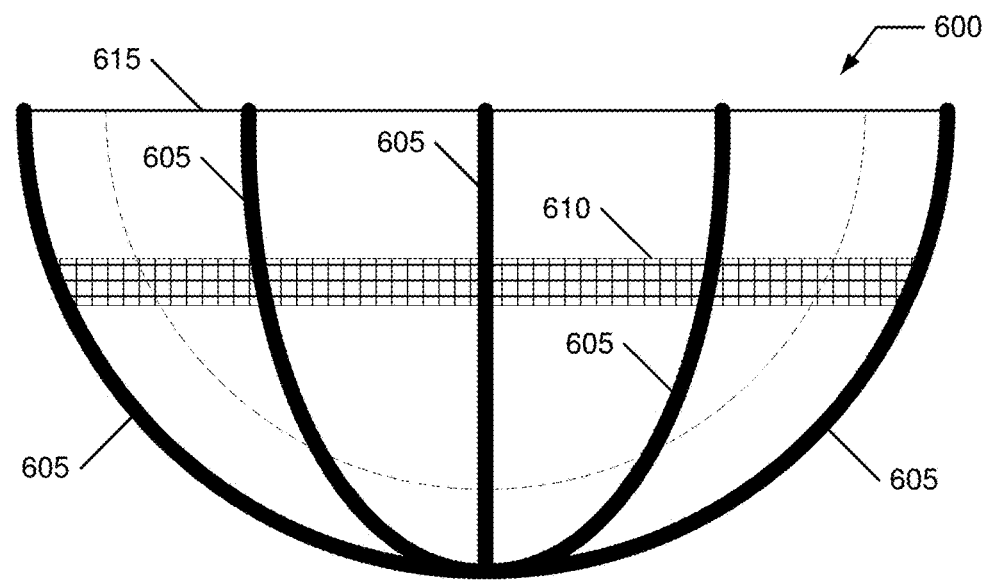
FIG. 6 illustrates a side view of a prosthesis including a two-dimensional asymmetrical stiffness.
Figure 7:
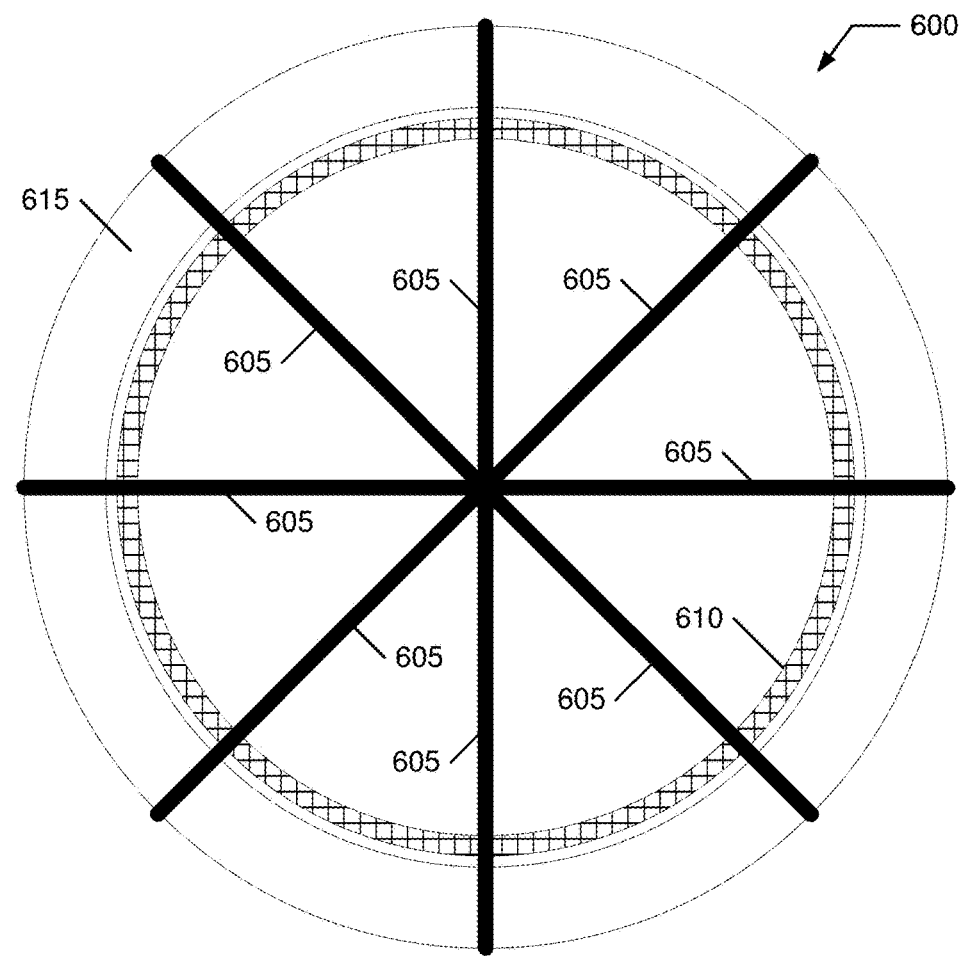
FIG. 7 illustrates a top view of the prosthesis of FIG. 6.

FIG. 6 illustrates a side view of a prosthesis 600 including a two-dimensional asymmetrical stiffness configuration, and FIG. 7 illustrates a top view of prosthesis 600. Prosthesis 600 includes a set of ribs 605 and one or more planks 610 disposed as part of a prosthetic body 615, represented as an alternative acetabular cup. Body 615 may be implemented in conventional fashion or may include an arrangement consistent with prosthesis 100. Ribs 605 and plank(s) 610 are configured to provide an asymmetric two-dimensional (2D) stiffness to body 615 that may be more conducive to transmission of force and energy through the longitudinal axis of the cup as opposed to circumferentially. Ribs 605 are longitudinally extending inserts within body 615 (and/or applied to one or more exterior surfaces of body 615). Plank(s) 610 is/are laterally extending circumferential band(s) within body 615 (and/or applied to one or more exterior surfaces of body 615). For example, planks 610 may be "stiffer" than ribs 605 (or vice-versa) to produce a desired asymmetric functional assembly that may provide for an undulatory body motion as it is installed into position.

The illustration of FIG. 6 is not to be understood as implying that the present invention requires that ribs and planks be maintained at relative right angles as illustrated. In some implementations, to achieve a desired affect or motion, other angular relationships between the ribs and planks are possible (e.g., 30, 45, 60 degree relationships, or more generally an angular (which may be constant or varying at different locations) range of 5-90 degrees.

An alternate implementation could include other arrangements of intersecting multidimensional (e.g., 2D or 3D structures) such as a pair of counter-cyclical helical structures implemented in a body of a prosthesis. That is, for a prosthesis having a particular axis, one structure is installed clockwise about that axis and another structure is installed counterclockwise about that axis. The frequency of wrap, material type, tension, nature of integration, and other factors influence the asymmetric stiffness imparted by these structures that in turn may influence a resulting undulatory motion in response to forces moving the prosthesis along an installation path. In some cases, it may be desired to provide a particular undulation motion for removal rather than for installation as the present invention is not constrained to just improving installation of a prosthesis into a bone.

In some embodiments, a use of a tool, for example a BMD prototype, allows an operator to insert a prosthesis with more control and less force. Use of such a tool coupled with prosthesis 600 that has an asymmetrical "structural" and hence asymmetrical "functional" propensity for longitudinal seating, the operation may be able to be completed with less force, and thus more safely, efficiently, and/or accurately.

The acetabular cup and all implants in orthopedic surgery may benefit from various types of differentiation (where the structure of the implant in and by itself) enhances the functionality of the implant. Prosthesis 600 may alternatively, or in addition, include a "cross helical arrangement" of fibers, strands, cables, ropes, or other structures to be simulated on the surface of, or in the body of, prosthetic implants (e.g., acetabular cups) and hence the creation of "two dimensional stiffness". The creation of "fiber angels" on the surface of the implant creates better and easier seating of the implant, with more efficient transmission of force from an insertional tool to the cup (implant) to the pelvic bone.

Prosthesis 600 may be referred to generally as an "intelligent prosthesis" and acetabular cup where the manipulation of the structure and surface of the implant significantly affects the functionality of the implant particularly during the actual surgery, this implant will have been fine-tuned functionally to insert. This cup through its inherent structural specifications discussed above will complement the use of BMD vibratory insertional tool (bidirectional or unidirectional versions). This concept may apply to many different orthopedic implants used for reconstruction and trauma, and other structures to be inserted or assembled together.

Figure 8:
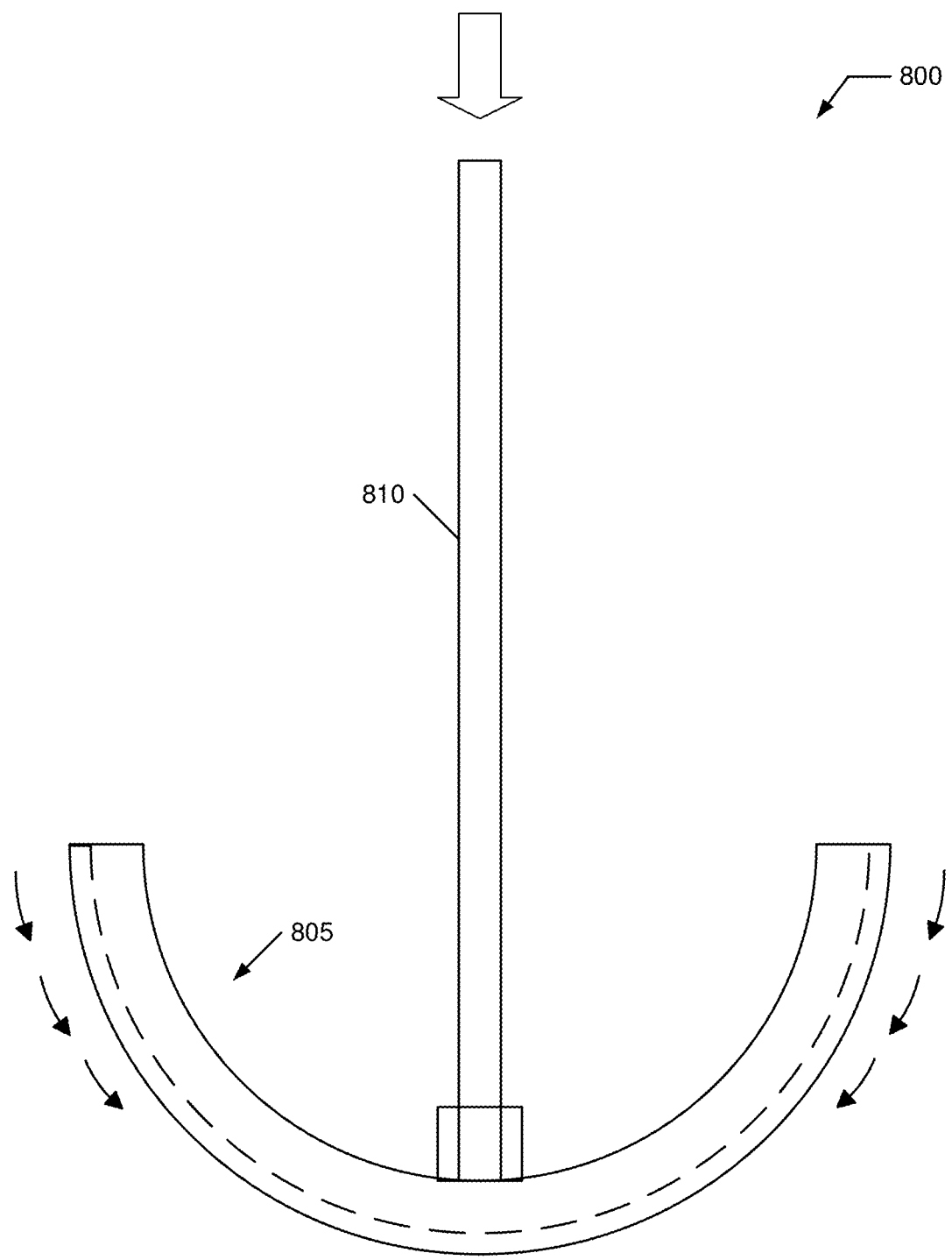
FIG. 8 illustrates a side view of a pulling of a prosthesis along an installation path responsive to an apex-attached force applicator.

FIG. 8 illustrates a side view of a system 800 pulling a prosthesis 805 along an installation path responsive to an apex-attached force applicator 810. In some cases, for a prosthesis having 2D functional asymmetry, it may be desirable or undesirable to pull prosthesis 805 in such as fashion depending upon the differing moduli of stiffness and arrangement of components. In some arrangements, it may be undesirable to pull prosthesis into position in the manner illustrated in FIG. 8.

Figure 9:
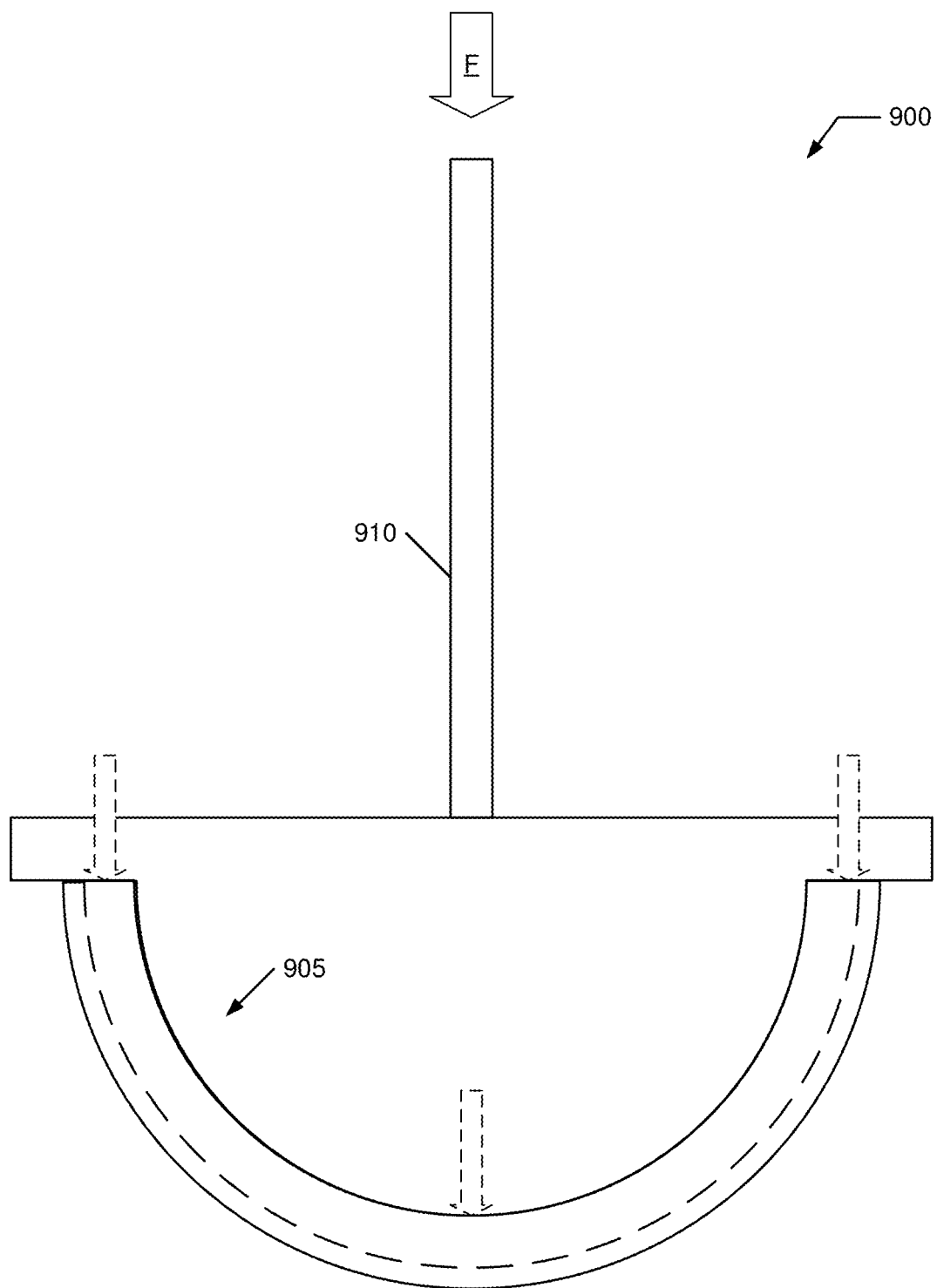
FIG. 9 illustrates a side view of a pushing of a prosthesis along an installation path responsive to a whole-surface interior adaptor force applicator.
Figure 10:
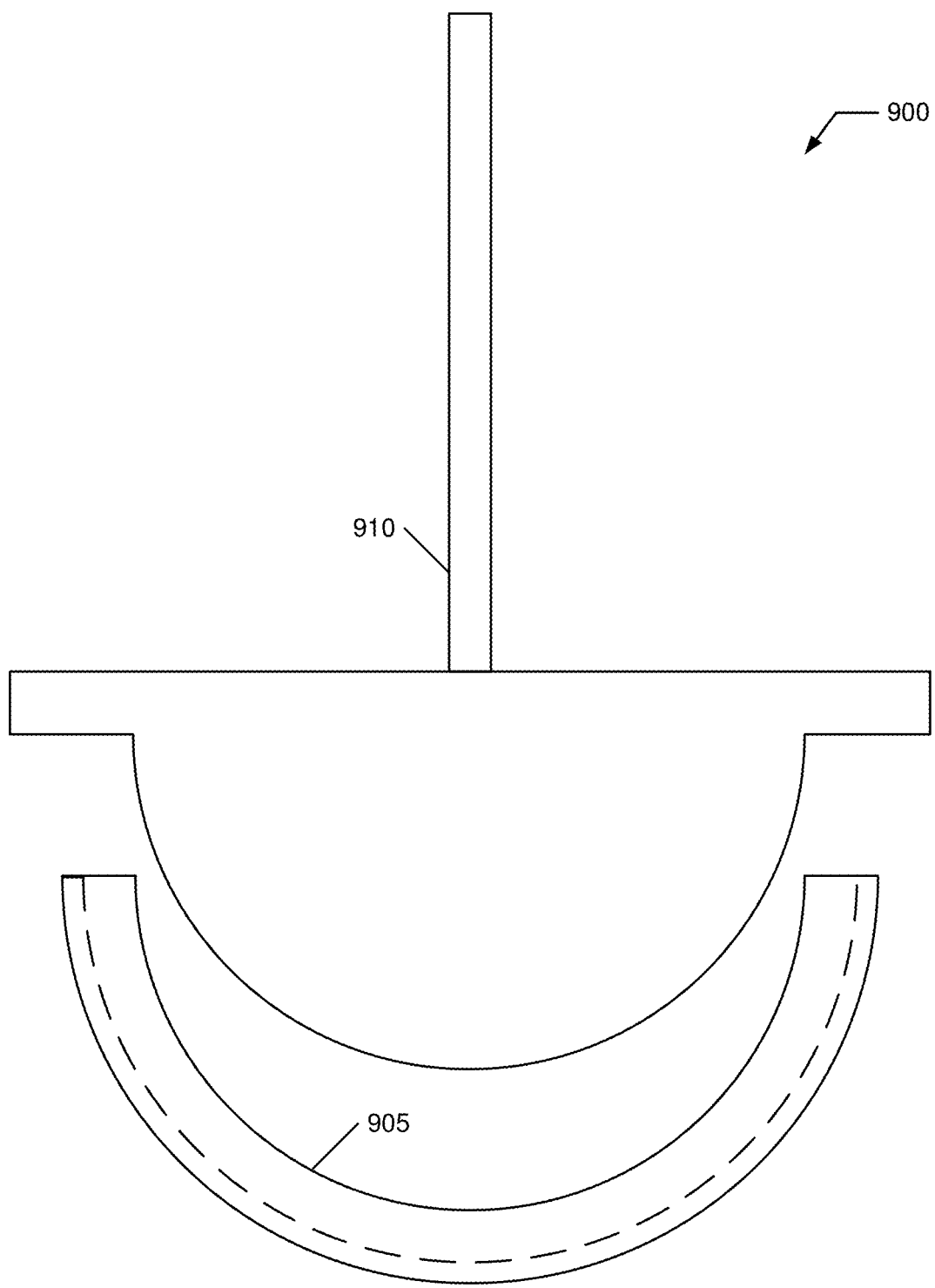
FIG. 10 illustrates a side view of the whole-surface interior adaptor force application disengaged from the prosthesis to better illustrate its configuration.

FIG. 9 illustrates a side view of a system 900 pushing of prosthesis 905 (e.g., prosthesis 600) along an installation path responsive to a whole-surface interior adaptor force applicator 910, and FIG. 10 illustrates a side view of system 900 with whole-surface interior adaptor force applicator 910 disengaged from prosthesis 905 to better illustrate its configuration. Applicator 910 sits into prosthesis 905 and "pushes" it down into position. In some embodiments may provide that "pushing" prosthesis 905 into position with applicator 910 (such as a BMD or a BMD-type device) possibly engages an undulatory motion of prosthesis 905 more effectively, such as in some cases when prosthesis 905 includes an embodiment of prosthesis 600 configured for undulation in response to an appropriate series longitudinal insertion forces F.s Another embodiment of the present invention may include a material applied alone or as part of another surface treatment to contacting surfaces of a prosthesis. This embodiment includes a completely novel idea for insertion of a prosthesis such as an acetabular cup. Depending upon context, there are materials that may significantly decrease relative friction between two contacting objects moving past each other. A use of a BMD vibrational tool may help to facilitate the use of similar concept. An embodiment may include a bio-absorbable or bio-degradable material (e.g., a paste, cream, gel, or other substance) configured for use during the insertion process, e.g., of an acetabular cup into the acetabulum, to decrease the relative forces between contacting surfaces at the cup and bone interface. For example, this material could be an antibiotic paste that absorbs immediately after insertion, or a rapidly dissolving paste such as calcium hydroxylapatite (HA) [Ca10 (OH)2 (PO4)6], Beta tricalcium phosphate, an HA/B TCP combination; all of which can be made into paste and slurries that dissolve over controlled amounts of time. An embodiment of the present invention may include use of a surface-applied material (such as a cream, gel, paste or the like) to minimize relative forces during the insertion/assembly of an implant with a tool, such as the BMD prototype or other installation tool. Of course, this idea applies to other implants, for example those that require the use of force and that would benefit from the BMD vibrational insertion tool, as well as other procedures and tools.

Surface treatment and/or application of a surface material may reduce installation forces. One possible theory is that the surface treatment and/or surface material manipulates of the applicable friction coefficients through shifting a contribution from static to kinetic coefficients as well as reducing the applicable static and/or kinetic coefficient. For a surface treatment such as a paste, slurry, ice, or the like, such manipulation may be temporary during the time that the prosthesis is installed. Thereafter the values for the coefficients may revert to the previous, unaltered values. This may be used to advantage in helping to improve the retentive forces holding the prosthesis in place after installation.

Described herein is use of a paste or slurry that absorbs over time after installation (in some cases quickly such as ice) after the insertion (HA) [Ca10 (OH)2 (PO4)6], Beta tricalcium phosphate, and HA/B TCP combination, all of which may be made into a paste and/or a slurry that can be applied to the surface of the cup and dissolve over a controlled period of time, preferably immediately after the insertion of the cup is complete. In addition, there is another concept that uses a more simple and ubiquitous phenomena to reduce installation forces (e.g., possibly to reduce the applicable coefficients of friction), in order to allow easier insertion of the acetabular prosthesis into the acetabulum. That is to create a simple method of freezing sterile water on the cup and within the porous coating surface of the cup to provide a full or partial ice film at the juncture of the cup and the bone of the installation site. The porous coating comprises of microstructural features such as peaks, valleys and deep caves. In one sense, this structure may mimic the structure of trabecular/cancellous bone with its three-dimensional and interconnecting network of pores and capillary properties. The porous coating aids in initial scratch fixation as well as long term fixation through osseointegration of bone with its surface. Recently, there have been many advances in the creation of the porous coating that more accurately resemble the trabecular bone. Filling these gaps with sterile ice water that is then frozen is expected to dramatically decrease the applicable installation forces (possibly by reducing the applicable coefficients of friction) and hence FR (resistive force for insertion of a cup into a cavity). This method of using ice water is ideal in that as soon as the cup is exposed to the body fluids the ice will melt returning the coefficient of static friction (for the cup/cavity interface) to its original value before the application of ice. In this manner whether a biological paste, antibiotic paste, or ice is utilized, the coefficient of static friction may be temporarily (disarmed) so that easy insertion can occur. All of these methods whether they rely on the paste, slurry or ice perform the same function to temporarily diminish the FR or applicable resistive force(s) for the cup/cavity interaction, and resolve shortly after insertion, and thereby return the relative forces to unaltered values—except that after installation these resistive now resist removal in contrast to resisting installation. This is akin to "tricking" the body to open up a short window of time to allow easy insertion of a prosthesis. This is a new and novel method that can be utilized to make acetabular cup insertion easier with any insertion tool or method, including with the disclosed and incorporated devices, systems, and methods.

Figure 11:
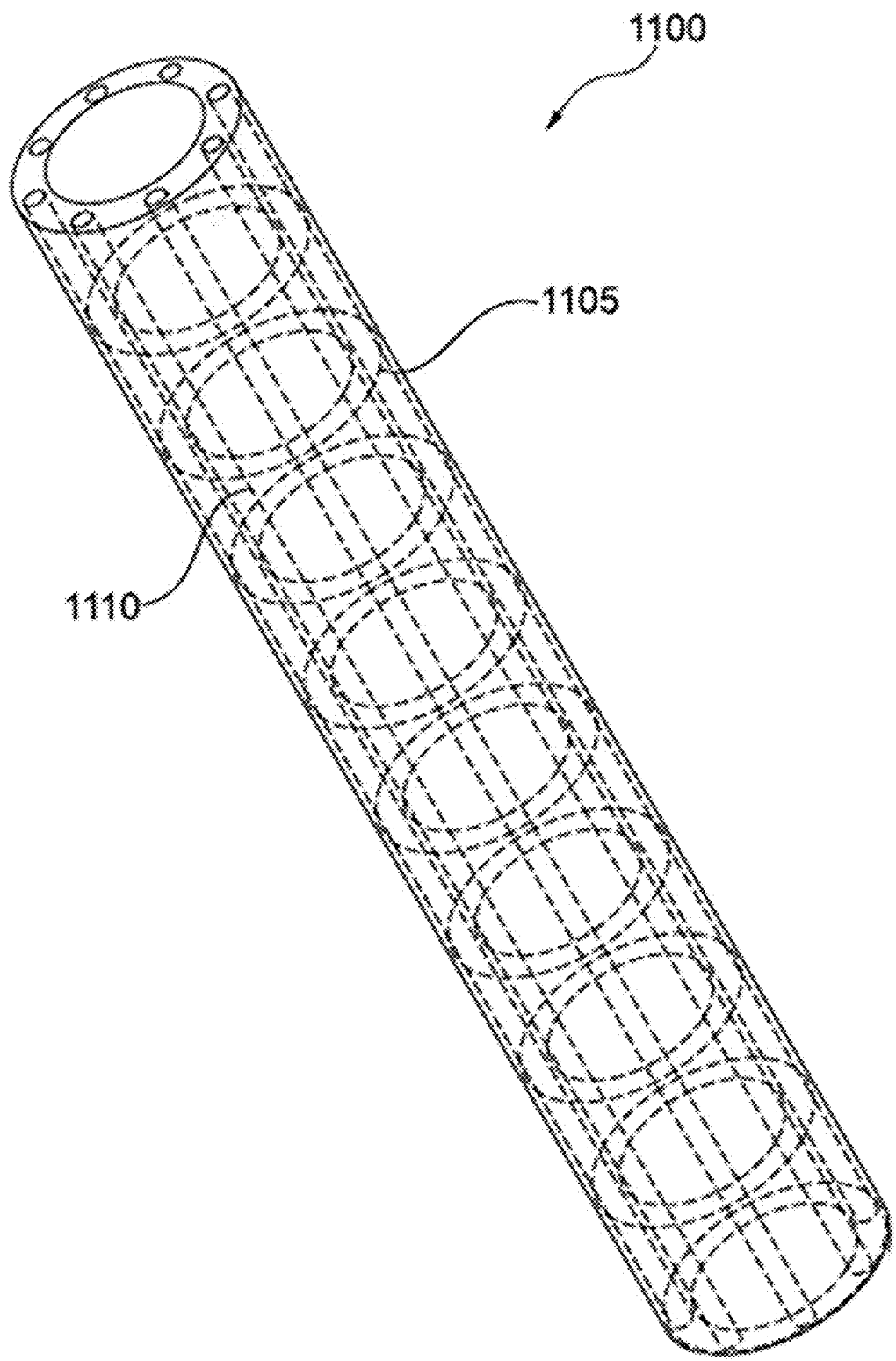
FIG. 11 illustrates an alternative embodiment of a two-dimensional asymmetric implant illustrated in FIG. 6-FIG. 7.

FIG. 11 illustrates an alternative embodiment of a two-dimensional asymmetric implant 1100 similar to prosthesis 600 illustrated in FIG. 6-FIG. 7 and described herein. Implant 1100 is illustrated as an intramedullary rod, also sometimes referred to as an intramedullary nail (IM nail) or inter-locking nail or Küntscher nail, which may or may not include proximal or distal fixation. Implant 600 may include an elongate structure forced into a medullary cavity of a bone, such as used to treat trauma (e.g., fractures of long bones of the body). Implant 1100 conforms generally to prosthesis 600, and its options, except for the shape and use. Implant 1100 includes a set of circumferential ribs 1105 and a set of longitudinally-extending planks 1110 that have a rigidity/flexibility different from ribs 1105. For example, it may be desirable to provide ribs 1105 more rigid than planks 1110. FIG. 11 illustrates an implementation having ribs 1105 being circumferential (and more rigid) and planks 1110 being longitudinal (and less rigid relative to ribs 1105). In some embodiments and implementations, ribs 1105 and planks 1110 may have a different orthogonal relationship with planks not parallel to a longitudinal axis in contrast to that illustrated in FIG. 11. Further, some embodiments and implementations may include counter-directional helical regions defining differential bias. Counter-directional helical regions may have differing relative twist rates along the longitudinal axis. Further, some embodiments may include a surface treatment as described herein. For example, a surface treatment may be included in addition to, or in lieu of, the foundational asymmetric biasing arrangement. The surface treatment may be asymmetrically biased to aid in implantation or aid in removal, depending upon an intended direction of installation into a bone cavity. Implant 1100 may be solid including one or more layers, such as a foundation or core layer, and one or more surrounding layers and may include an exterior or surface layer. In some embodiments, there may be a central open shaft or longitudinally-extending cavity (e.g., a cylindrical opening extending an entire length of the implant).

Described herein and in the incorporated patent applications are embodiments that may include several concepts involving manufacturing of orthopedic implants (including additive manufacturing "AD") to enhance one or more functions of those implants.

These functions may include two, three, or more dimensional stiffness (undulatory motion) which may create a bias for insertion for example for (an acetabular cup or IM rod), external surface preparation (e.g., at a micron level) with bias for insertion, and "variable stiffness prosthesis" (e.g., adjusting a porosity and a crystalline structure at the microscopic level) simulating natural local mechanical properties of bone (to prevent stress shielding and bone resorption). Variable stiffness prosthesis may also be invoked to build prosthesis that can better withstand high local stresses at prosthesis to prosthesis interfaces (as in the trunnion/head junctions) to prevent tribocorrosion and fretting and to address a problem of trunnionosis. Embodiments have described a two-dimensional stiffness of implants (e.g., with ribs and planks) for use with vibratory insertion forces for easier insertion.

Disclosed herein is an expansion on the embodiments of functional implants which can be created with or without AD for use in trauma and tumor and reconstructive surgeries.

The science of fracture healing continues to be elucidated. There are several concepts worth quick review. Traumatic fractures of long bones are generally stabilized in one of three methods: a) intramedullary rod fixation, b) plate-fixation, and c) external fixation. There are advantages and disadvantages to each of these techniques. Certain negative traits are generally attributed to each of these fixation techniques that can lead to poor healing of the fractured bone (Non-unions).

1. Plate Fixation: This method of fixation has generally been associated with extensive periosteol (the external covering of bone) stripping of bone, which can lead to devascularization of bone and therefore slow, or non-healing of fractured bone. More recent techniques emphasize less dissection of the surface covering of bone (less periosteal stripping) to maintain vascularity and allow better healing; bridging with a plate. The second negative issue associated with plate fixation is that metal plates are rigid and with multiple points of fixation with screws a very rigid construct is created that can affect proper bone healing, again leading to delayed union or non-union.

2. A quick review of the biology of fracture healing follows. Bone formation is either "Enchondral" as in long and short bones or "Intramemebranous" as in flat bones of the skull. The inner two thirds of cortical long bones are vascularized by nutrient arteries that pass through the diaphysel cortex and enter the IM canal; these arteries get damaged when reaming is done to prepare the canal for a rod. The outer one third of the cortical bone derives blood from the periosteal membrane vessels, which are at risk from periosteal stripping that occurs during exposure for plate fixation.

Fractures commonly heal with a combination of enchondral (cartilaginous base) and intramemebranous (primary) bone formation. Motion at the fracture site results in healing primarily through enchondral ossification, whereas stability at the fracture site enables direct 'primary bone formation' through intramemebranous ossification. Fracture healing occurs in a sequence of biologic stages including inflammation, hematoma maturation, hypertrophic cartilage formation, new bone formation and remodeling to mature bone [Callus Formation].

Bone is a live structure with 70% of its extracellular matrix composed of mineral components, and 30% composed of organic components (90% type 1 collagen and 5% noncollagenous proteins). The structure of cortical bone shows cortical lamellar bone: interstial system, osteonal lamalle, and outer circumferential system. There is an intricate vascular system to provide nutrition to the living cells in bone (osteocytes). The complex arrangement of the microstructure and meso-structure of bone including the lamellar rings and interstial lamellar and external circumferential lamellar system is noted. A combination of the microstructure, mesostructure and macrostructure of bone may allow bone to be anisotropic and viscoelastic in nature. Viscoelastic material has properties that are rate dependent or have time-dependent responses to applied force. An anisotropic material has properties that differ depending on the direction of load. Bone, muscle, ligament, and tendons all are anisotropic and viscoelastic. An isotropic material has the same mechanical properties in all directions. In general metals and ceramics are isotropic.

Too rigid a fixation may interfere with the above process of callus and subsequent bone formation.

3. External fixation has an advantage of not damaging either the endosteal or periosteal blood supplies however it has a bad reputation of being and extremely stiff construct that limits physiological motion required for formation of callus/bone. Its use is therefore limited to open fractures. It is rarely used as a definitive form of routine fracture fixation.

4. IM rod fixation traditionally has been the most accepted form of long bone fixation due to higher and more rapid healing than the other two techniques. It is postulated that this form of fixation allows more physiological transmission of loads across the fracture site allowing natural callus formation and bone healing. However, this process typically requires reaming of the diaphaseal canal, which damages the endosteal blood supply to bone, and as well there is a general physiological cardiopulmonary risk to the patient with the process of reaming and intramedullary rod application: fat emboli to the lungs, which is a disadvantage to a trauma patient.

A problem is that bone is anisotropic, and the metals used to stabilize bone for fracture fixation are isotropic. Conventional metal and materials used in implants, rods, and prosthetics is rigid in all directions and does not allow varying physiological loads to the bone. This disparity could block the necessary and appropriate allowance of physiological motion required for proper fracture healing. Some embodiments of the present invention are intended to produce a better metal that simulates bone's material and mechanical properties (e.g., to use in fracture fixation) in order to allow natural healing of bone in fracture care. Currently there are five different ways a bone can be stressed: a) tension, b) compression, c) torsion, d) bending, and e) shear.

It is not known or well understood what type or combination of physiological stresses leads to or (are necessary) for optimal physiological callus formation. This is a subject of future investigations.

Some embodiments of the present invention may include specification and use of anisotropic and viscoelastic metals and materials. Since the crystalline and lattice structure of metal and other materials can be manipulated and microscopic and mesoscale levels. The Young's modulus of elasticity for cortical bone is approximately 20 GPa (Gigapascals). The modulus of elasticity for stainless steel is about 200 GPa, and that of titanium is about 100 GPa.

An embodiment may include manufacturing of crystalline metal and material in such a way to simulate the internal architecture of compact and cortical bone. With osteonal lamalle, interstitial lamalle, and circumferential lamalle of concentric cortical bone. It may be that this microcale and mesoscale architecture is what provides anisotropic and/or viscoelastic nature to bone.

Figure 12:
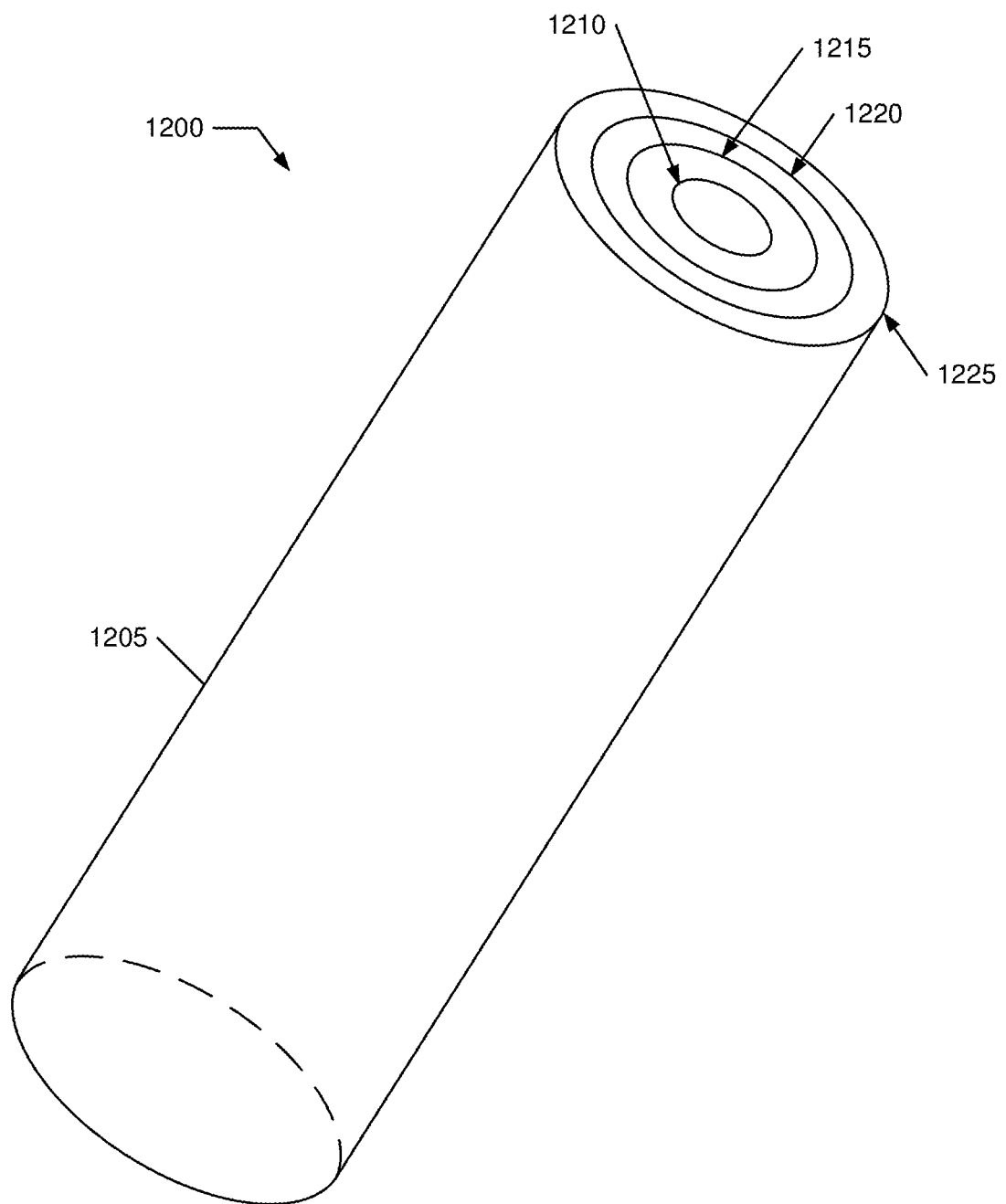
FIG. 12 illustrates an implant in a rod format including a varying cross-sectional stiffness.

Alternatively implants and rods may be created with variable decreasing or increasing stiffness concentric rings, as in the structure of trees, again simulating natural engineering concepts that likely confer anisotropic and viscoelastic properties. FIG. 12 illustrates an implant 1200 in a rod format including a varying cross-sectional stiffness. A shaft 1205 of implant 1200 may include a core 1210, and three layers (a layer 1215, a layer 1220, and a layer 1225). Each layer may include a different modulus of elasticity as follows: core 1210=80 GPa, layer 1215=60 GPa, layer 1220=40 GPa, and layer 1225=20 GPa. Other implementations may have other arrangements and modulus distributions.

At a microscopic level an embodiment may include simulation of a triple helix structure of collagen fibrils arranged in specific quarter-stagger array seen in electron microscopy, potentially conferring the viscoelastic nature to bone. Also, an embodiment may include an oblique arrangement of metallic "fibrils" to simulate an oblique arrangement of collagen fibers in bone.

Ultimately when a proper anisotropic and viscoelastic metal is created, it may completely change the way fracture fixation is approached. Formation of anisotropic metals in addition to the discovery of the optimal physiologic loading for callus formation can make future fracture fixation less invasive and more effective.

Anisotropic/Viscoelastic metals and materials may be used for plate-fixation, intramedullary rod fixation, and external fixation.

There may be a particular advantage for use of anisotropic metals and other materials with external fixators, particularly in a case of a trauma patient and an injured soldier or warrior.

When external fixators are attached to anisotropic metals that allow transmission of certain physiological stress at the fracture site, it is predicted that callus formation may not be impeded, but rather enhanced. Should an external fixator be effective in allowing healing to take place (without risk of non-union; to which it generally has a high association), the need for additional dissection through (by periosteol stripping for plate fixation) or (reaming for intramedullary rod fixation) would be obsolete and unnecessary. The surgeon would apply the Shantz pins to the cortical bone above and below the fracture and apply the spanning anisotropic metal bars. Fracture healing could occur rapidly, and the fixator would be removed. This would confer a huge advantage to the injured soldier who is typically a multi trauma patient under huge cardiopulmonary and physiological loads. In fact, IM rod fixation has been generally the fixation of choice but has definite negative physiological consequences. Similarly, plate fixation can be applied too rigidly leading to non-union and requires extra dissection with additional surgery and bleeding.

Should fractures for trauma patients be effectively treated with external fixators, minimum physiological and cardiopulmonary load may be imparted to the patient. Also, there is less bleeding and less operative time.

Some embodiments may include a concept of fracture fixation with robotic surgery and computer navigation. Currently robotic surgery computer navigation is common in the orthopedic operating room, however, typically relegated to arthroplasty surgery. Computer navigation and robotics have an ability to landmark a position of the patient's bones in the operating room (OR) space. Computerized tomography (CT) based techniques may match a previously imaged bone to the patient's body in the OR space.

An embodiment of the present invention may include the following process for fracture fixation and stabilization for the trauma patient:

1. CT of the opposite extremity (or for the solider, a set of extremities are imaged before deployment) is obtained. The opposite extremity is a close approximation of the injured extremity in more than 99% of cases. A mirror image of the studied body part (for example of a femur) is produced in the robot, or computer navigation 2. External fixator pins are applied above and below the fracture site, and these Shantz pins are attached to the robot or computer navigation system. The arms of the computer will use the template of the uninjured bone (mirror image with right-left reversal) to propose a close estimation of the fractured bone. The computer/robot will reduce the fracture through internal software program that tells it to re-approximate the fractured fragments to the model derived from the CT of the uninjured side.

3. Once the reduction is complete, the surgeon applies the anisotropic and viscoelastic metal bars to span the fracture. There will be no need for additional surgery or conversion to plates and or rods.

4. Rods and implants of varying stiffness can be produced (all anisotropic/viscoelastic in nature) that can easily be exchanged in clinic when the construct requires adjustment (e.g., to be more or less stiff).

This process is believed to include a novel method of fracture fixation and treatment that can revolutionize fracture care especially in trauma patient and injured soldier.

Figure 13:
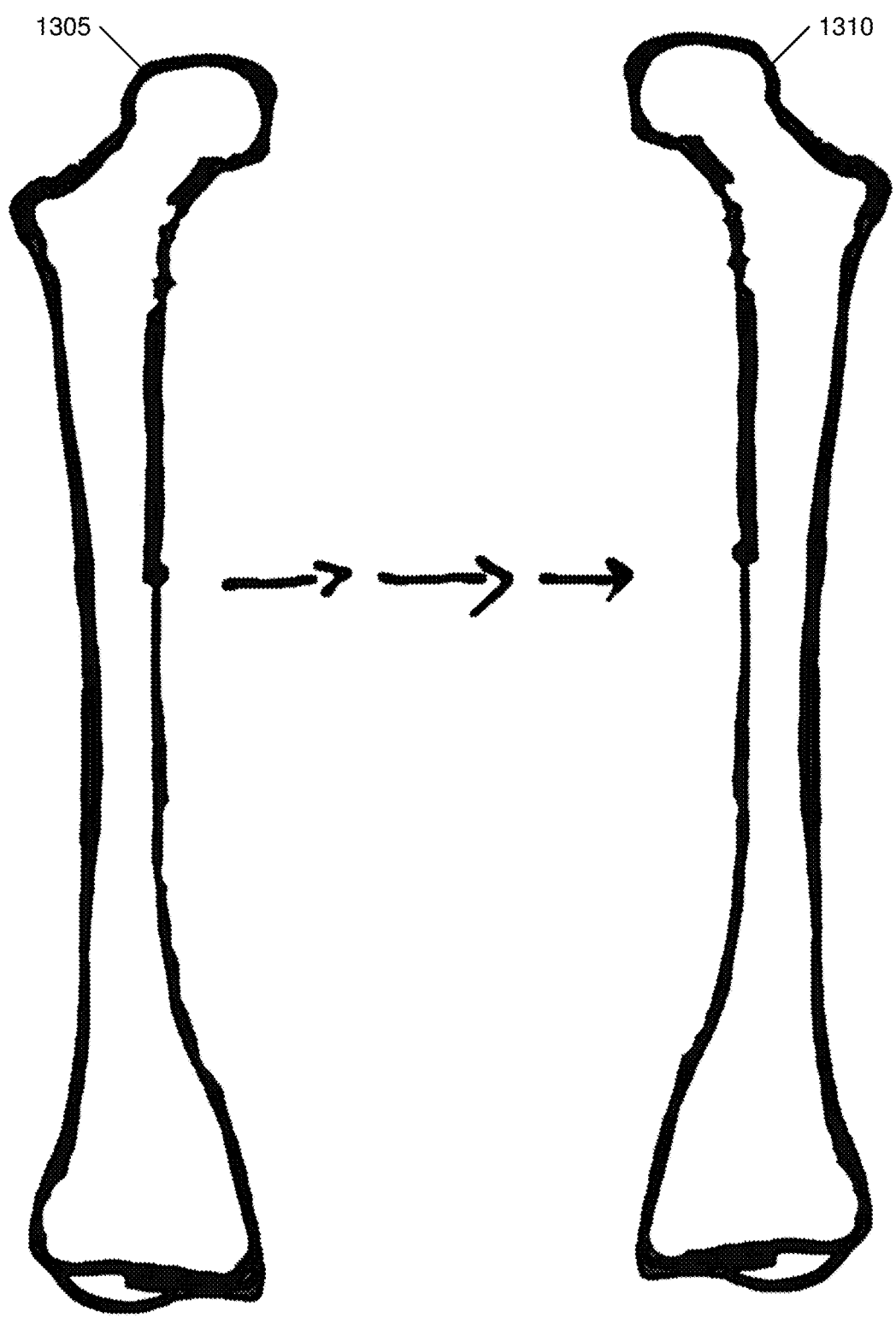
FIG. 13-FIG. 15 illustrate a sequence of process steps for repairing a fracture.
Figure 14:
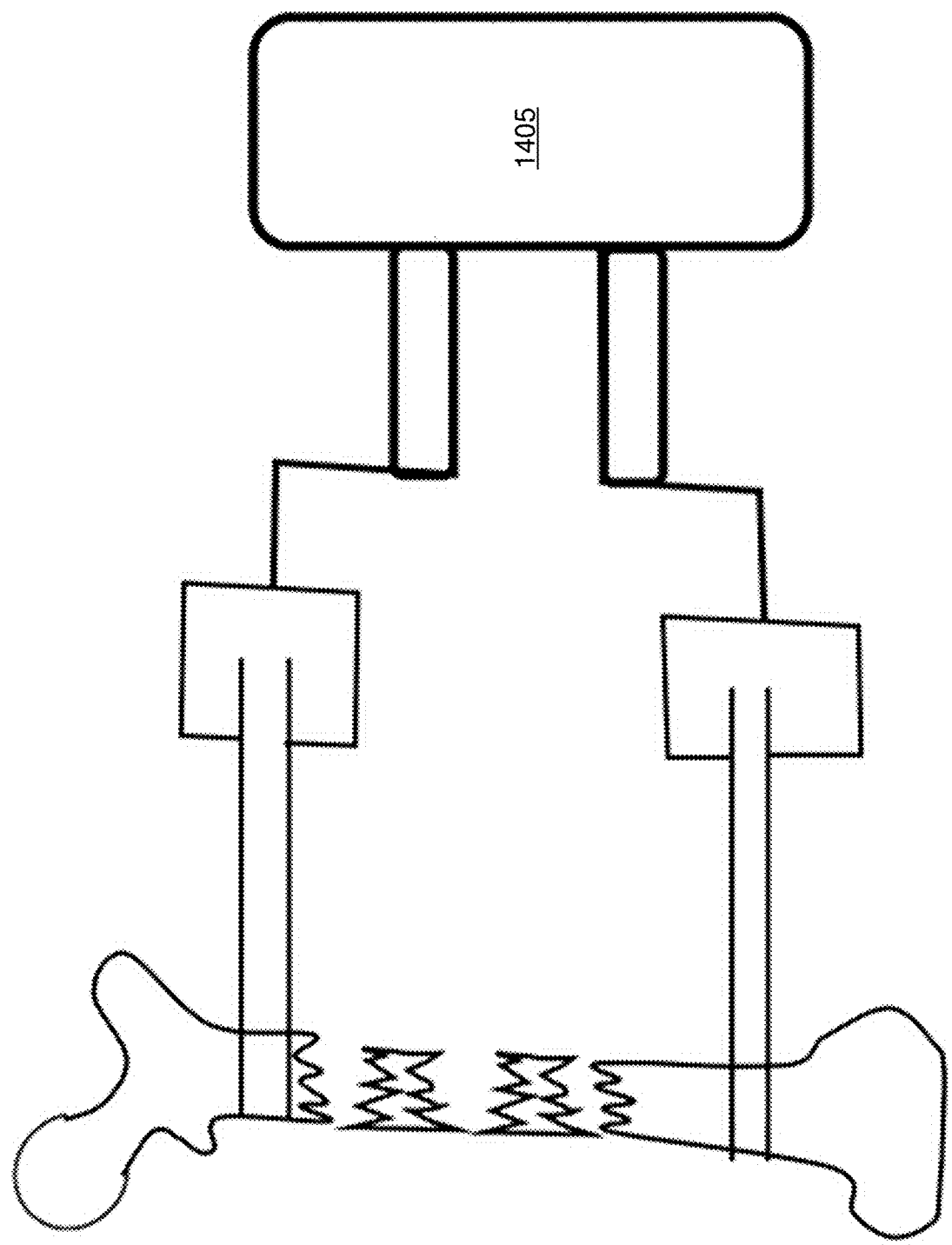
Figure 15:
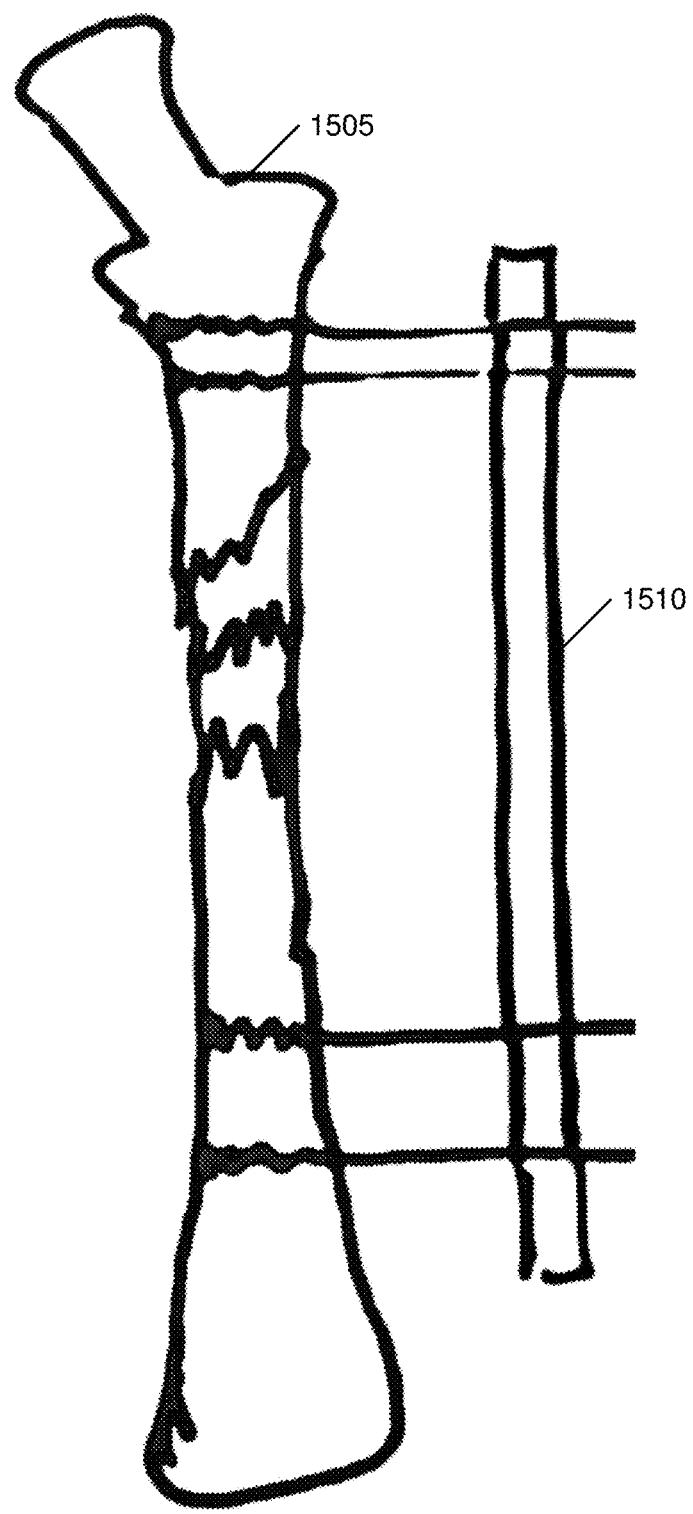

FIG. 13-FIG. 15 illustrate a sequence of process steps for repairing a fracture, FIG. 13 illustrates an acquisition of an image for robotic reduction; FIG. 14 illustrates a robotic reduction of a fracture of a long bone; and FIG. 15 illustrates use of an external fixator for securing a reconstructed long bone. In this process a long bone has been severely fractured. In some cases, it may be anticipated that serious injury to a bone may occur (e.g., a soldier deployed to a hostile area) and a CT scan may be prepared in advance and retained for use in an event that injury occurs. In FIG. 13, an advance CT image was not obtained so a CT image of a corresponding uninjured bone 1305 is obtained and a right-left reversal of the image produces a template 1310 for the fractured bone.

FIG. 14 includes a robot 1405 that uses template 1310 to reduce the fractured elements of long bone 1410. FIG. 15 includes the robotically reduced (per template 1310) long bone 1505 to which an exterior fixator 1510 is applied. Fixator 1510 includes an anisotropic and viscoelastic bar as described herein.

Current surgical fixation of fractures in orthopedic surgery has taken three forms, all of which have distinct advantages and disadvantages. As a matter of quick review, fracture fixation may include: (i) open reduction internal fixation; (ii) open or closed reduction and intramedullary rod fixation; and/or (iii) closed reduction external fixation.

A variety of these three fixation methods are generally used for fixation of long bones which includes femur, tibia, humerus, radius and ulna.

External fixation is primarily relegated to temporary initial fixation of open fractures which involve open wound contamination of bone from the outside world. These injuries generally preclude the use of metal inside or on bone, due to the fact that introduction of metal in open fractures would contribute to the development of deep infection and osteomyelitis. Therefore, external fixation of long bone fractures is almost never used as the definitive technique for long bone fracture fixation. Most often a high velocity fracture that is initially fixed with External fixation is "converted" to either internal fixation with intra-medullary rods or a plate and screws.

The main theoretical advantage of external fixation considered by orthopedic surgeons is its ability to stabilize the fracture without introduction of metal in the wound. Another very significant advantage of the external fixator is that it by no means disrupts the already compromised blood supply of the fractured bone. These theoretical advantages however have not been able to be exploited over the last 30 years because of a specific disadvantage of the external fixator, which specifically have to do with the material properties of the rods used in external fixation systems. These rods are extremely stiff constructs that categorically doom long bone fractures to non-union (non-healing). As discussed in this application, fractures commonly heal with a combination of enchondral (cartilaginous base) and intramemebranous (primary) bone formation. Motion at the fracture site results in healing primarily through enchondral ossification, whereas stability at the fracture site enables direct 'primary bone formation' through intramemebranous ossification.

The exact biology of fracture healing has yet to be elucidated, however, in general it is believed that too rigid or too flexible fixation, regardless of implant, leads to non-union or non-healing with the fracture site with new bone.

An embodiment of the present invention includes a system of fracture fixation that allows just the right amount of motion or "micromotion" which allows for rapid and progressive healing of the fractured bone with new healthy bone rather than with fibrous tissue.

Nature's fracture healing occurs in a sequence of biologic stages including inflammation, hematoma maturation, hypertrophic cartilage formation, new bone formation and remodeling to mature bone [Callus Formation]. Too little or too much ambient stress or stresses can disrupt this natural healing process.

Therefore, a theoretical advantage of external fixation of long bones, which is smaller and quicker surgery with minimal blood loss and minimal destruction of blood supply, has been overshadowed by its distinct empirical disadvantage of stiffness of the construct which leads to non-union. This may lead to underutilization of this external fracture fixation system.

Without use of external fracture fixation, orthopedic surgeons rely on other fixation systems/methods that clearly destroy the blood supply to bone primarily because these fixation methods are less stiff and do not doom the fracture to non-union.

Intramedullary fixation of long bones is one such technique which involves (a) reaming of the intramedullary canal and (b) placement of a metallic rod within the canal. Both of these actions destroy the endosteal blood supply of bone. Additionally, intramedullary fixation of long bone fractures places significant unwanted cardiopulmonary stress on an already injured patient due to production of fat emboli in the reaming and rod placement process.

Plate fixation of long bone fractures involves perio steal stripping, which destroys the external blood supply to bone. Plate fixation includes a plate construct that is generally more stiff than intramedullary rod fixation. Original techniques of rigid plate fixation used multiple screws that involved increased rates of non-union. These issues led to development of newer techniques of "bridging" plates, in which the plates are slid over the periosteum with minimal stripping and fewer points of fixation to bone with screws. This modification of plate fixation technique allows a more flexible construct that is less susceptible to non-union and has gained widespread acceptance.

Figure 16:
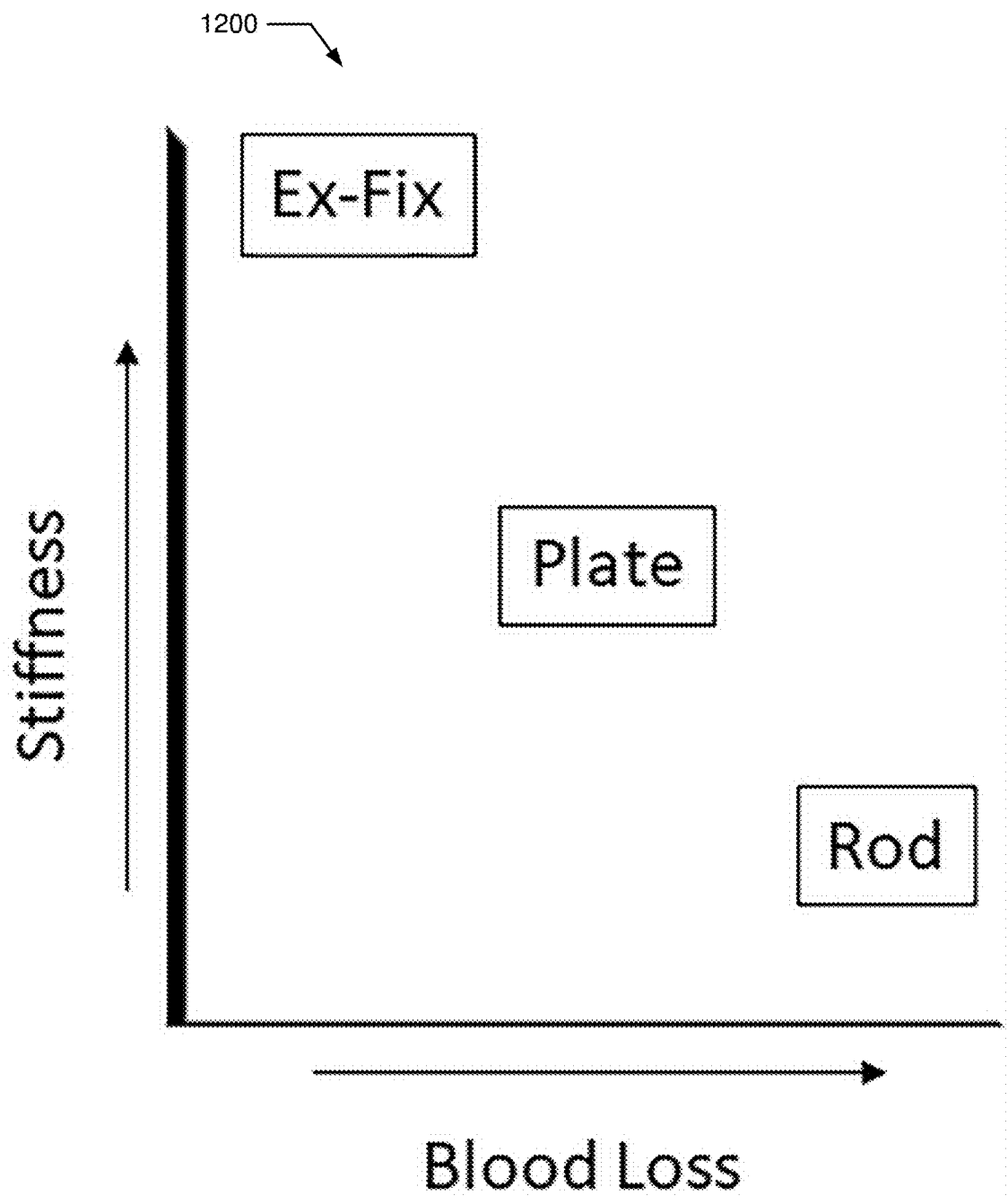
FIG. 16-FIG. 18 illustrate a relationship between a rigidity of a fixator construct and blood loss typically associated with three types of surgery.
Figure 17:
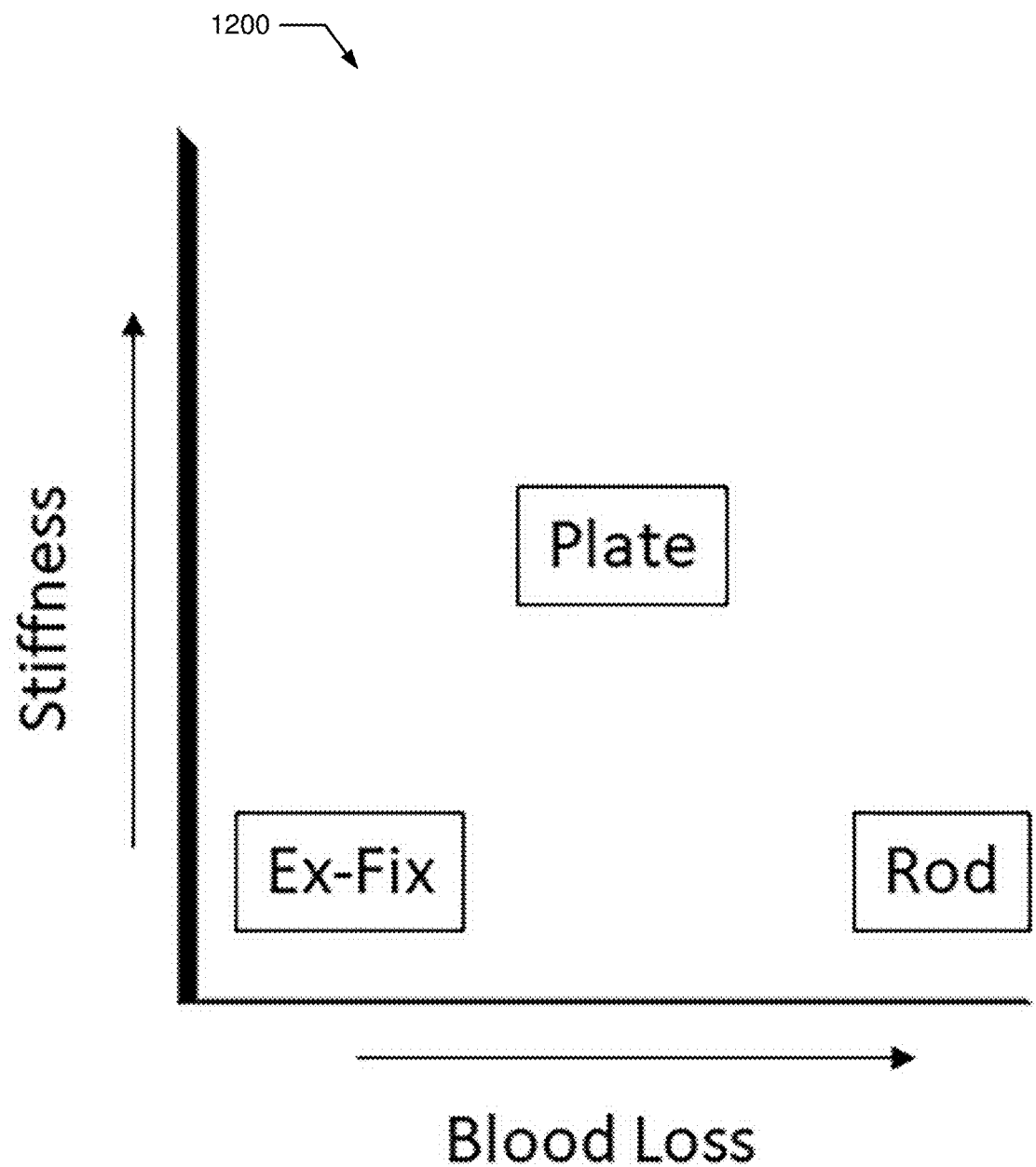
Figure 18:
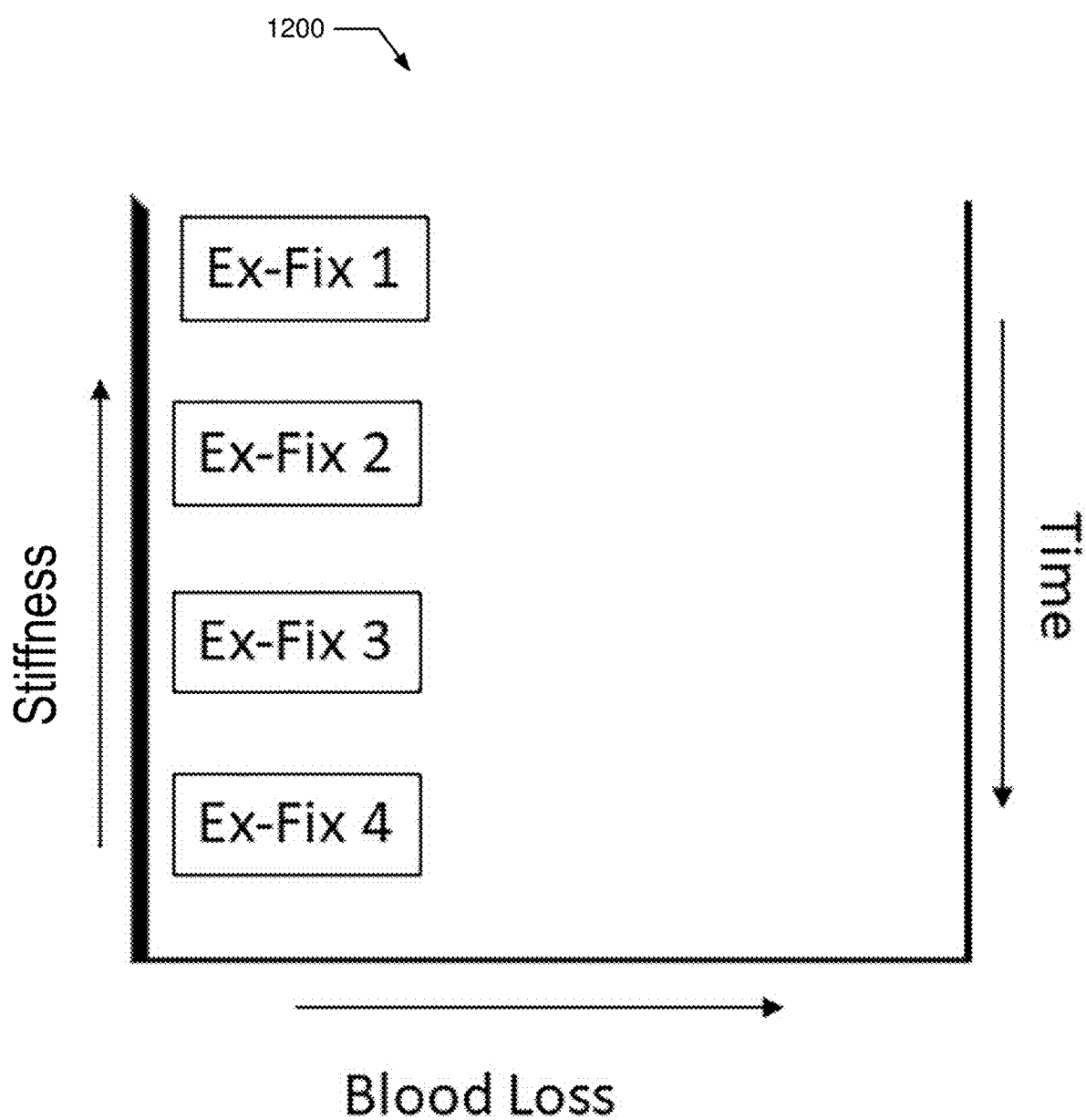

FIG. 16-FIG. 18 illustrate a relationship between a rigidity of a construct and blood loss typically associated with three types of surgery: (a) external fixator, plate fixation, and intramedullary rod. FIG. 16 illustrates that external fixators to be the stiffest construct and associated with the least amount of blood loss or surgical dissection. FIG. 17 illustrates an external fixator that is made less stiff than plates and rods due to a change in material properties of a rod used in external fixation. FIG. 18 illustrates an external fixator that includes a capacity to change/adjust its stiffness properties over time. For example, the fixator may be very rigid initially and progressively become less stiff, allowing progressive exposure to varying levels and/or combination of stresses including tension, compression, torsion, bending and shear.

An embodiment of the present invention may include a system and method allowing modulation and control of stiffness properties, a time-varying stiffness profile (including an elastic modulus and Poisson's ratio) of a fixation system that may be manipulated over time to produce varying levels and types of stress to healing bone. Such a system may reverse an early disadvantage of external fixation systems (stiffness), and on top of that produce an advantage that may not be immediately available to plate and intramedullary rod fixation since these methods do not allow easy and frequent exchange of a construct spanning the fracture site.

Reduction of the fracture: one difficulty in fracture fixation of long bones, especially lower extremity long bones that are covered with strong muscles, includes obtaining a "reduction". To obtain a proper reduction, fragments of a fracture are placed in close to anatomic alignment or at least in acceptable mechanical alignment, before any kind of spanning permanent fixation is applied with plates, rods or fixators.

The process of obtaining a reduction is itself a difficult process employing significant force and traction apparatuses with a variety of reduction maneuvers by the surgeon. This method of fracture reduction, which involves placing the patient on a fracture table and applying ever increasing levels of traction to the leg through a post placed in the groin and pushing and pulling on the leg with a crutch, is itself arcane and does not take advantage of available robotic technologies which can be much more precise in producing the proper amount of force for fracture reduction.

In an incorporated priority application, a method is described for obtaining reduction using robotic machines. Current robotic techniques are either image based, or non-image based. Image based robotics use radiography or computed tomography to obtain a virtual plan of the patient's bone. In the operating room the patient's bone is registered and matched with the virtual plan already in the software. In this manner the robotic and navigation systems have the ability to know the exact position of patients bone the operating room space.

In an incorporated priority application, it was suggested that in high velocity trauma, whether in motor vehicle accidents or in injured warriors, athletes, or other high-risk individuals, a CT or X-ray of the uninjured bone (for example the contralateral femur) be obtained. Subsequently through a software program, a three-dimensional computer model of the imaged bone be created and then reversed to be used as a template for reduction of the injured bone. Through this process the fractured extremity could be reconstructed by application of Schanz screws to proximal and distal fragments of the fractured bone, and subsequently attaching the Schanz screws to the proximal and distal arms of a robotic tool. The robotic system would then produce just the proper amount of traction and force to reduce (approximate) the broken bone pieces to the closest approximation of the virtual template obtained through the mirror image process. Some individuals, particularly high-risk individuals such as deployed soldiers, first responders, athletes, and others, may predefine (such as pre-imaging) certain body structures with information to enable rapid and accurate reduction. For example, periodic or pre-deployment data may be prepared and stored in an event that reduction, particularly for extreme bone fracturing, is desired.

The same process of producing a reverse template can also be accomplished through image free navigation systems. For example, the non-injured femur of a patient can be registered in the OR space using optical or infrared tracking technology. Reference trackers and frames are used to locate and register the un-injured limb in the OR space, after which a with the use of existing human anatomy data sets, a three-dimensional computer model of the patient's femur is created and reversed.

Ultimately image based and image free robotic systems can produce a three-dimensional computer model of the patient's un-injured extremity and reversing the image to produce a template for the injures extremity. A robotic tool could then produce a reduction maneuver without excessive force, where the initial external fixation rods are applied. The surgery can be completed within a fraction of what is currently required to fix a traumatic long bone fracture (for example, 30 minutes instead of 3-4 hours).

Subsequently rods of differing material properties are exchanged for the external fixation system in clinic to expose the fracture to varying and progressive levels of stress (as well as combination of stresses, e.g., more compression and bending and less torsion and shear) conducive to fracture healing.

Option 1. anisotropic rods—an earlier patent application, U.S. application Ser. No. 15/458,586, now U.S. Pat. No. 10,299,930, hereby expressly incorporated by reference, proposes variable material properties prosthesis such that a graded non-homogeneous prosthesis has a tendency not to stress shield and or bone resorb in order to allow optimal osteointegration of a prosthesis. Another earlier application, U.S. application Ser. No. 15/234,927, hereby expressly incorporated by reference, proposes a multi-dimensional stiff prosthesis with ribs and planks with a built-in propensity for insertion into bone when exposed to a driven vibratory motion. Subsequent papers discussed a combination of variable material properties prosthesis with multi-dimensional stiffness (ribs and planks), which produces a prosthesis that has a bias for insertion, does not bone resorb or stress shield, and resists fracture at cellular junctions of a graded non-homogenous prosthesis.

In an embodiment of the present invention including a robotic fracture fixation with external fixators, once a difficult process of reduction is achieved, such as with a robotic tool, the embodiment may include system and method of rod exchange of varying material properties, over different time periods, to allow progressive exposure of bone to stress and specifically different combination stresses to stimulate bone healing.

For example, current knowledge about an optimal level of stress and micromotion for fracture healing is lacking and non-existent. An embodiment may include a development of a set of anisotropic rods for external fixation of long bones. These rods can be metallic or composite. They allow differing levels and types of stress to be transferred to a stabilized fracture. A stabilized fracture may then be nursed progressively with increasing levels of stress to a rapid healing process. For example, it is likely appropriate to have rigid fixation of a fracture for the first three weeks for pain management and to allow soft tissues to stabilize, however, after the first three weeks, rigid fixation maybe detrimental to callus formation. Slow and progressive compression at the fracture site that occurs over three months may be ideal to fracture healing. In that scenario the external fixation rods can be simply exchanged, in clinic, with rods that remain stiff in bending, shear, torsion and tension but allow progressively more compression, such that the rods elastic modulus in compression becomes progressively lower and lower over the time of fracture healing. The time periods are representative, with different values for the initial rod stiffness and duration, and installation periods of subsequent external rods, may include differing appropriate values.

Any combination of the anisotropic material properties can be accomplished. For example, it may be discovered that at 6 to 8 weeks addition of increasing bending and torsional moments and are beneficial to fracture healing. This particular anisotropic rod (metallic or composite) can be made and used at the proper time through a simple exchange process in clinic.

The biology of fracture fixation and the optimal stresses required for fracture healing continues to improve but is not yet completely elucidated. However, once an accurate model or formula is known, model-compliant external fixators can become the fracture fixation of choice for long bone fractures using the model to determine the material properties and installation/application durations for specific rods in this set of rods. At that point external fixation of long bone fractures with reduction (direct or indirect visualization or robotic reduction) will not only perform the surgery with less mechanical and surgical trauma but also the anisotropic rods allow just the right combination of stresses to be transferred to the fracture site over time for optimal and rapid healing.

Some examples of anisotropic rods that may be used in the set of rods may include variations of a structure such as the intramedullary nail described in the U.S. patent application Ser. No. 15/406,752, expressly incorporated herein by reference thereto (e.g., an intramedullary (IM) nail with ribs and planks). That particular IM nail includes ribs that are more flexible and planks that a more rigid, such as inspired for the purpose of undulatory motion where an applied energy to the longitudinal axis of the nail tends to propagate longitudinally as opposed to being dissipated radially. For the process of fracture fixation with external fixation, such rods can be created with a smaller number of planks (rings) which would make the rod less stiff in compression, or alternatively the planks can be created as half or ¾ planks in various arrangements within the foundation of the rod, which may make the rod more flexible in bending. The ribs can be placed in a helical pattern, which may produce a rod that is more flexible in torsion. Any combination of ribs and planks within the foundation of the intramedullary nail will change its mechanical and material properties. These anisotropic rods can then be conveniently exchanged in the clinician's office at various times during fracture healing process. Finally, for fractures that are at risk of non-union addition of vibration in subsonic and ultrasonic forms to the rod, which is then transferable to the fracture site, can be utilized as a stimulus to induce rapid bone formation.

Figure 19:
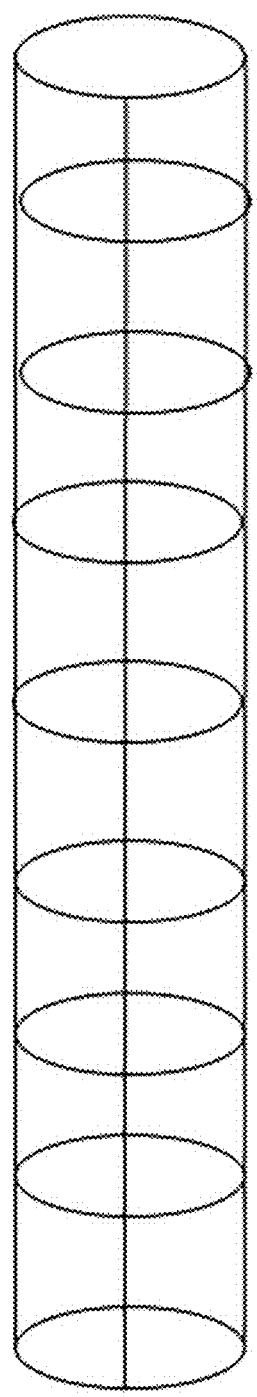

FIG. 19-FIG. 23 illustrate various anisotropic rods that may be use for external fixation of long bone fractures. FIG. 19 illustrates an anisotropic rod for external fixation including a set of orthogonal stiffness structures, including a number of longitudinally extending stiffness structures (e.g., ribs) and a series of circumferential parallel stiffness structures (e.g., planks) perpendicular to the longitudinal stiffness structures, these structures disposed within a foundation of the rod or on a surface of the foundation. The same foundation with a different arrangement of stiffness structures exhibits different material properties of the rod as described herein (e.g., bending, torsion, and the like). The stiffness structures in cooperation with the foundation producing a desired stiffness profile for the rod.

Figure 20:
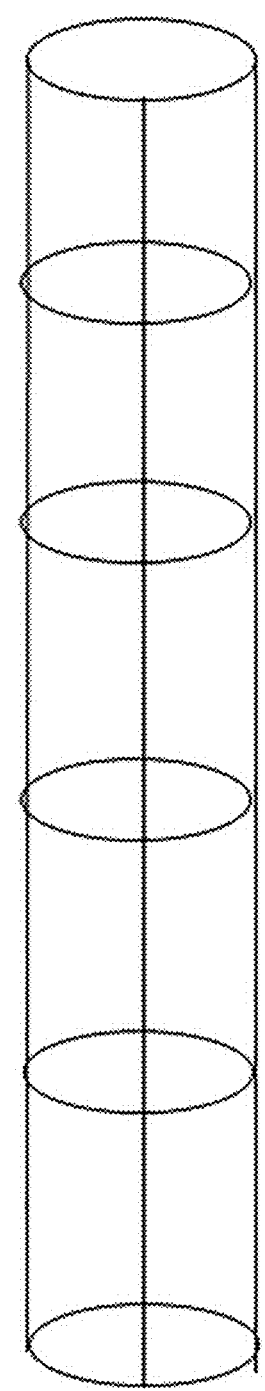

FIG. 20 illustrates an anisotropic rod for external fixation similar to FIG. 19, including a different number of longitudinally extending stiffness structures (e.g., ribs) and a series of circumferential parallel stiffness structures (e.g., planks) perpendicular to the longitudinal stiffness structures, these structures disposed within a foundation of the rod or on a surface of the foundation. The stiffness profile of the rod in FIG. 20 may be different from the stiffness profile in FIG. 19, responsive to the different arrangement of stiffness structures.

Figure 21:
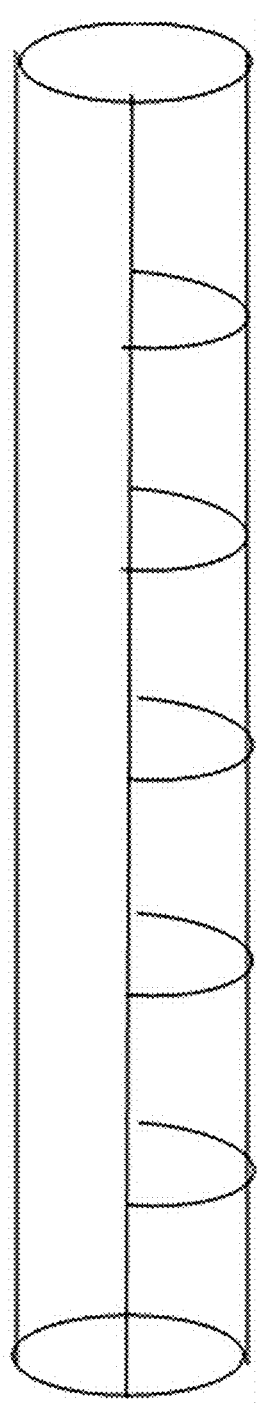

FIG. 21 illustrates an anisotropic rod for external fixation similar to FIG. 19 and FIG. 20, including a different arrangement of longitudinally extending stiffness structures (e.g., ribs) and a series of circumferential parallel stiffness structures (e.g., planks) perpendicular to the longitudinal stiffness structures, these structures disposed within a foundation of the rod or on a surface of the foundation. The stiffness profile of the rod in FIG. 21 may be different from the stiffness profile in FIG. 19 and FIG. 20, responsive to the different arrangement, shape, and, disposition of stiffness structures (e.g., the "planks" extend partially through a thickness of the rod).

FIG. 22 illustrates an anisotropic rod for external fixation similar to FIG. 19-FIG. 21, including a different arrangement of orthogonal stiffness structures (e.g., a set of counter-rotational helical stiffness structures), these structures disposed within a foundation of the rod or on a surface of the foundation. The stiffness profile of the rod in FIG. 21 may be different from the stiffness profile in FIG. 19 and FIG. 20, responsive to the different arrangement, shape, and, disposition of stiffness structures (e.g., the set of counter-rotational helical structures).

FIG. 23 illustrates an active anisotropic rod 2300 which may include a configuration similar to rods of FIG. 19-FIG. 22, or other arrangements of stiffness structures. Rod 2300, in contrast to the passive anisotropic rods of FIG. 19-FIG. 22, may include one or more motion drivers, such as a subsonic driver 2305 and/or an ultrasonic driver 2310. Motion from the motion drivers may assist with the healing of a bone fracture when used in an external fixation solution.

Robotic Materials

Recent advances in manufacturing combined with miniaturization of electronics has enabled a new class of materials termed "robotic materials" that far transcend classic composite material in functionality. Current state of the art allows composites to be integrated with sensors and actuators at high densities, and in combination with small microprocessors the robotic materials can function autonomously. With further advances in material science, computer science, distributed algorithms and manufacturing processes composites can integrate sensing, data collection and actuation with higher levels of self-governing functionality. Robotic materials can enable smart composites to autonomously change their shape, stiffness and physical appearance in a fully programmable way. For example, current technology exists that enables airplane wings to adapt their aerodynamic profile due to varying stresses in the environment. Integrating sensors and actuators into composites is becoming increasingly common, and with further advances embedded computation and communication will become more common place. Materials that self-diagnose, and self-repair are ubiquitous in biological systems, some of which can adapt to changing loads such as human bone or trees that can grow additional roots to accommodate changing load requirements.

This concept is particularly attractive for rods used in external fixation of fractured long bones of humans. As discussed earlier the main disadvantage of the external fixation systems has been the fact that they are extremely rigid. Titanium, cobalt chrome, and stainless both of which are commonly used for external fixation rods are five and ten times more stiff than human cortical bone respectively. Given the fact the there is a significant value proposition of minimal dissection and blood loss with more rapid and reliable healing of long bones, it may be a favorable trade-off to produce smart composite rods with increased functionality with sensing, actuation and computation functionality for external fixation systems in order to eliminate nonunion of long bones and barbaric open surgeries with extensive blood loss and negative cardiopulmonary impact on already physiologically compromised patients.

Smart materials were made possible by development of microelectromechanical systems MEMS, which then allowed for manufacturing of microscale structures with the same processes that are used in conventional analog and digital semiconductor circuits, permitting their tight integration within composites.

Robotic material integrates dedicated sensors that in combination with appropriate signal processing, let the composite identify and respond to the environmental patterns.

Actuation refers to changing the material properties of the underlying base material. Some possible actuations are expanding, contracting, changing stiffness, changing surface texture, or changing color. One common approach for a variety of variable stiffness actuators is sandwiching a thermoplastic between two metals plates and then exploiting the thermoplastic's change in stiffness with increasing temperature. When the thermoplastic is at low temperature, the metal palates are tightly coupled together, acting as a single stiff composite. At higher temperatures, the thermoplastic has much less resistance to shear and the plates act as if they were uncoupled from each other, creating a composite with much lower stiffness. Similar functionalities can be accomplished with shape memory polymers and particle jamming techniques.

Local computation is accomplished through local algorithms, where from a computational perspective, robotic materials may be viewed as amorphous or spatial computers, which attempt to formalize a distributed computation model for systems that are limited to local communication and limited computational resources at each node. In the future a key challenge in amorphous computing is how to design local integrations so that a desired global behavior can emerge.

Local communication requires embedded communication not only to transport sensing and control information but also for more complex spatial dynamics to occur. Local computation in robotic material s offers not only local preprocessing of sensing information but also the routing of information through a computer network, such aa s a shared communication channel that is arbitraged by all participants of the network, a problem that has been widely studied in sensor networks.

Sensing, actuation, computation, and communication and power infrastructure can be integrated into composites at high densities in a scalable fashion. Instead of silicon-based computation, robotic materials could also perform computation using polymer electronics.

Robotic material require control at two different levels: (i) local control of each actuator using feedback from appropriate sensors, and (ii) global control that implements a desired spatiotemporal pattern across the material either in a distributed or centralized manner.

In summary robotic materials are a new class of multifunctional materials that are enabled by recent advances in material science, electronics, distributed computation, and manufacturing. Although composites now include the ability to sense damage and self-repair, none of the state-of-the-art composites fully integrate sensing, actuation, computation and communication.

From the standpoint of long bone fracture fixation in humans, robotic materials hold great potential. External fixation of long bone fractures is the least invasive procedure. Reduction of the fracture may be automated with image based and image free robotic navigation systems. Fracture healing can be dramatically augmented with use of programmable robotic material used as smart composite rods that can enhance fracture healing in a much more substantial way that is imaginable with current techniques.

Figure 24:
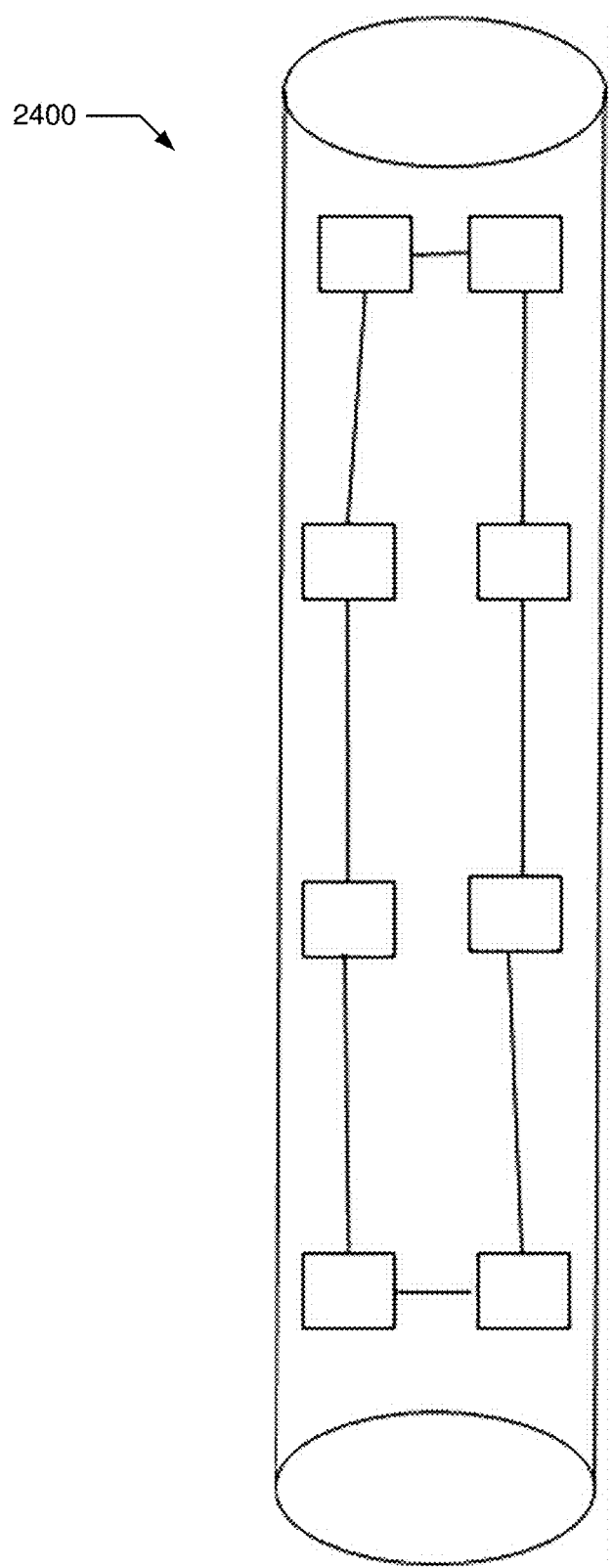
FIG. 24 illustrates an anisotropic rod that may be used in an external fracture fixation solution, rod may include a robotic material or construction with sensing, actuation, computation and communication.

For example, robotic material used for external fixation rods can be preprogrammed to progressively vary their stiffness over a period of 3 months or to progressively allow more bending and or torsional stresses to the healing bone. That progression may not be monotonic or uniform but may vary based upon various biologic (healing status) or environmental factors (e.g., time of day, activity level). Robotic material can be embedded with mechanical sensors that measure applied force, strain and deflection, as well as accelerometers and Inertial measuring units IMUs that detect impacts and orientation with respect to gravity, all of which can be used to access the process of fracture healing. For example, certain robotic material rods can be embedded with "variable stiffness actuators" that progressively decrease compressive stiffness of the rod, while other robotic material rods can be incorporated to assess sense strain and stress being experienced at the fracture site. In this manner a programmable "load sharing" construct can be created to properly allow increasing levels of stress and stimulation necessary for a healthy robust healing process FIG. 24 illustrates an anisotropic rod 2400 that may be used in an external fracture fixation solution. Rod 2400 may include a robotic material or construction with sensing, actuation, computation and communication, generally illustrated as the interconnected network of functional elements collectively implementing the external fracture fixation solution. Rod 240 may include discrete circuit boards, wiring and structural material embedded into a composite form producing the dynamically variable stiffness profile for rod 2400.

An embodiment of the present invention discusses use of replaceable anisotropic rods for external fracture fixation because other fixation methods may not be as conducive to easy replacement and substitution, over time during the healing process, of a fixator component having varying stiffness profiles. Internal rods, or fixation plates, based on current techniques and solutions, do not allow easy or risk-free substitution as surgery is required for replacement/ substitution of such solutions.

Robotic materials may be embedded into an intermedullary channel as an intramedullary rod that does not need to be removed. As well, plates usually utilized for open reduction internal fixation can be constructed from robotic material which would then allow custom adjustments of the anisotropic behavior of the plate (or IM rod) based on the needs of the healing fractured bone at various points in time. because the stiffness profile may be adjusted without removal from the channel, including pre-programmed variations or remotely directed (e.g., wireless) variations in stiffness profiles.

Another solution for embedded anisotropic fixator components may include use of dissolvable/reabsorbable stiffness structures used in cooperation with non-dissolvable/ absorbable structures. Such anisotropic fixators may include a subset of stiffness structures disposed within the foundation of the device, and another subset of stiffness structures disposed on a surface of the foundation. Some or all of the surface stiffness structures may be dissolvable/absorbable when installed into location. Over time, the degradation of the dissolvable stiffness structures changes the stiffness profile similar to the changes resulting from periodic replacement of rods in external fixation solutions. In this way, benefits of varying stiffness profiles for internal fixator constructs may be available as different options for the surgeon.

Dissolvable or reabsorbable materials are used in biodegradable materials for bone repair purposes. The choice between using degradable and non-degradable devices for orthopedic and maxillofacial applications must be carefully weighed. Traditional biodegradable devices for osteosynthesis have been successful in low or mild load bearing applications. However, continuing research and recent developments in the field of material science has resulted in development of biomaterials with improved strength and mechanical properties. Such materials are designed to be completely biodegraded and absorbed into the body.

Embodiments of the present invention include implementations in which the structure includes absorbable/degradable and non-absorbable stiffness structures. The degradation over time is predesigned to change the stiffness profiles of the fixator in a predetermined manner so that the varying stiffness profile improves bone healing, especially as compared to an unchanging stiffness profile or a randomly changing stiffness profile that results from unplanned or undirected degradation.

As discussed above regarding replacement/substitution of anisotropic rods having varying stiffness profiles, the incremental changes in the stiffness profiles over time during the healing time frame improves bone healing as compared to fixators with non-varying stiffness profiles. Various models and bone-healing biology may define one or more local optimizations that may be implemented by, influenced by, controlled by, or otherwise defined by varying a stiffness profile of a fixator construct in a particular way during the healing process. The substitution/replacement of anisotropic structures over time corresponding to such a model improves the healing of the bone. The anisotropic structures may be periodically changed to approximate the model. The degradable fixator changes constantly and more gradually without a requirement of clinic visits and may more closely track the model.

Degradable materials for engineering use in dentistry and orthopedics continue to develop. A reference describing some aspects of such materials is provided in Z. Sheikh et al., "BIODEGRADABLE MATERIALS FOR BONE REPAIR AND TISSUE ENGINEERING APPLICATIONS" Materials (Basel) 2015 Sep. 8(9)—published online 2015 Aug. 31, 5744-5794, this reference hereby expressly incorporated by reference thereto in its entirety.

There is a widely held belief among some that the mechanism of taper corrosion is best characterized as mechanically assisted crevice corrosion. Fretting initialized crevice corrosion in tapers is a complex problem and the severity is likely dependent on multiple factors. Corrosion has been associated with clinical complications, such as elevated metal ion levels, persistent pain, tissue damage, and early implant failure.

Some common causes related to failure include the recent use of large femoral heads which influence torsional forces at the trunnion/taper interface and use of shorter and more flexible trunnions (inspired to enhance motion and decrease instability). Modern prosthetic designs tend to have shorter and slimmer trunnions. This is thought to increase the impingement free range of motion by reducing the trunnion skirt. This does however mean that the base of the trunnion now sits very close to the taper, which may lead to an increase in edge loading at the trunnion base. In addition, the slimmer and smaller diameter taper means that the surface area of contact between the taper and the trunnion is less. This may reduce the chance of a successful interference fit and thus increase the potential for micro motion and fretting.

Certain solutions have been proposed to address this problem including the use of ceramic heads, which have mitigated the metal corrosion, however, use of ceramic femoral heads has not eliminated metal corrosion from the head-neck taper. This fact points out other mechanical factors that may be significant in this problem, including the "taper impaction technique" and "engagement of the modular taper interface".

Figure 25:
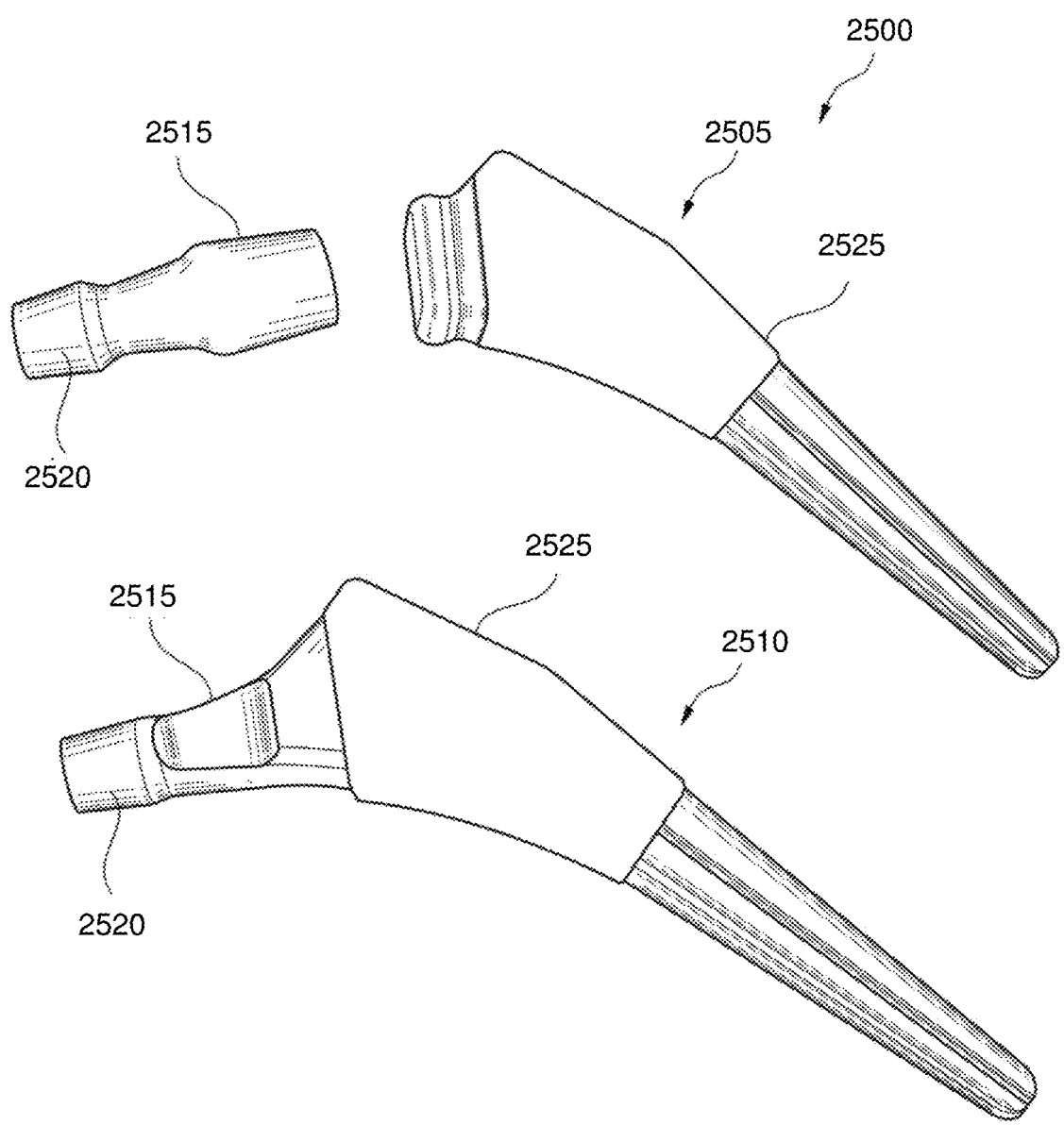
FIG. 25 illustrates a modular prosthesis assembly in both an unassembled mode and an assembled mode.

FIG. 25 illustrates a modular prosthesis assembly 2500 in both an unassembled mode 2505 and an assembled mode 2510. Mode 2505 illustrates two components of assembly 2500: a neck 2515 which includes a trunnion 2520 and a body 2525 (sometimes may be referred to as a stem in specific assemblies 2500).

Figure 26:
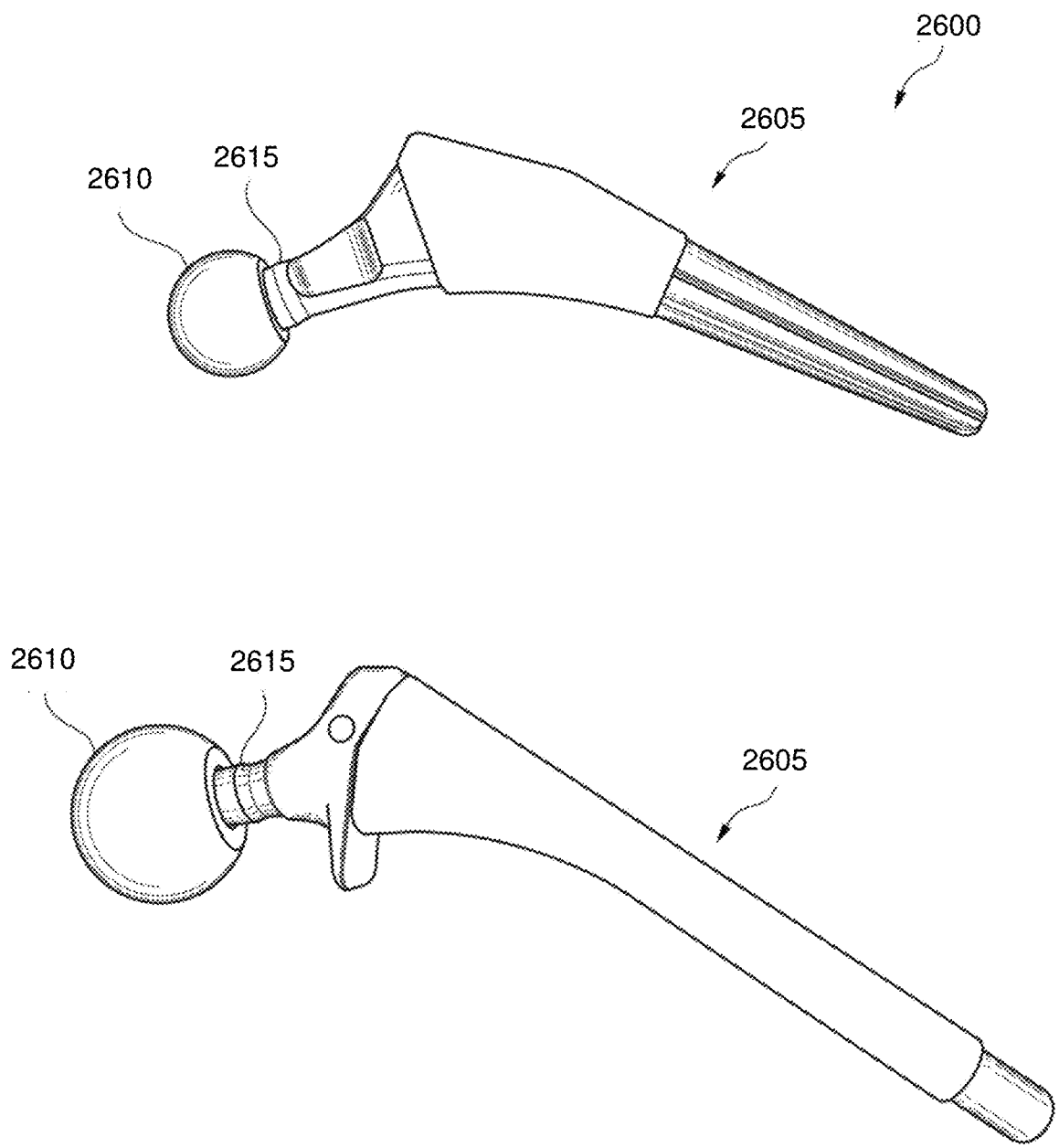
FIG. 26 illustrates a set of representative modular prosthesis assemblies in the assembled mode including a ball head portion.

FIG. 26 illustrates a set of representative modular prosthesis assemblies 2600 in a completely assembled mode 2605, each assembly 2600 including a head 2610 mechanically joined to neck 2515 using trunnion 2520 engaging an aperture (not shown) in head 2610. The different assemblies 2600 illustrate different dimensional parameters for the components of each respective assembly.

Taper locking for fixing a modular ball head onto the metal stem in total hip arthroplasty (THR) has been introduced more than 30 years ago and is now the solely used design concept of modern modular hip systems. For that purpose, the male stem taper as well as the female head taper use similar taper angels achieving close contact of the components and strong interlocking forces. Since all manufacturing processes underlie deviations within their tolerance regime, it is nearly impossible to create ball head and stem tapers of identical taper angle, which could create a so called "line to line contact" of the components. Instead, assuming those small differences of the taper angles, the initial contact of the components will always occur at one clear end of their tapers-at the proximal end, if the stem taper is smaller than the head taper (negative mismatch), and at the distal end if the stem taper is larger than the head taper (positive mismatch).

Figure 27:
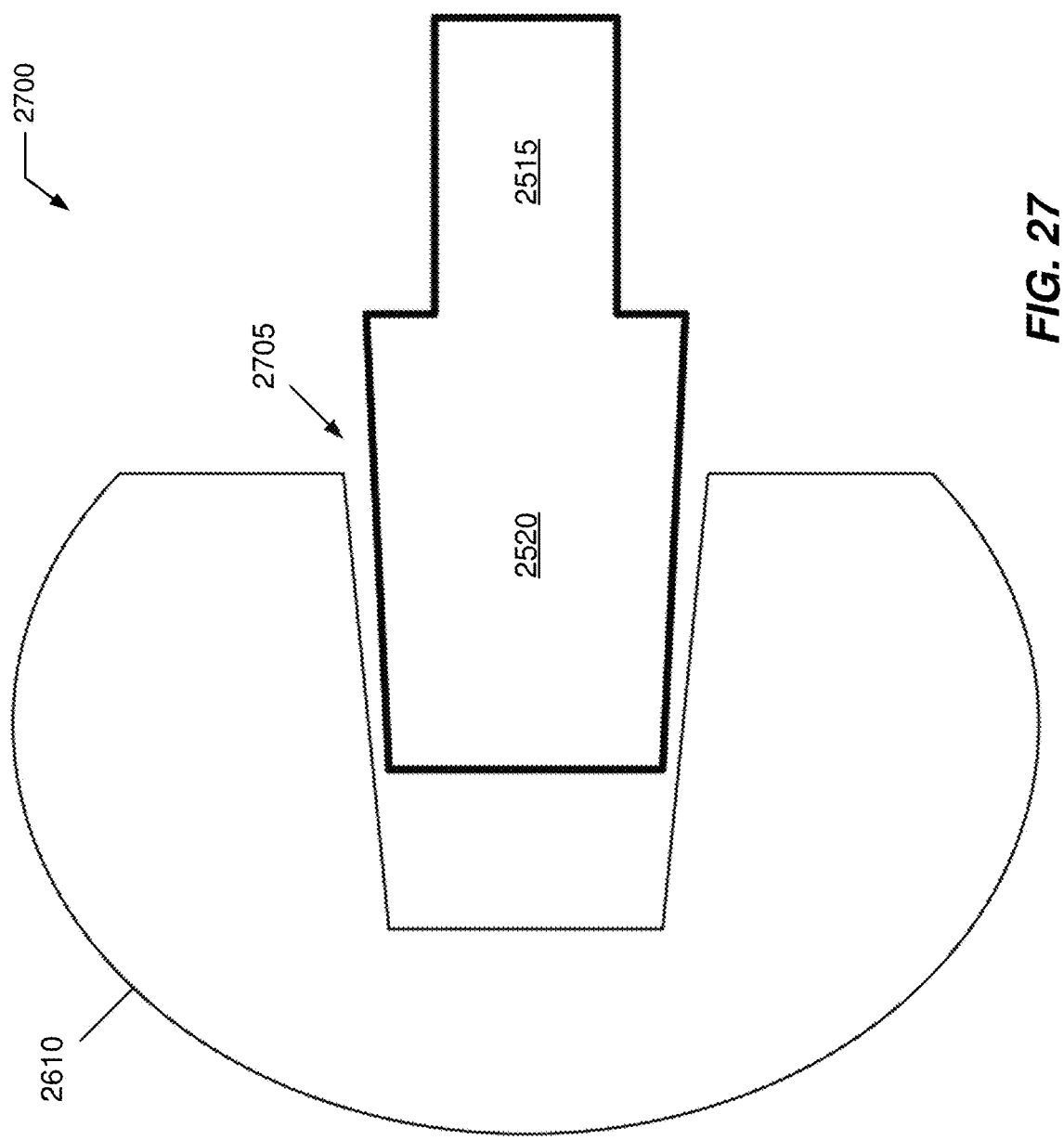
FIG. 27 illustrates a negative mismatch of a taper joinder for an assembled prosthetic assembly.

FIG. 27 illustrates a mechanical coupling portion 2700 of an assembly 2600 in which there is a negative mismatch of a taper joinder. Head 2610 includes an aperture 2705 that, ideally, would have a taper of the interior receiving surface that would be a very close match with a taper of an exterior mating surface of trunnion 2520. The taper joinder is the mechanical coupling of the interior surface and the exterior surface.

Figure 28:
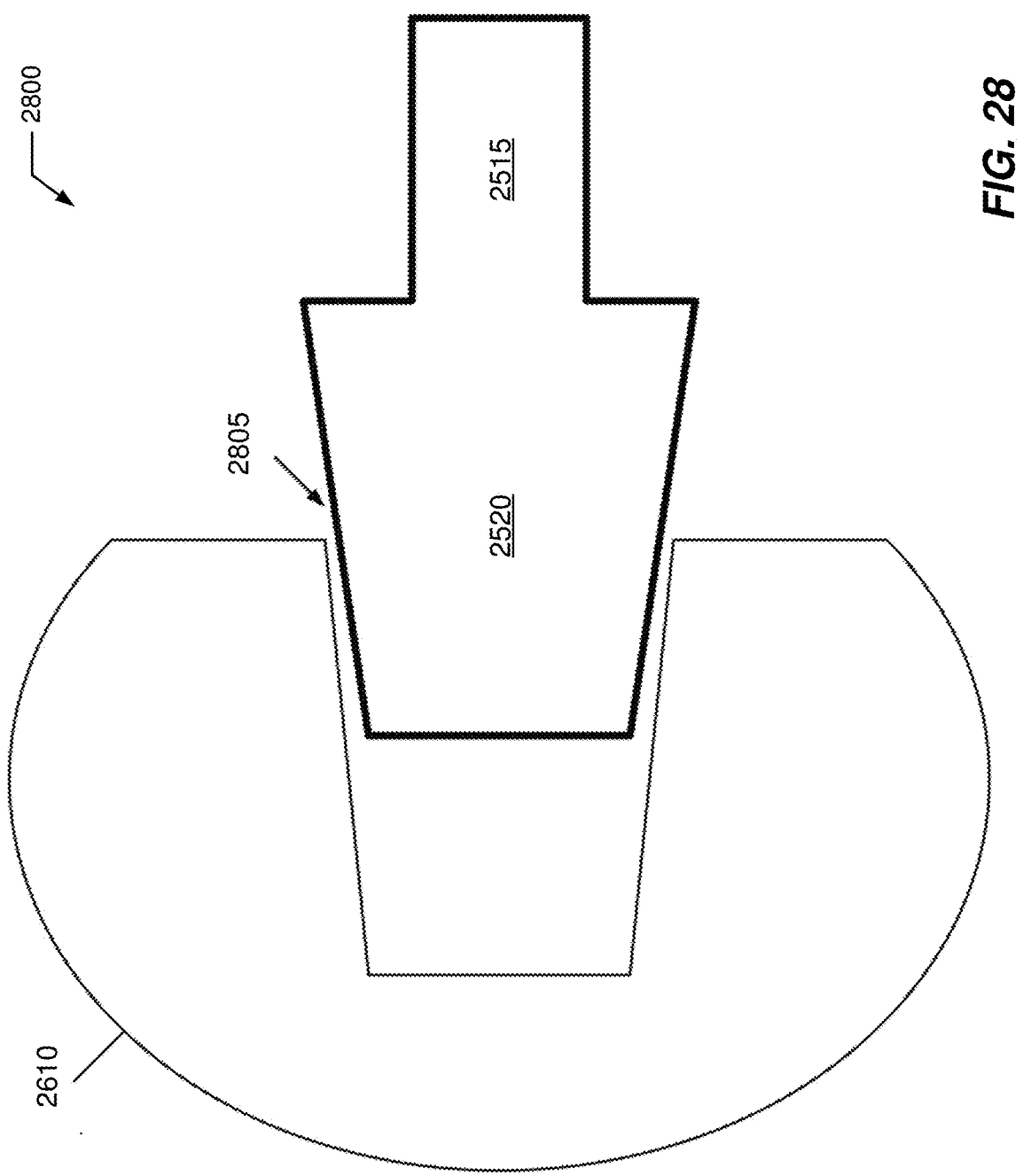
FIG. 28 illustrates a positive mismatch of a taper joined for an assembled prosthetic assembly.

FIG. 28 illustrates a mechanical coupling portion 2800 of an assembly 2600 in which there is a positive mismatch of a taper joinder. Head 2610 includes an aperture 2805 that, ideally, would have a taper of the interior receiving surface that would be a very close match with a taper of an exterior mating surface of trunnion 2520. The taper joinder is the mechanical coupling of the interior surface and the exterior surface.

Figure 29:
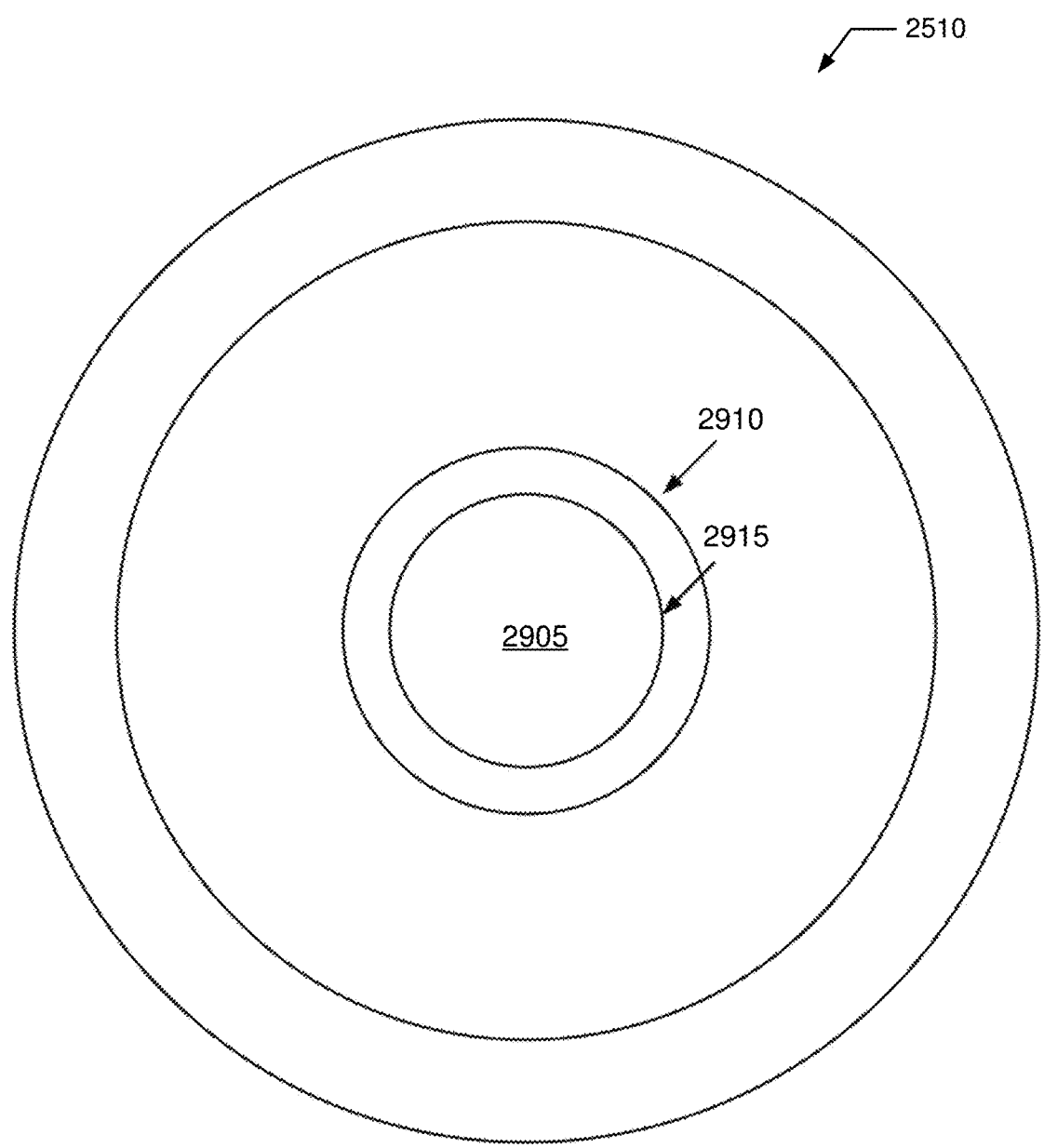
FIG. 29 illustrates a plan view of a joinder opening in a head for a prosthetic assembly.

FIG. 29 illustrates a plan view of a head 2610 including an aperture 2905. Aperture 2905 includes an opening 2910 that narrows to a termination 2915, with the taper depending upon a depth of the aperture 2905 and a difference between radii of opening 2910 and termination 2915. A mismatch depends upon a relationship of this taper to the taper of a mating trunnion 2520 inserted within aperture 2905.

It is also possible to define head and stem taper angel (mean and tolerance) in such a way that their difference is positive or negative over the whole tolerance field. In that case, the initial contact of the components will always occur at the same taper end, leading to an angular gap of deviating size between the components always opening into the same direction. An inevitable property of head-taper junctions is the occurrence of micro-motion, so called fretting, within the angular gap under alternating loads which can reach nine times the body weight. These micro motions include reversible and irreversible closing and opening movements of the angular gap, increasing and decreasing the contact area, and sliding movements of the component taper surfaces along the taper axis. Mechanical stresses subsequently induced in the components at and below the surface are compression, tension, and shear stresses. Besides mechanical stresses there may also be physio-chemical interactions of the surfaces and materials considering the fluid, water-containing environment in the human body. Fretting corrosion is related to relative interface shear motion and fluid ingress, which may vary with contact force and area. Some have hypothesized that assembly forces modify the extent and distribution of the surface contact area at the taper surface interface. Increased assembly forces could generate sufficient friction resistance at the interface to prevent local fretting and may also improve sealing of the interface and limit fluid ingress. Design factors that may modulate this interaction are material and geometry of the taper heads. Both surface design and assembly force thus seem to play a role in corrosion patterns by influencing contact pressure and relative motion.

Specific weaknesses with the current design for modularity may include two factors, which involves the use of the Morse taper. The first factor involves the method of impaction in the operating room. The taper mechanism has a positive or negative mismatch by design. The surgeon typically bangs on head 2610 with a plastic tamp to implant head 2610 onto trunnion 2520. Force is a vector with both a magnitude and a direction. The surgeon has no way to precisely and repeatably control either the magnitude or the direction of these forces. The method of impaction of head 2610 on to trunnion 2520 (or neck 2515 on to body 2525) is very crude. It is highly likely that since the force imparted is not applied co-axially, that the torsional forces created by use of the mallet and tamp produce an asymmetrical fit of the head (bore) on the trunnion. These phenomena create surface contact between the head and the trunnion that is asymmetrical, leading to: 1) instability, increased micro-motion, and fretting, and 2) increased contact stresses leading to loss of protective metal-oxide film referred to as passivation. These factors collectively lead to "mechanically assisted crevice corrosion" and thus are believed to be less desired. Some embodiments of the present invention may include a method of impaction of head 2610 onto trunnion 2520 using an improved technique. Some embodiments may include a prototype to allow quantifiable delivery of force in a coaxial fashion.

The second factor with the Morse taper as a design for modularity in hip implants (and all orthopedic implants in general) is the fact just prior to seating of the implant, for example 2600 microns beforehand seating of head 2610 onto trunnion 2520, there is significant motion and freedom in both rotational and angular planes. This may be a problem that is more pronounced as trunnion 2520 becomes shorter and it is more obvious with neck/body joinders, which often includes more of an oblong shaped taper.

This "freedom of motion" just before hand insertion may allow "mal-alignment" of the implants (head 2610 on to neck 2515) or (neck 2515 on to body 2525). There is essentially no structural guidance for the two components to be "keyed" into each other. At a macroscopic level the surgeon thinks and feels there is a "perfect" fit. However, at a microscopic level there is potential for large axial and rotatory mis-alignment of the two components. This mis-alignment is maintained as head 2610 is tamped into place for press-fit fixation, however, leads to poor asymmetrical surface contact area, more micro-motion and fretting and hence corrosion.

While a Morse's taper may be satisfactory in many contexts, as a joinder mechanism for an implant it may be insufficient as noted herein. In a non-implant environment, it may be easier to employ a number of adhesives, epoxies, and the like which are not used in the context for assembly of an implant.

Some embodiments of the present invention may include a new method of production and design for the trunnion in an implant, such as for a femoral implant. 3D printing is becoming useful in many fields, including orthopedics. 3D printing is utilized to produce custom guides and implants and more recently utilized to produce standard prosthesis such as the acetabular cups. Some embodiments of the present invention may include a modular prosthesis assembly, and more specifically may include a component having a femoral stem and in particular the trunnion of the component be produced with 3D printing. In that way several advantages may be attained: 1) in some cases manufacturing tolerances of the trunnion and the mating (head) bore interface can be more accurate and potentially significantly lower than +/−0.015 degrees in current manufacturing techniques; and 2) when the taper junction can be created with 3D printing, some embodiments may introduce complementary angularities into the design of the taper and bore. For example, when a trunnion is created with a cross-section as a polygon (e.g., a regular or irregular plane figure having N sides, N=3, 4, 5, 6, 7, 8, 9, 10, or more, and a cross-section of the receiving bore is complementary over its lengths, that the components will begin to align and engage at a much farther distance, (i.e.: 1000 microns as opposed to 200 microns), as the hand seating of the components are attempted.

Figure 30:
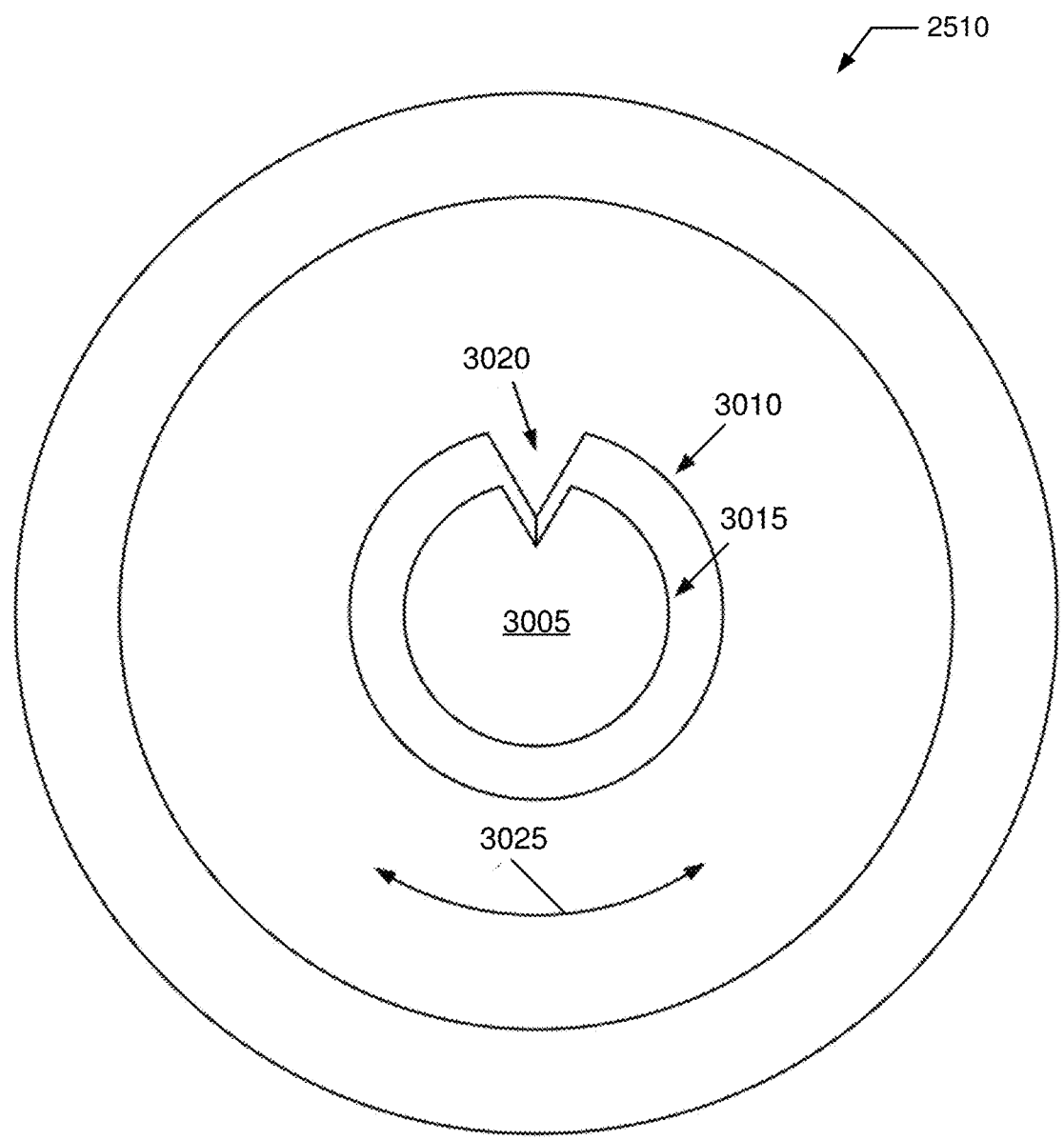
FIG. 30 illustrates a plan view of a first alternative joinder opening.

FIG. 30 illustrates a plan view of a head 2610 including an aperture 3005. Aperture 3005 includes an opening 3010 that narrows to a termination 3015, with the taper depending upon a depth of the aperture 3005 and a difference between "radii" of opening 3010 and termination 3015. Aperture 3005 includes one or more guiding structures 3020 that may extend some or all of a depth of aperture 3005, sometimes referred to herein as a key. Structure 3020 helps to limit a rotation 3025 of a trunnion 2520 coupled within aperture 3005 and allows for help in guiding the trunnion as it is being disposed within aperture 3005. When there are two or more guiding structures 3020 may be disposed at periodic (e.g., 180 degrees apart for two, 120 degrees for three, 90 degrees for four, and the like) or aperiodic at irregular locations around a perimeter of aperture 3005. Almost any discontinuity in a perimeter profile may serve as a key, including male, female, neutral (e.g., flat) extensions.

Figure 31:
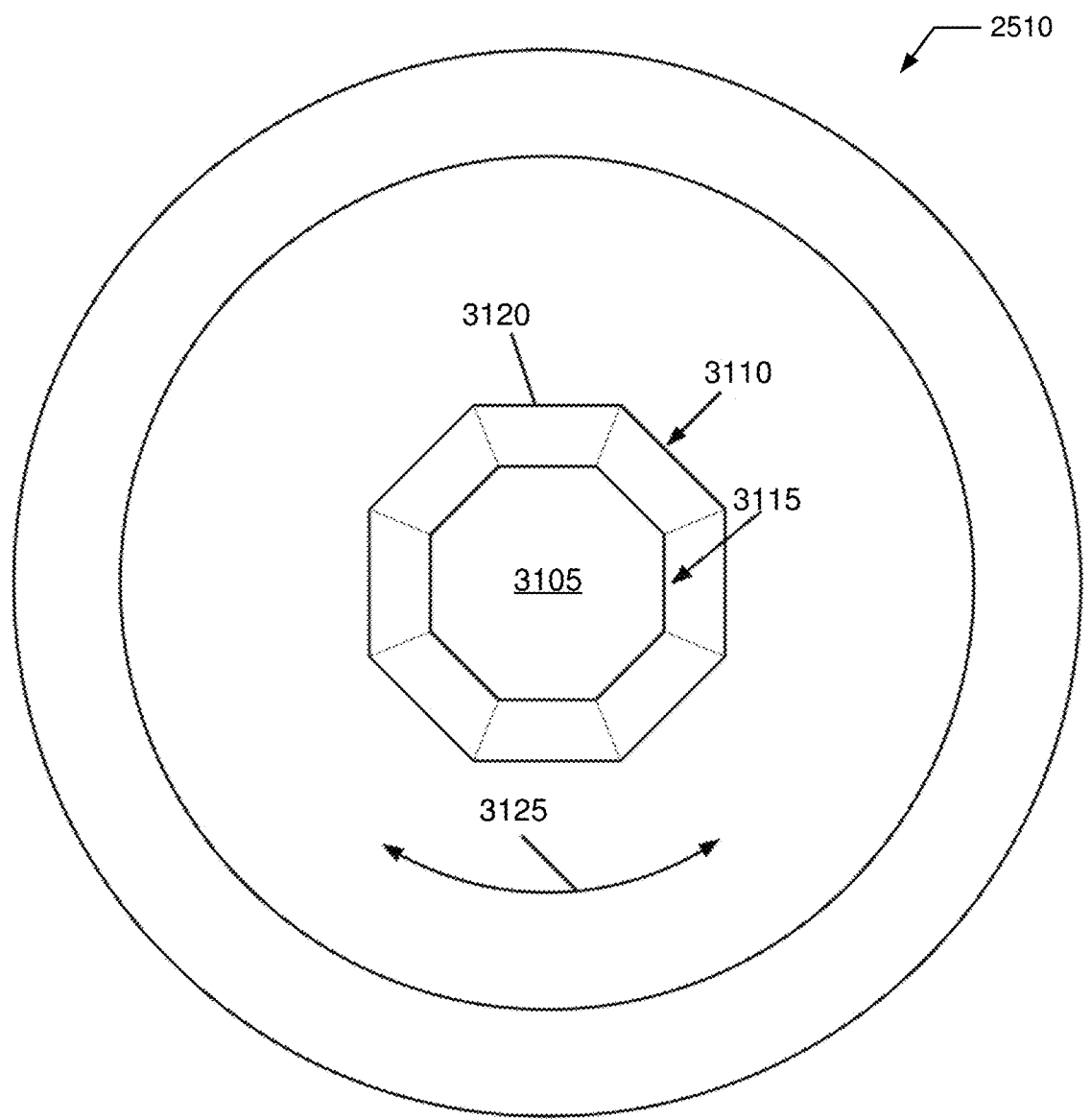
FIG. 31 illustrates a plan view of a second alternative joinder opening.

FIG. 31 illustrates a plan view of a head 2610 including an aperture 3105. Aperture 3105 includes an opening 3110 that narrows to a termination 3115, with the taper depending upon a depth of the aperture 3105 and a difference between "radii" of opening 3110 and termination 3115. Aperture 3105 may be shaped as a polygon 3120 (regular or irregular of N number of sides, N=3, 4, 5, 6, 7, 8, 9, 10, or more) that may extend some or all of a depth of aperture 3105. Polygon 3120 helps to limit a rotation 3125 of a trunnion 2520 coupled within aperture 3105 and allows for help in guiding the trunnion as it is being disposed within aperture 3105.

A sort of "guiding trail" would be inherently designed into the prosthesis, protecting against angular and rotatory misalignment. The introduction of sharp angles in the trunnion would assure proper seating and mating of the two implants without mis-alignment. This leads to more symmetrical and consistent higher surface contact areas (a better "cold weld"), with less micro-motion and therefore less fretting and corrosion. In summary some embodiments may include a different geometrical shape for the trunnion (i.e.: hexagonal as opposed to circular) that allows "early guidance" and better seating protecting against early macroscopic misalignment. One possible way that this may be accomplished more easily is with 3D printing, however, it may also be accomplished with standard manufacturing techniques. Alternatively, or in addition, to such additive manufacturing, subtractive manufacturing techniques may also be employed.

Another possible advantage of 3D printing is the ability to change the structure, density and porosity of the crystalline metals. Some embodiments may include a control of a crystalline structure of metals imbued to a metal part that is hard and brittle (higher modulus) and part that is springy and soft (lower modulus). This may allow improved capabilities in construction of prosthesis that are more natural and more closely resemble the human anatomy. For example, finite element analysis model assessing five trunnion-head junctions, Lavernia et al. J of Arthroplasy 30(6):1085 determined that not only was the area of maximum stress located on a medial aspect of the femoral neck, but also that the maximum stress in this area increased with larger head diameters.

Figure 32:
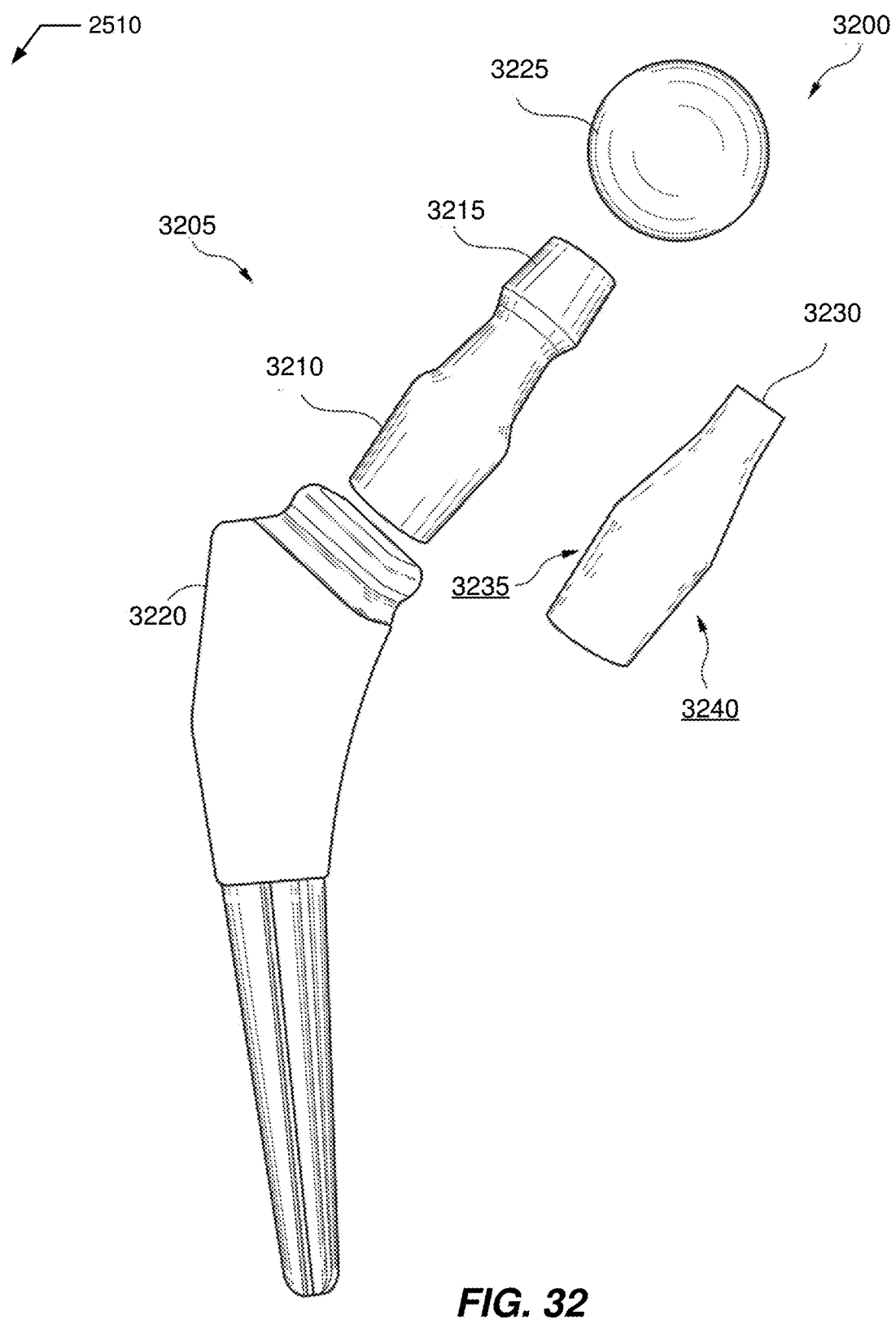
FIG. 32 illustrates a side elevation view of a modular prosthesis assembly having a tailored stiffness profile.

FIG. 32 illustrates a modular prosthesis assembly 3200 in an unassembled mode 3205. Mode 3205 illustrates three components of assembly 3200: a neck 3210 which includes a trunnion 3215, a body 3220 (which sometimes may be referred to as a stem in specific assemblies 3200), and a head 3225.

Also illustrated is a stiffness profile 3230 for neck 3210. In profile 3230, different localized regions may reflect a more or less "stiff" composition, arrangement, structure, or the like as compared to other localized regions. For example, a first lateral edge 3235 may be less stiff as compared to a second lateral edge 3240 (which is stiffer) opposite of first lateral edge 3235. Other embodiments may apply different profiles to additional and/or other portions of a modular assembly such as assembly 3200. In some embodiments, the profile(s) is/are designed to replicate the tissue profile into which the assembly is being installed. In other embodiments, the profiles may also, or alternatively, produce a profile that improves upon the natural characteristics of the tissue.

This brings up the possibility of creating a prosthesis that has multidimensional stiffness. U.S. provisional patent application Ser. No. 15/055,942, filed 29 Feb. 2016 and titled "ACETABULAR CUP IMPLANTATION SYSTEMS AND METHODS" and hereby expressly incorporated by reference thereto in its entirety for all purposes has previously described creation of an acetabular cup that has a two-dimensional or stiffness properties, which allow creation of undulatory motion and propagation of impulsive energy. This property may allow the cup to have a preference for insertion. Some embodiments of the present invention may use this technology for production of a trunnion that closely resembles the structure of the human femoral neck, with varied structural properties and modulus of elasticity. The medial calcar in the human femoral neck is designed by nature to resist compressive forces and the lateral femoral neck is more exposed to tensile stresses. A stiffness profile may match this arrangement.

Figure 33:
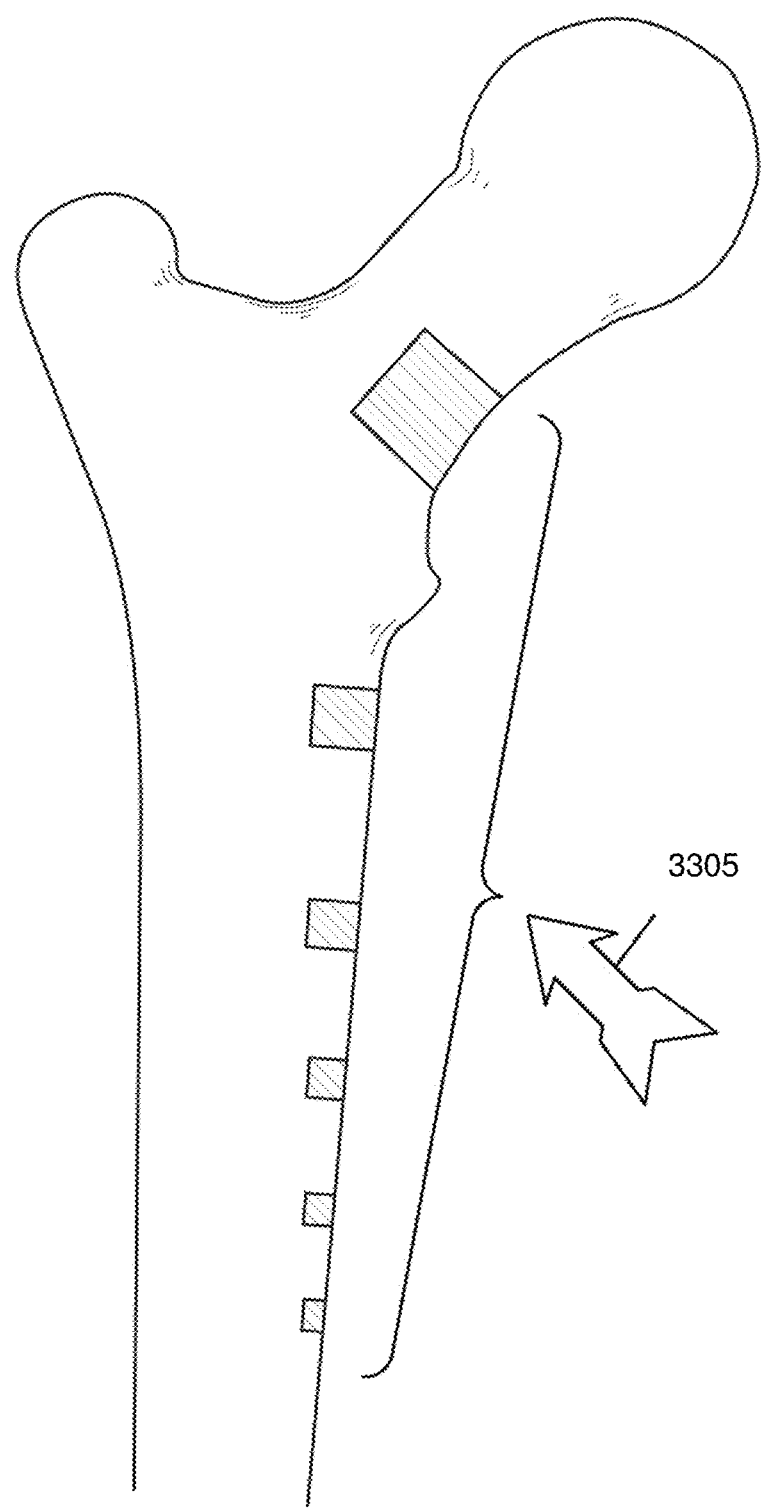
FIG. 33 illustrates a view of a portion of a bone that will receive a modular prosthesis assembly including a natural stiffness profile.
Figure 34:
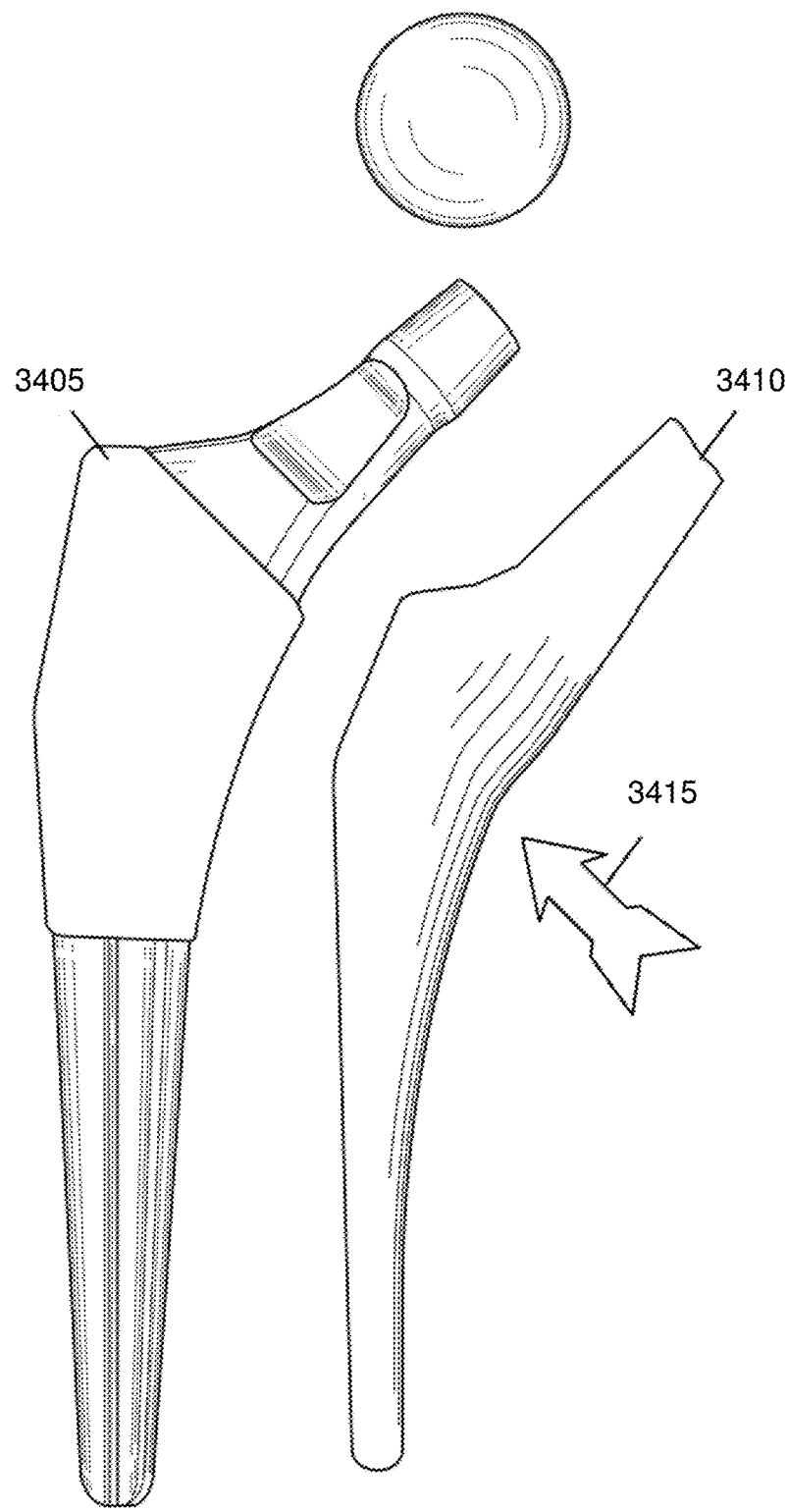
FIG. 34 illustrates a side elevation view of a modular prosthesis assembly having a tailored stiffness profile matching the bone it is to be installed into (e.g., the portion of bone of FIG. 33)

FIG. 33 illustrates a view of a portion of a bone that will receive a modular prosthesis assembly including a natural stiffness profile 3305. FIG. 34 illustrates a side elevation view of a modular prosthesis assembly 3405 having a tailored stiffness profile 3410 simulating the bone it is to be installed into (e.g., the portion of bone of FIG. 33) by varying material properties 3415 of assembly 3405 in addition to bulk level geometrical parameters of assembly 3405. While the material properties and bulk level geometrical parameters of assembly 3405 cooperate to produce a final aggregated stiffness profile, for a particular geometric design, a possibility of varying material properties at minute localized regions throughout the prosthesis allows for a virtually unlimited number of stiffness permutations and range that may not be obtained by bulk geometric variation alone. There may be many ways to achieve these varying localized variations in non-bulk geometric material properties, disclosed and described herein is a use of additive manufacturing such as three-dimensional printing.

Studies have shown that "flexural rigidity" is an important factor in inducing corrosion because it affects elastic-based micro-motion or fretting that arises at the modular junction when applied loads or moments cause elastic strain. These strains generate stretching on the tensile side and compression on the compressive side, causing displacement of approximately 5 to 40 microns in line with observation of fretting scars (Gilbert J L, Mali S Medical Implant corrosion: electrochemistry at metallic biomaterial surfaces Degradation of Implant Materials. Springer, 2012, pp. 1-28.

Some embodiments of the present invention may be that the femoral trunnion be made in a manner to replicate and/or enhance this structure, using 3D printing technology, with higher density in the calcar/medial region to resist compressive loads and lower density in the lateral neck to respond to tensile stresses. Some embodiments that include a formation of a multi-dimensionally stiff trunnion may diminish the micro-motion and fretting that occurs at the trunnion/head interface.

Figure 35:
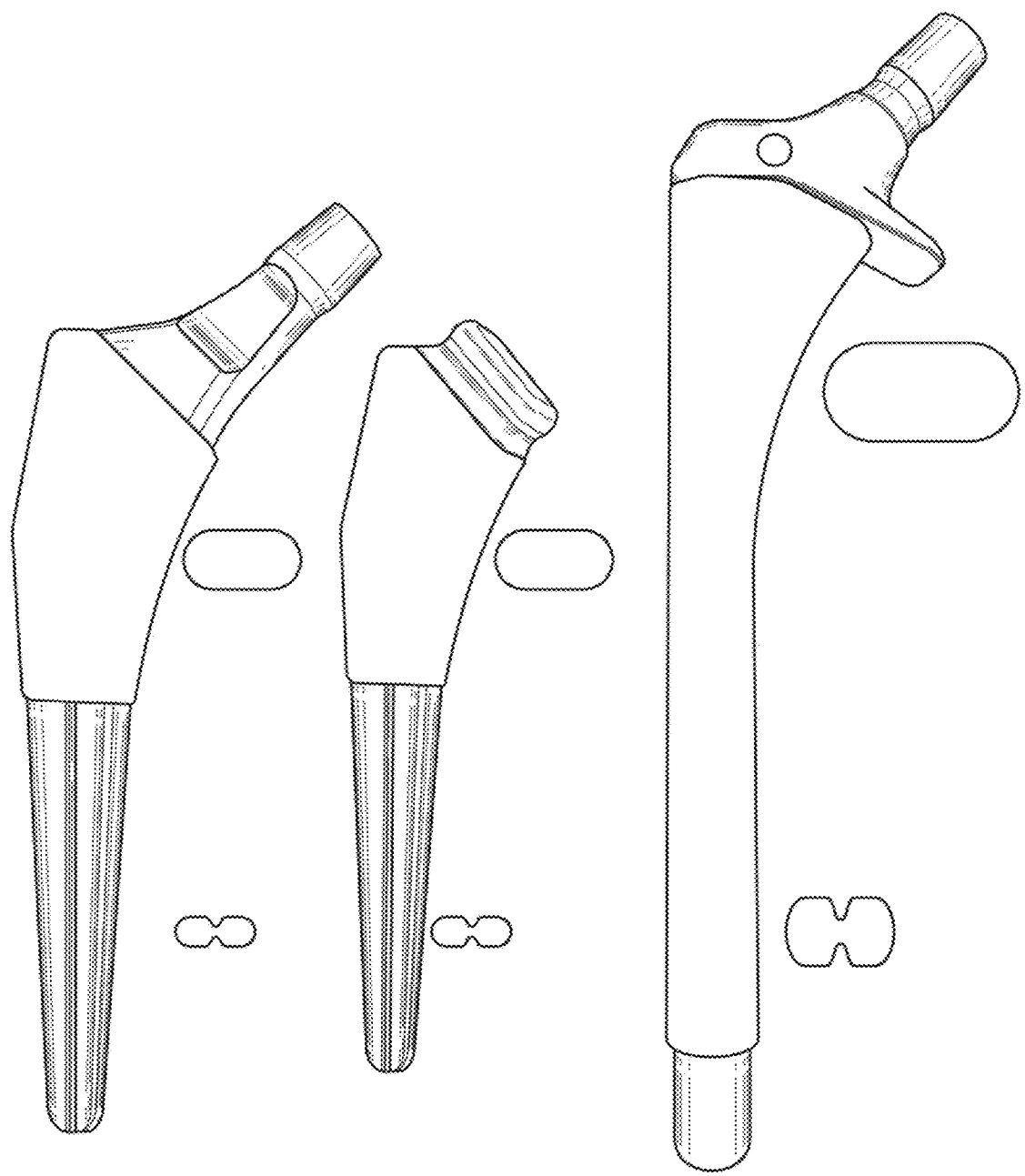
FIG. 35 illustrates a side elevation view of an alternative set of modular prosthesis assemblies having a variable stiffness profile.
Figure 36:
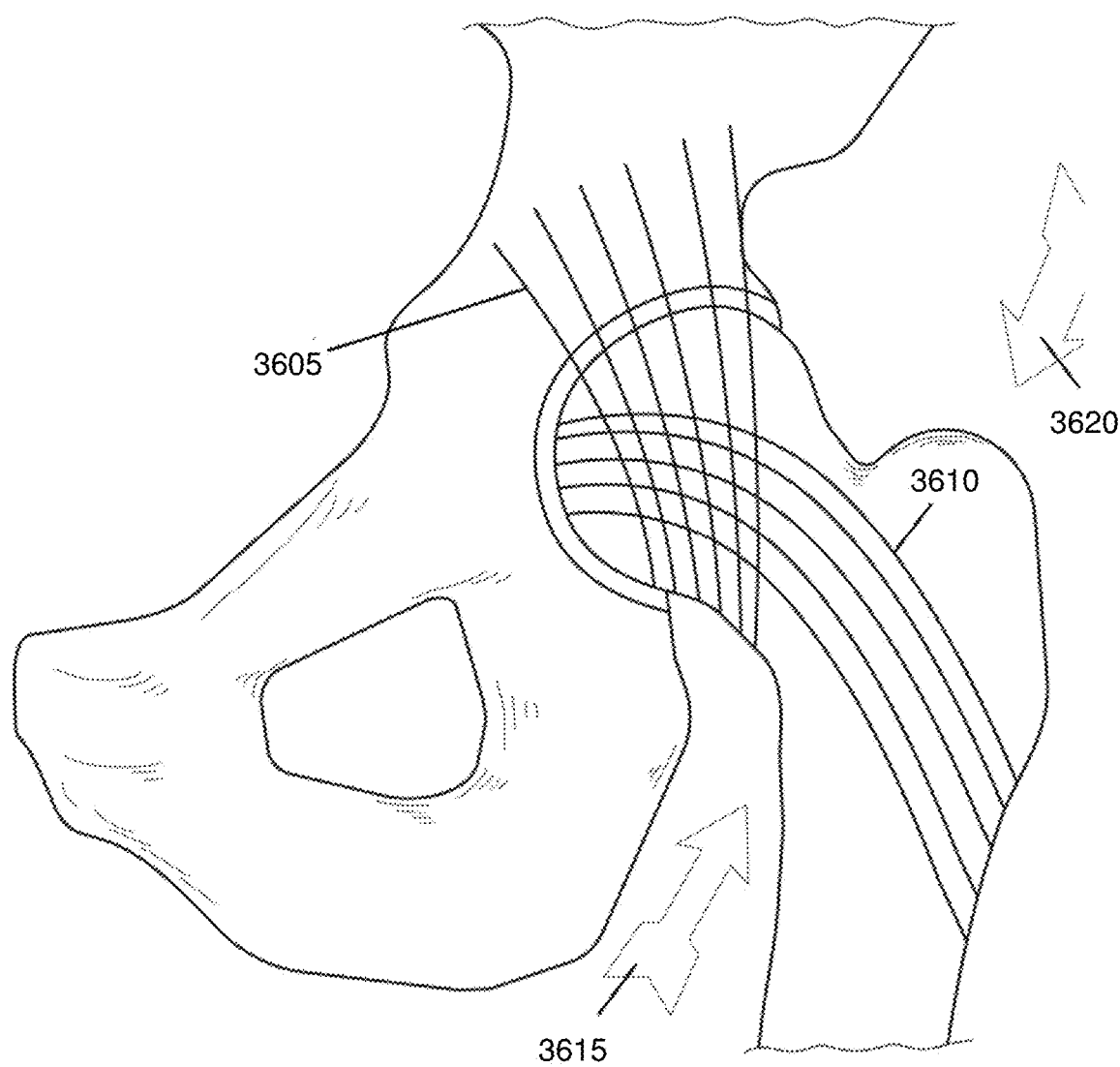
FIG. 36 illustrates a set of compressive and tensile force lines in a representative joint that can be matched by tailored prosthesis assemblies as described herein.

FIG. 35 illustrates a side elevation view of an alternative set of modular prosthesis assemblies, each having a variable stiffness profile set by bulk level geometric properties; and FIG. 36 illustrates a set of compressive 3605 and tensile 3610 force lines in a representative joint that can be simulated by tailored prosthesis assemblies as described herein. For example, a first region 3615 including medial (principal) compressive trabeculae and a second region 3620 including principal tensile trabeculae.

In the same light the stem of the femoral component may be made taking care to vary the stiffness of the whole stem from proximal to distal, simply by changing the porosity and density of the crystalline metal (now allowable through 3D printing). In this way stresses are better transferred from prosthesis to bone leading to less unwanted wear and bone resorb ion due to stress shielding. We note that until now the stiffness properties of the femoral stem (and all implants in general have been altered by changing the geometry and cross-sectional area). Some embodiments may include a new method of changing the stiffness of any modular assembly such as a prosthesis). A potentially important implementation is in the creation of multi-dimensional femoral stem. This can apply to femoral and tibial nails commonly used in trauma.

Features of one or more embodiments of the present invention may include one or more of the following:
1) Manufacture and/or use of a Force Imparting machine that delivers standardized amounts of force (magnitude), and at a precise direction (co-axial), some of which may include explicit elements illustrated herein. In addition to the incorporated patent references, U.S. Patent Application No. 62/277,294 filed 11 Jan. 2016, hereby expressly incorporated by reference thereto in its entirety for all purposes, describes some installation and force-imparting devices, some of which may be adapted using some of the principles described and/or illustrated herein. For example, an installation of a head onto a trunnion and/or an installation of a trunnion onto a body/stem.
2) A new design for a trunnion head and trunnion stem interface, with an introduction of angularity (sharp angles) and hence "early guidance system" protecting against macro and (subsequently) micro mis-alignment.
3) Manufacture of a trunnion and trunnion interface through different manufacturing techniques, for example additive rather than subtractive techniques (e.g., 3D printing).
4) Multidimensional stiffness of a trunnion that more closely resembles the mechanical properties of the human femoral neck. Stiffer on the load bearing medial neck and more elastic on tensile lateral side. As discussed further, the stiffness may be varied by components of the material while preserving geometry congruent with natural tissue/bone as some systems may alter a cross-sectional geometry, which departs from the congruence with the natural tissue, to achieve variable stiffness which better matches the replaced tissue.
5) A femoral head can, similar to the acetabular cup described in incorporated patent application, be made with two-dimensional stiffness (e.g., cross-helical arrangement in the eel's skin) or (e.g., longitudinal struts that are more flexible and horizontal bands that are more rigid) in order to allow undulatory motion and which may produce a preference/bias for insertion/assembly, structural enhancement, and/or other advantages, uses, or considerations.
6) Stiffness of implants in general and femoral components have been so far controlled by changing the geometry and cross-sectional area of the implant particularly at the tip of the prosthesis. Some embodiments may include varying the "stiffness" of the implant by changing the modulus of elasticity of the material (e.g., metal) by controlling the density and porosity of the material (e.g., crystalline metal) vis-à-vis 3D printing. Multi-dimensional prosthesis can address many of our current problems by mimicking our natural engineering. Specifically, certain parts of a proximal femur are very stiff and certain parts is less stiff and more flexible. Simulation/replication of these properties in the prosthetic femoral stem/neck/head junction, may alleviate many of the unwanted wear patterns currently seen in other systems.

Cement-less arthroplasty including total hip, shoulder, knee and ankle replacements often involve a concept of press fitting of a component of a prosthesis into live bone. This involves impacting, vibrating, and/or pushing the component into the bone to obtain an interference fit. This interference fit produces an initial primary fixation that preferably is sufficient to allow bone ingrowth (osteo-integration). When there is more than 50 µm of micro motion, bone ingrowth may not occur at the prosthesis/bone interface, resulting in fibrous tissue formation, leading to aseptic loosening and failure of the arthroplasty.

Another cause of cement-less arthroplasty failure, typically presenting late, involves the development of bone resorption. This phenomenon occurs because there is incompatibility between the elastic modulus of the bone and the implanted press fit component at this bone/implant interface. Some metal alloys such as cobalt chrome are significantly more rigid (higher modulus of elasticity) than bone and when used, for example, in femoral stem implants, lead to resorption of bone surrounding the implant. Because of the stiffness of the implant, normal stresses of daily activity are prevented from being applied to adjacent bone, leading to stress shielding and bone resorption. This can lead to fracture and osteolysis resulting in failure of the prosthesis. Previously a major concern of a particular alloy to be used focused on bio-compatibility.

Described herein are some embodiments that include an alteration of material properties of the prosthesis component (to be implanted into live bone) at the microstructure level (meso-scale, micro-scale and nano-scale) in such a fashion to generally replicate the stiffness properties of bone or in some cases to be compatible with the stiffness properties of bone at the implant/bone interface to efficiently reduce micro motion and enhance osteo-integration even when the bone structure is not exactly matched or mimicked. A motivation of at least some of these embodiments is to allow a more natural transfer of stress from the prosthesis to bone, and therefore preventing stress shielding and bone resorption. As an example, at a broad generality, the modulus of elasticity of the proximal femur (host bone) generally increases from proximal to distal as ratio of metaphyseal-cancellous bone/diaphyseal-cortical bone decreases. The proximal aspect of the femur becomes generally stiffer from proximal to distal. Similarly, the density of the proximal femur diminishes from the peripheral cortical bone to the central core. As well, certain areas of the proximal femur such as the medial calcar develop increase density due to high compressive loads in this region. It is observed however, that generally, the density and therefore elastic modulus of the proximal femur increases from proximal to distal and decreases from peripheral cortex to central core.

Recent advances in additive manufacturing such as Stereolithography Apparatus, Selective Laser Melting, and Electron Beam Melting can be adapted to allow for control of the microcellular structure of metal including size and density of the unit cells composing the metal alloy implant to achieve some of these goals of some of the embodiments. This provides control of the mechanical properties of the prosthesis for better biocompatibility with bone without necessarily simulating the bone at a microscale.

Theoretically, it is advantageous to develop a prosthesis with non-homogenous characteristics that are somewhat similar and mechanically biocompatible with bone to prevent stress shielding and bone resorption, however, this concept can produce two problems. First, too much flexibility at the implant bone interface can lead to increased micro motion (greater than 50 µm), fibrous tissue formation and aseptic loosening. Second an unchecked and smooth progression of stiffness properties (material properties of implant sometimes referred to herein as a monotonic progression in that the desired property changes in one direction (e.g., always increases) even if the magnitude of the change may or may not be uniform from one portion to another) from high to low or vice versa, at the cellular level can lead to fatigue failure of the implant over many cycles, when subjected to long term daily cyclic loading.

A metal alloy implant can be defined by a plurality of unit cells, which can be defined by their geometric properties and microstructure. The geometric properties of the unit cell can be manipulated to increase or decrease the density of a section of the implant. Studies of cellular material have shown that failure and cracks of the cellular structures, which may occur due to bending moments, happen at the junction between the unit cells, which then propagates throughout one or more structural elements to create a macroscopic fracture. The joints between the cells are therefore the weakest link of cellular material as stress localizes in these regions to reduce the endurance strength of the material.

A solution to this problem would allow for development of a prosthesis that can have some characteristics similar to the mechanical and geometric properties of natural bone, as an example, where elastic modulus increases from proximal to distal and decreases from peripheral to central, but protect against (i) (fatigue) fracture of a non-homogenous graded implant and (ii) excessive micro-motion at the bone/implant interface that may lead to aseptic loosening.

Discussed herein are solutions of utilizing additive manufacturing techniques to produce a variable material properties prosthesis that may simulate generally or specifically live bone receiving an implant. For example, in FIG. 33 and FIG. 34 the elastic modulus of the implant was proposed to be altered from proximal to distal and from peripheral to central. An embodiment of this concept is to manufacture the prosthesis with the elastic modulus of the implant generally and generically increasing from proximal to distal and decreasing from peripheral to central or vice versa.

This configuration of micro-scale bone emulation however is fallible in that cracks and fractures can occur at the cellular junctions of the unit cells producing the metal alloy implant, leading to macroscopic failure of the implant particularly in the regions where the implant becomes more and more flexible. As well, the more flexible portions of the prosthesis, especially more distally, may be prone to excessive micro-motion due to high flexibility leading to poor osteo-integration (fibrous ingrowth).

Some embodiments of the present invention address this problem to allow creation of non-homogenous implants with gradient material properties (which may be uniform or non-uniform monotonically varying) from proximal to distal and from peripheral to central without increasing propensity for cracks and fracture at the cellular junctions and without increasing the potential for increased micro motion, poor primary implant stability and aseptic loosening. While those monotonic solutions may be valuable, implants that address the potential for cracks and fracture may also be of interest to a surgeon, patient, or implant manufacturer.

One solution includes a combination of (i) a prosthesis having a variable material prosthesis concept as described herein with (ii) formation of a support system as described in U.S. patent application Ser. No. 15/234,927 titled MECHANICAL ASSEMBLY INCLUDING EXTERIOR SURFACE PREPARATION, hereby expressly incorporated by reference for all purposes. This support system may include a discrete or integrated arrangement of elements, such as rib and plank (or counter-rotating helical) lattice elements. The support system of that application conferred a particular type of multi-dimensional asymmetric stiffness to the implant, which would produce a propensity for insertion. For example, rib elements may extend longitudinally in the foundation of the prosthesis, and throughout the length of the prosthesis. Plank elements are distributed circumferentially throughout the prosthesis. These structures each have different material properties and elastic moduli (flexible longitudinal ribs and stiffer circumferential planks) that would increase propensity for insertion, such as due to creation of an undulatory motion, such that when force is applied to the implant, the energy propagates more advantageously through its longitudinal axis to produce the propensity for insertion.

In the context of embodiments of the present invention, such a support system described in the incorporated patent application may provide a secondary important function of enhancing structural rigidity to protect the implant against fatigue failure from (cyclic bending and torsional moments), as well to minimize micro motion at the bone implant interface. The support system may support the multi-dimensional asymmetric stiffness of the present implant not necessarily to provide a propensity for insertion (though some embodiments may provide this attribute as well) but to resist the fractures in addition to, or in lieu of, the propensity for insertion.

This support system may include tubular homogeneous elements within a non-homogeneous graded implant producing one or both of two distinct functionalities to the prosthesis: (i) increased propensity for insertion and (ii) structural elements within a foundation of the prosthesis to resist or prevent cracks and fractures and to provide circumferential tubular areas of enhanced structural rigidity for increased primary stability of the implant, minimizing chance of aseptic loosening.

Similar functionalities can be obtained by use of helical and counter helical structures also described in the incorporated patent application, as well any variation of homogenous tubular struts arranged in different orientations to counteract the weaknesses of a gradient non-homogenous prosthesis to tensile and torsional stresses.

This support system may include one-dimensional (e.g., just rib elements or plank elements), two-dimensional (e.g., rib elements with orthogonal plank elements), three-dimensional (e.g., an additional element combined with the rib and plank elements) arrangements.

The incorporated patent application also describes a concept of altering the material properties of metal used in modular prosthesis. For example, in total hip replacement surgery the femoral stem is initially implanted in bone, and subsequently the femoral head is press fit (impacted) onto the he trunnion (of the stem) through use of a Morse Taper engagement. The trunnion of the femoral stem has evolved over the years to be shorter and more flexible to allow surgery with smaller components through smaller and less invasive incisions. However, increased flexibility and altered geometry of the trunnion in particular has led to significant problems including increased micro-motion at the head trunnion interface, leading to fretting and corrosion (metallosis).

Flexural rigidity (or lack of) has been recognized as a contributing factor to micro-motion and development of fretting and corrosion and trunnionosis. The modular components of FIG. 32 may be manufactured in such manner to allow medial (3240) aspect of trunnion 805 to be more rigid (higher elastic modulus) and the lateral (3235) aspect of the trunnion to be more flexible (lower elastic modulus). This general configuration or other variations of monotonic (uniform or non-uniform) gradient in metal density of the modular prosthesis can produce a more stable interlock between the modular components at the head neck junction of Morse Taper (or any other modular prosthesis to prosthesis connection).

The concept of the combination of the support system with the tailored material properties of a prostheses to simulate or be compatible with the bone material properties to minimize adverse results from implanting the prosthesis can similarly be applied to embodiments for modular prosthesis junctions (Morse Taper or other junctions). Tubular longitudinal like elements (rib elements) within the foundation of the prosthesis provide increased tensile strength throughout the structure of the modular prosthesis. The tubular circumferential elements (plank elements) conversely increase the primary stability at the modular interface by producing a series more rigid rings through the body of the prosthesis preventing micro-motion at the prosthesis-prosthesis interface. This combination of homogeneous tubular struts interspersed, in various geometric fashions, within a non-homogeneous graded implant prevents fracture and enhances primary implant-to-implant stability.

Figure 37:
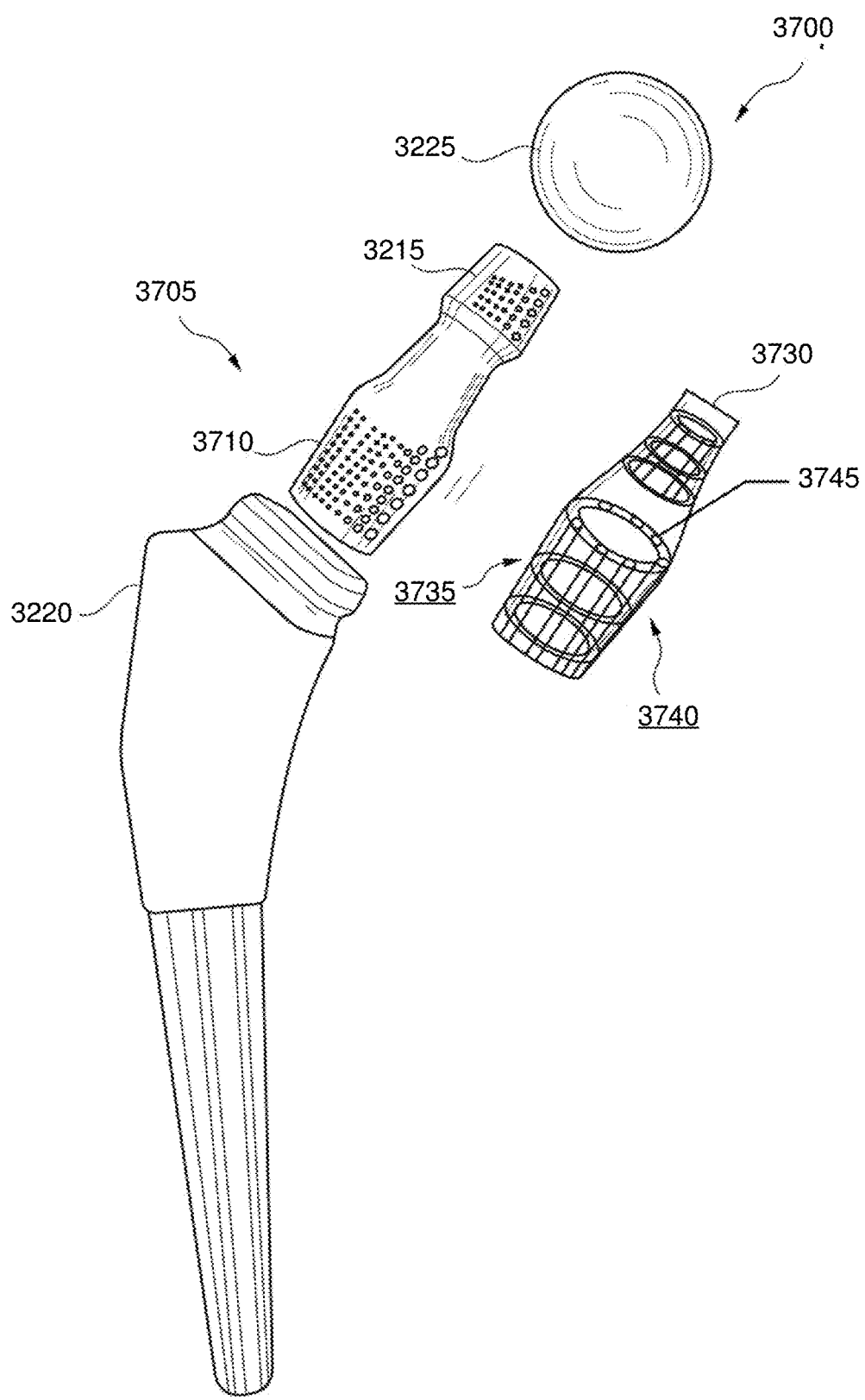
FIG. 37 illustrates a side elevation view of an alternative modular prosthesis assembly having a tailored stiffness profile.

FIG. 37 illustrates a side elevation view of an alternative modular prosthesis assembly 3700 having a tailored stiffness profile similar to assembly 3200 illustrated in FIG. 32. Assembly 3700 may include common elements with assembly 3200 except as otherwise described herein or as understand from the context.

Modular prosthesis assembly 3700 is also illustrated in an unassembled mode 3705 as assembly 3200 in FIG. 32. Mode 3705 illustrates three components of assembly 3700: a neck 3710 which includes a trunnion 3215, a body 3220 (which sometimes may be referred to as a stem in specific assemblies 3200), and a head 3225.

Also illustrated is a stiffness profile 3730 for neck 3710 along with an additional support mechanism as described below. In profile 3730, different localized regions may reflect a more or less "stiff" composition, arrangement, structure, or the like as compared to other localized regions. For example, a first lateral edge 3735 may be less stiff as compared to a second lateral edge 3740 (which is stiffer) opposite of first lateral edge 3735. Other embodiments may apply different profiles to additional and/or other portions of a modular assembly such as assembly 1300. In some embodiments, the profile(s) is/are designed to replicate the tissue profile into which the assembly is being installed. In other embodiments, the profiles may also, or alternatively, produce a profile that improves upon the natural characteristics of the tissue and/or compatible with the general stiffness of bone receiving the implant.

In FIG. 37, the stiffness profile is depicted by small circles—with a diameter of these small circles reflecting a parameter of the stiffness profile (e.g., a stiffness) at the location of the small circle. The diameters in FIG. 37 change uniformly and monotonically.

Also illustrated in FIG. 37 is inclusion of a support system 3745 that is added to one or more portions of assembly 3700. Support system 3745 may be implemented in many ways to incorporate a set of support elements (e.g., orthogonal rib and plank elements or helical and counter helical elements) that are distributed in the desired portion(s). These support elements may be discrete elements or may be regions in which material properties are locally varied during an additive manufacturing process to effectively reproduce the function of these support elements in the desired regions without separate discrete and visually identifiable identities. Support system 3745 may be integrated into any layer of a multilayer structure (e.g., a foundation layer) that may include a surface layer or other layer of assembly 3700.

Some manufacturing or design techniques for assembly 3700 may produce small scale material property variations that may have a susceptibility to fracture of unit elements reproducing a desired implant. Support system 3745 may be added into regions or areas at risk of fracture to resist this fracturing. There are many variations of this support system such as one-dimensional support elements (elements running in a single direction), two-dimensional support elements (a first set of support elements (e.g., rib elements) and a second set of support elements (e.g., plank elements)) orthogonal or non-aligned in some sense to the first set of support elements, three-dimensional support elements (three sets of orthogonal or non-aligned support elements), or even more sets.

This brings up the possibility of creating a prosthesis that has multidimensional stiffness for one or both of asymmetric stiffness with a propensity for insertion and/or a propensity for resisting localized fracturing, such as fracturing arising from small scale material property variations to produce a desired stiffness profile. The incorporated provisional patent application Ser. No. 15/055,942, filed 29 Feb. 2016 and titled "ACETABULAR CUP IMPLANTATION SYSTEMS AND METHODS" has previously described creation of an acetabular cup that has a two-dimensional or stiffness properties, which allows for a propensity for insertion which may include creation of undulatory motion and propagation of impulsive energy to make insertion simpler. This property may allow the cup to have a preference or propensity for insertion. Some embodiments of the present invention may use this technology for production of a trunnion that closely resembles the structure of the human femoral neck, with varied structural properties and modulus of elasticity. The medial calcar in the human femoral neck is designed by nature to resist compressive forces and the lateral femoral neck is more exposed to tensile stresses. A stiffness profile may match this arrangement. Use of support system 3745 (in addition to components for the insertion enhancement or by modifying the components to produce a multi-objective characterization of these support system components) may resist the fracturing and may enhance insertion when desired.

As illustrated in FIG. 37, support system 3745 may be disposed in different independent areas (in effect different subsystems) such as one subsystem in neck 3710 and another subsystem in trunnion 3315) each providing one or both of insertion propensity modification and fracture resistance as needed or desired.

Figure 38:
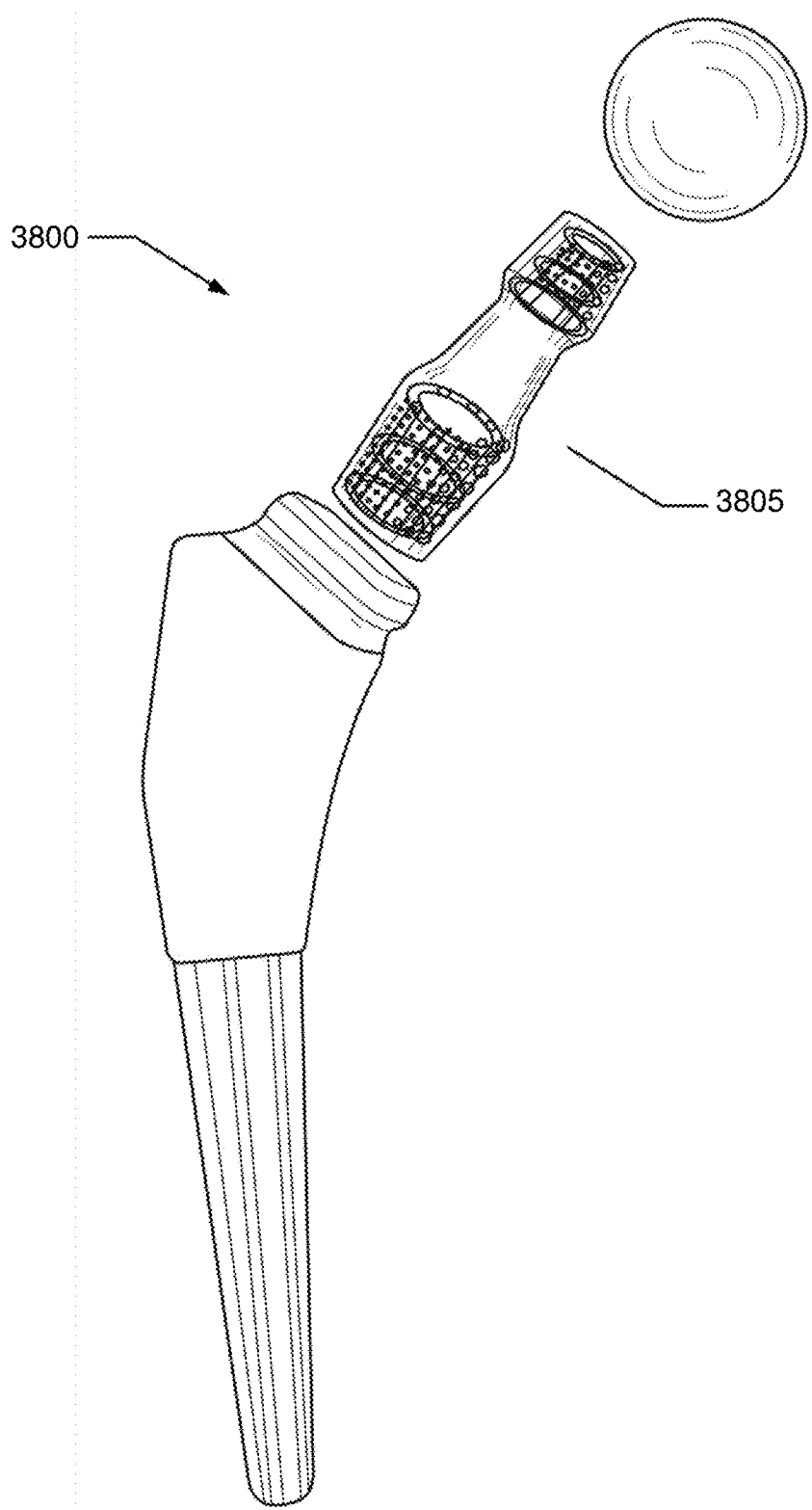
FIG. 38 illustrates a combination of a support system with a variable stiffness profile for an alternate embodiment such as illustrated in FIG. 37.

FIG. 38 illustrates a combination of a support system with a variable stiffness profile for an alternate embodiment 3800 such as illustrated in FIG. 37 in which embodiment 3800 explicitly includes a mode 3805 with neck and trunnion including both the variable material properties and the support system as independently illustrated in FIG. 37. As noted herein it is not required that functions be separated as independently illustrated in FIG. 37.

Figure 39:
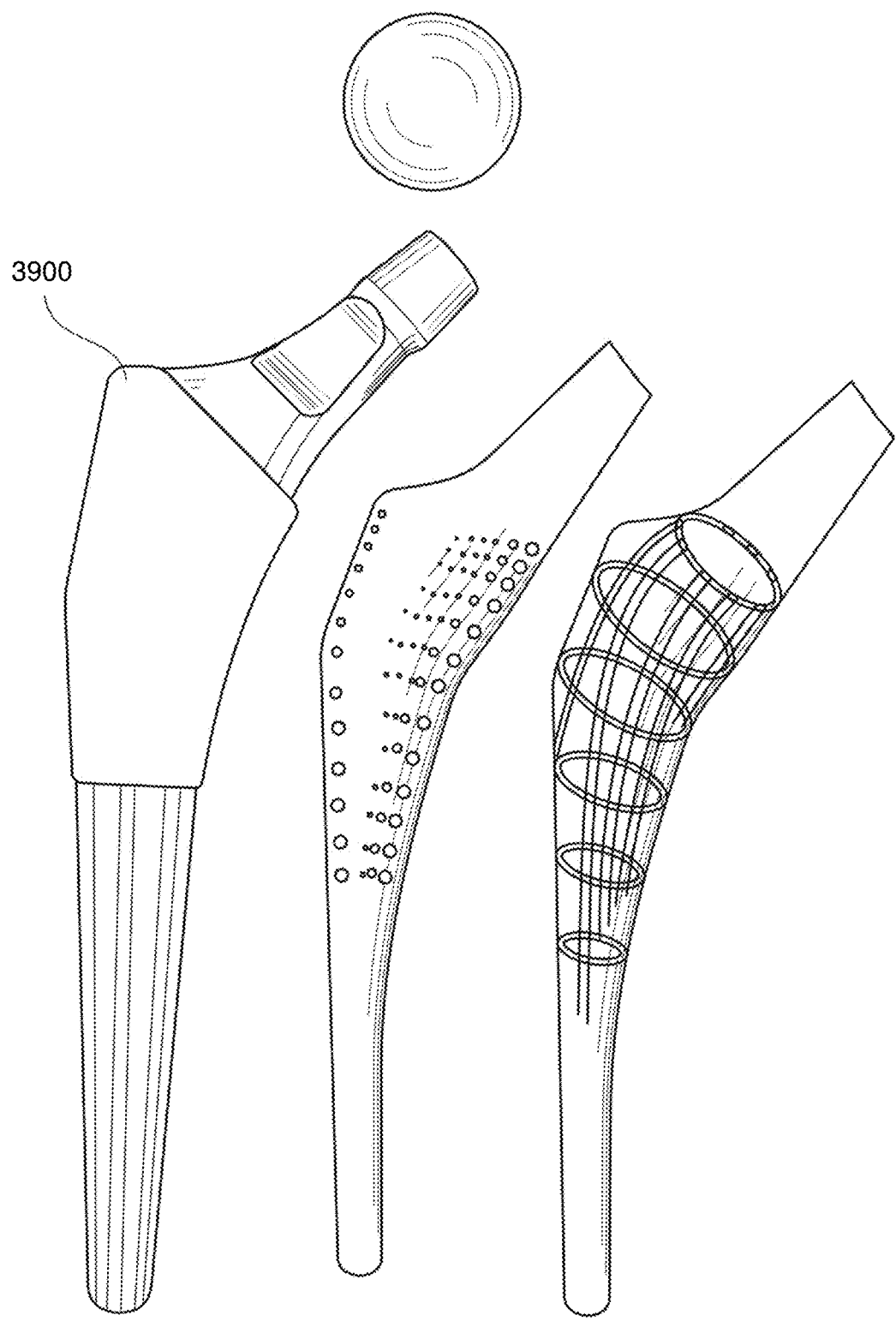
FIG. 39 illustrates a side elevation view of an alternate modular prosthesis assembly having a tailored stiffness profile matching the bone it is to be installed into (e.g., the portion of bone of FIG. 33)

FIG. 39 illustrates a side elevation view of an alternate modular prosthesis assembly 3900 having a tailored stiffness profile matching the bone it is to be installed into (e.g., the portion of bone of FIG. 33) and inclusion of a support system as described herein (e.g., the discussion of assembly 3700. The support system may enable one or both of propensities for insertion and/or fracture resistance.

Figure 40:
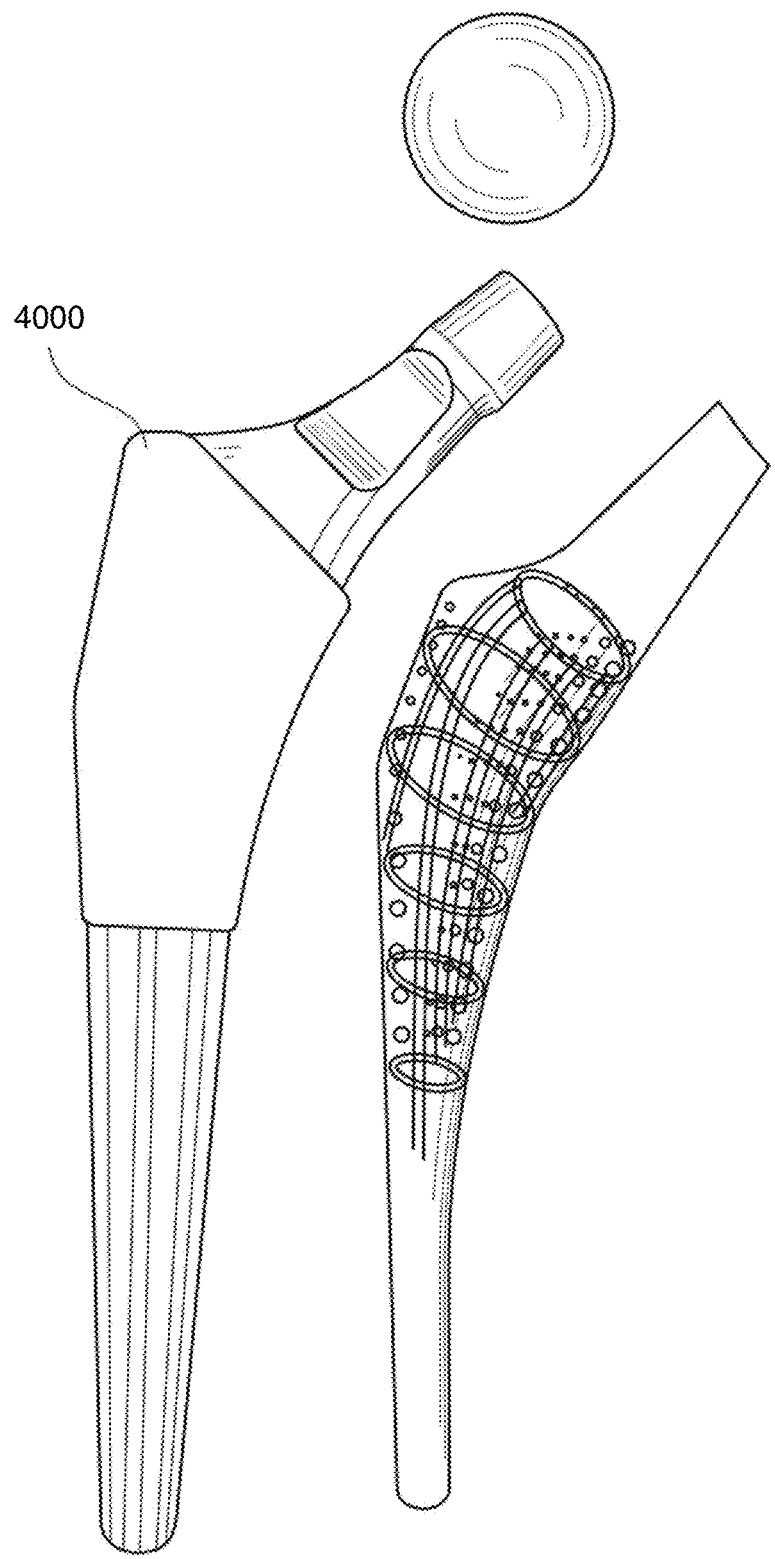
FIG. 40 illustrates a combination of a support system with a variable stiffness profile for an alternate embodiment such as illustrated in FIG. 39.

FIG. 40 illustrates a combination of a support system with a variable stiffness profile for an alternate embodiment 4000 such as illustrated in FIG. 39 in which embodiment 4000 explicitly includes both the tailored variable material properties and the support system as independently illustrated in FIG. 39. As noted herein it is not required that functions be separated as independently illustrated in FIG. 39.

Figure 41:
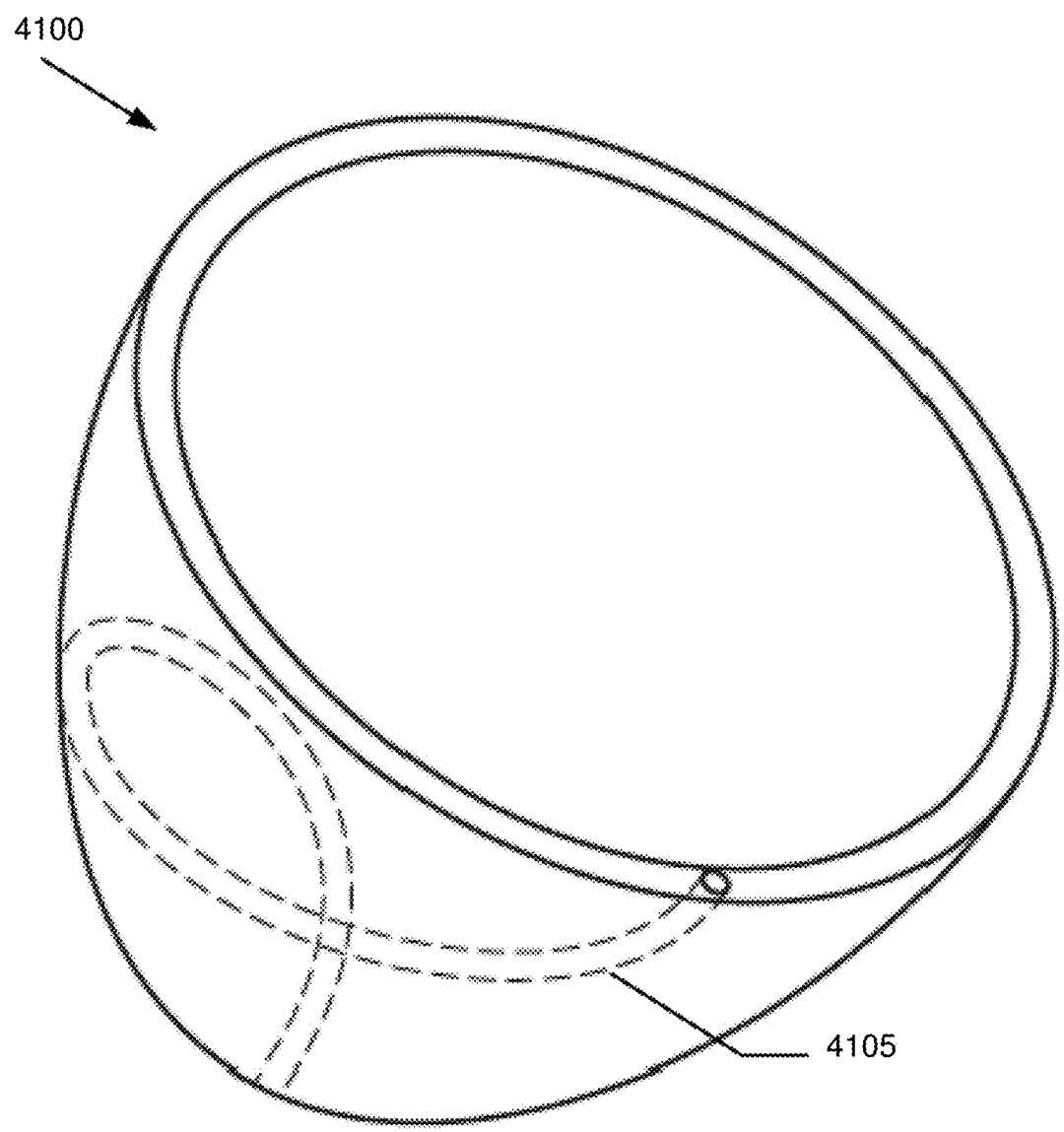
FIG. 41 illustrates an alternate support system including a helical element in an implant (e.g., an acetabular cup)

FIG. 41 illustrates an alternate support system 4100 including a helical element 4105 in an implant (e.g., an acetabular cup). The support system 4100 may support one or both of the propensities for insertion and/or fracture resistance.

Some of the embodiments include use of an insertion force applied to a force transfer device to distribute the insertion force to the implant in one of a number of different ways as described herein. In some instances, this insertion force may include, consist of, or consist essentially of a vibration component. This vibration component preferably includes an intentional/purposeful insertion vibration producing a vibration in the implant facilitating the insertion of the implant into a prepared hole in a prepared portion of bone. This insertion vibration desirably resists dampening (such as may occur with incidental non-driven/non-purposeful vibration). For example, the insertion vibration may drive the implant at a vibration magnitude of 1-5 mm, 100-500 N (and in some instances perhaps 100-1000 N), and a frequency greater than 30 Hz (for example 30-350 Hz). This is a non-ultrasonic vibration contribution. Ultrasonic vibrations may be superimposed upon this non-ultrasonic vibration contribution (with a different magnitude, force, and/or frequency).

Figure 42:
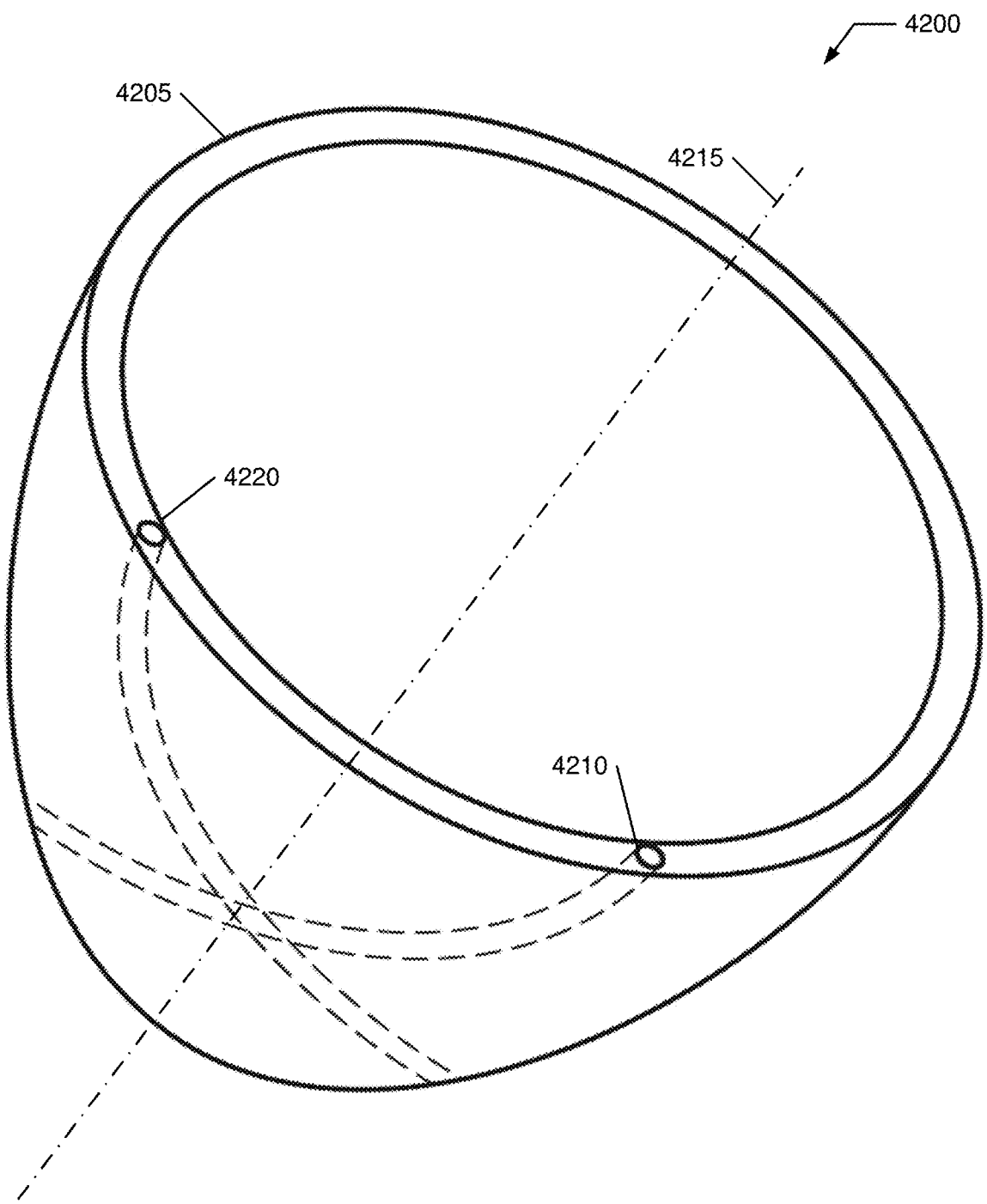
FIG. 42 illustrates a perspective view of a prosthesis including a two-dimensional asymmetrical stiffness implemented by counter-rotational helical structures disposed within a foundation of the prosthesis.

FIG. 42 illustrates perspective view of a prosthesis 4200 including a two-dimensional asymmetrical stiffness implemented by counter-rotational helical structures disposed within a foundation 4205 of prosthesis 4200. Prosthesis 4200 includes a first set 4210 of helical structures installed clockwise about an axis 4215 and includes a second set 4220 of helical structures installed counterclockwise about axis 4215; the sets of helical structures cooperatively configured to produce a two-dimensional asymmetric stiffness implementing a bias for insertion of prosthesis 4200.

Current metal implants used in orthopedic arthroplasty employ isotropic materials such that they exhibit equal physical material properties along all axis (when measured in different directions). Young's modulus is a measure of the ability of a material to withstand deformation. Isotropy in an orthopedic implant refers to the fact that the young's modulus of the implant does not change based on the direction of applied load. Young's modulus of elasticity is used to measure the stiffness properties of the constituent material independent of the shape and geometric properties of the implant.

Stiffness, defined as the extent to which an object resists deformation in response to applied force (converse of flexibility) is a function of elastic modulus of the material as well as the shape, geometry and boundary conditions of the implant.

The modulus of elasticity is an intensive property of the material. Stiffness, on the other hand, is an extensive property of a material as it is dependent on the constituent material as well as the shape, geometry and boundary conditions of the material.

The strength of a material refers its ability to withstand an applied load without failure or plastic deformation. The field of strength of materials deals with forces and deformations that result from the forces acting on the material. Young's modulus of elasticity (as a measure of stiffness) for cortical bone is approximately 20 GPa (Gigapascals).

The ultimate tensile strength human cortical bone is about 136 MPa (Mega Pascals). The ultimate compression strength of human cortical bone is about 205 MPa. —The strength of the bone or any other material is defined by the point of failure or by the load sustained before the failure. The strength may also be analyzed in terms of storage of energy, the area under the load-deformation or stress-distension curve.

Current implants used in orthopedic surgery are made of metallic materials such as Stainless Steel (316), Cobalt-Chrome (MP35N, L-605, and Elgiloy), Titanium (Ti-6A1-4V) and CP titanium), Nickel-Titanium (Nitinol). These metals have significantly higher strength and stiffness properties than human compact bone.

With respect to stiffness (modulus of elasticity), the two commonly used metals Cobalt-Chrome (200 GPa) and Titanium (90-100 GPa) are around 10 to 5 times stiffer respectively than cortical compact bone. With respect to strength, Cobalt Chrome and Titanium can be up to five times stronger than compact bone.

Strength and Stiffness attributes of metals used in orthopedics are presented in Table I.

TABLE I

| Attribute | Stainless Steel | Cobalt-Chrome | Titanium | Nitinol |
|---|---|---|---|---|
| Strength | medium (300/560 MPa) | high (600/1140 MPa) | high (880/950 MPa) | high (500/1400 MPa) |
| Stiffness | high (200 GPa) | high (200 GPa) | moderate (90 GPa) | very low (~25 GPa) |

A particular problem currently exists in orthopedics and particularly the field arthroplasty, in that the metal prosthesis used are isotropic with material and mechanical properties that are vastly different than bone, to which they must bond.

This problem has been discussed in the incorporated parent applications, including ribs, planks, helixes, intramedullary (IM) rod, structured stiffness elements producing a device profile reproducing some bone characteristics, anisotropic metals and robotic fracture fixation, including robotic and anisotropic rods.

This disparity between stiffness properties of the implant and bone produce very specific problems including the following: 1. Stiffer prosthesis have the advantage of producing less micromotion which leads to better bone ingrowth and osteointegration into the surface of the prosthesis. However, strong bone ingrowth which appears in the stiffer distal cortical bone (as with the femoral prosthesis) produces the phenomena of stress shielding. The proximal femoral bone for example does not experience the normal lines of stress and therefore bone resorbs in this region over time, becoming mechanically weak. Bone resorption may eventually lead to periprosthetic fractures and eventual implant loosening. 2. Flexible prosthesis do not have the problem of stress shielding and bone resorption but can produce too much micromotion which leads to poor bone ingrowth and implant (aseptic) loosening. 3. Non-homogenous graded implants produce an implant with the elastic modulus of the implant generally and generically increasing from proximal to distal and decreasing from peripheral to central or vice versa.

It may be advantageous to develop a prosthesis with non-homogenous gradient characteristics that are somewhat similar and mechanically biocompatible with bone to prevent stress shielding and bone resorption, however, this concept can produce two problems. This concept also has weaknesses associated with the alteration of the crystalline structure of metal. First, too much flexibility at the implant bone interface can lead to increased micro motion (greater than 50 μm), fibrous tissue formation and aseptic loosening. Second an unchecked and smooth progression of stiffness properties (material properties of implant sometimes referred to herein as a monotonic progression in that the desired property changes in one direction (e.g., always increases) even if the magnitude of the change may or may not be uniform from one portion to another) from high to low or vice versa, at the cellular level can lead to fatigue failure of the implant over many cycles, when subjected to long term daily cyclic loading.

A metal alloy implant can be defined by a plurality of unit cells, which can be defined by their geometric properties and microstructure. The geometric properties of the unit cell can be manipulated to increase or decrease the density of a section of the implant. Studies of cellular material have shown that failure and cracks of the cellular structures, which may occur due to bending moments, happen at the junction between the unit cells, which then propagates throughout one or more structural elements to create a macroscopic fracture. The joints between the cells are therefore the weakest link of cellular material as stress localizes in these regions to reduce the endurance strength of the material.

A stiffness of implants in general have been so far controlled by changing a geometry, including cross-sectional area of the implant. However, varying the "stiffness" of the implant is disclosed by changing a modulus of elasticity of the material (e.g., metal), for example by controlling a density, porosity, and structure of the material (e.g., crystalline metal) vis-à-vis 3D printing.

Recent advances in additive manufacturing such as Stereolithography Apparatus, Selective Laser Melting, and Electron Beam Melting are adapted to allow for control of the microcellular structure of metal including size and density of the unit cells composing the metal alloy implant to achieve some of these goals of some of the embodiments. This provides control of the mechanical properties of the prosthesis for better biocompatibility with bone without necessarily simulating the bone at a microscale. That is, some mechanical properties may be implemented with a framework without attempting to simulate the actual bone microstructure.

A metal alloy implant can be defined by a plurality of unit cells, which can be defined by their geometric properties and microstructure. The geometric properties of the unit cell can be manipulated to increase or decrease the density of a section of the implant.

Bone is an anisotropic material meaning the bone behavior will change depending on the direction of load application. Isotropic material such as glass and metal on the other hand are material that have identical properties regardless of direction of load application.

In general, bone is a good composite material, having a strength higher than either of its components, apatite or collagen. The softer (low-modulus) collagen prevents the stiff (high-modulus) apatite from undergoing brittle fracture, while apatite acts as a rigid scaffold to prevent collagen from yielding. Not surprisingly, the mechanical properties of bone are as complex and varied as the anatomy and composition. Seemingly simple properties such as bone strength, stiffness, and energy absorption to failure depend not only on material properties of bone (e.g., inherent composition, microscopic morphology of bone components, bonds between fibers and matrix and bonds at points of contact of fibers) but also on structural properties (e.g., geometry of whole bone, bone length, and bone curvature). Furthermore, it is well known that the material strength of bone varies with the age, sex, and species of animal under investigation and with the location of bone, such as femur versus humerus. In attempting to assess structural and material properties of bone using mechanical testing techniques, additional variation in bone strength may result from factors such as the orientation of load applied to the bone (since bone is anisotropic), strain rate (rate of deformation), and testing conditions, including tension versus compression, bending versus torsion, wet bone versus dry bone. Mechanical testing may yield even wider dispersion in results when specifically applied to the material and structural properties of healing bone.

Certain bones in the human anatomy, for example the proximal femur and the acetabulum, have developed particular composite frameworks based on lines of stress (force) experienced with normal function. For example, the proximal femoral calcar experiences compressive forces while the greater trochanteric region experiences tensile forces. Similarly, the acetabulum has particular structural properties to withstand compressive forces in the anterior (ilial) and posterior (ischial) columns with less supportive areas in the inferior (acetabular notch) and superior aspects.

It would be desirable to create prosthesis that have similar composite framework (reinforcements) structures similar to bone in order to allow more fluid and progressive transfer of loads between bone and implant associated with normal stresses of daily activity. An embodiment of a composite anisotropic prosthesis would transfer loads more fluidly and smoothly from the environment to bone to the prosthesis preventing problems such as stress shielding and bone resorption, too much micromotion and poor bone ingrowth, and implant (acetabular shell) deformation, and fracture of implants.

As described in an incorporated parent application bone is a composite anisotropic structure. Bone is a live structure with 70% of its extracellular matrix composed of mineral components, and 30% composed of organic components (90% type 1 collagen and 5% non-collagenous proteins). The structure of cortical bone shows cortical lamellar bone: intersticial system, osteonal lamalle, and outer circumferential system. There is an intricate vascular system to provide nutrition to the living cells in bone (osteocytes). The complex arrangement of the microstructure and meso-structure of bone including the lamellar rings and interstial lamellar and external circumferential lamellar system is noted. A combination of the microstructure, mesostructure and macrostructure of bone may allow bone to be anisotropic and viscoelastic in nature. Viscoelastic material has properties that are rate dependent or have time-dependent responses to applied force. An anisotropic material has properties that differ depending on the direction of load. Bone, muscle, ligament, and tendons all are anisotropic and viscoelastic. An isotropic material has the same mechanical properties in all directions. In general metals and ceramics are isotropic.

At a microscopic level an embodiment of an anisotropic implant may include simulation of a triple helix structure of collagen fibrils arranged in specific quarter-stagger array seen in electron microscopy, potentially conferring the viscoelastic nature to bone. Also, an embodiment may include an oblique arrangement of metallic "fibrils" to simulate an oblique arrangement of collagen fibers in bone.

In a sense certain parts of the human bony anatomy are specialized to deal with certain types of force. As mentioned earlier the medial calcar of the femur is designed to withstand significant compressive forces. The anterior and posterior columns of the acetabulum provide an asymmetrical increased areas of stiffness to the acetabular bone. What is need is composite anisotropic prosthesis that allow customization of stiffness and strength attributes of these specialized areas of bone in order to allow smooth and fluid transfer of force between the environment bone and prosthesis, for the ultimate goal of enhancing the longevity of the prosthesis.

Parent applications of this disclosure have previously discussed the problem of stress shielding and bone resorption with certain solutions. An embodiment proposed development of a prosthesis with non-homogenous gradient characteristics that are somewhat similar and mechanically biocompatible with bone to prevent stress shielding and bone resorption. An embodiment proposed the addition of ribs and planks within the foundation of the prosthesis to produce a composite structure, similar to the concept of reinforced concrete, to allow creation of a framework within the body of the prosthesis to allow better and smoother load transfer (prevent stress shielding, bone resorption and too much micromotion), prevent fracture at the cellular junctions in gradient non-homogenous prosthesis) and possibly to allow more efficient insertion with undulatory motion while receiving insertional forces.

Herein addressed is another common problem with use of an isotropic implant in hip arthroplasty. Press fit fixation requires impaction of an oversized acetabular cup (shell) into a relatively undersized acetabular bony cavity. However, the bone cavity is neither symmetrical nor homogenous. The acetabular rim contains more dense compact bone than the acetabular dome. Similarly, the anterior and posterior columns of the acetabulum have denser, stiffer and more compact bone while the superior dome and the acetabular notch have less compact bone and or support. This creates an asymmetrical pinching effect on the acetabular shell (anteriorly and posteriorly) that is impacted to obtain press fit fixation, which deforms the acetabular shell. The deformed acetabular shell then causes higher frictional torques between the shell and the insert, which may be polyethylene, ceramic or metal. These increased frictional forces can cause metal and polyethylene debris which lead to implant failure, osteolysis and metallosis. Also, ceramic inserts can be affected by higher internal frictional forces through cracking and fracture, leading to failure.

The Effects of Acetabular Shell Deformation and Liner Thickness on Frictional Torque in Ultrahigh-Molecular-Weight Polyethylene Acetabular Bearings, Gregg Schmidig, MBA, BS,* Amisha Patel, MS,* Imants Liepins, BE,* Mayur Thakore, M S,* and David C. Markel, MD.

Most common types of problems created by bonding stiffer isotropic metal implants with a composite anisotropic bone are the following:

Stiff femoral prosthesis may lead to excellent healing distally and stress shielding and bone resorption proximally, which leads to fracture and failure of the implant. Too much flexibility within the prosthesis leads to too much micromotion, poor bone ingrowth and aseptic loosening. Non-homogenous gradient implants may allow better and more fluid transfer of load from bone to prosthesis but are at risk for fracture at the cellular junctions. Short and narrow trunnion/head junctions preferred in less invasive surgery lead to micromotion, taper corrosion and metal debris. The medial aspect of the trunnion/head interface requires higher strength and stiffness than is currently provided by isotropic implants.

Acetabular shell deformation, caused by the pinching effect of the stiffer ischial and ilial columns of the host acetabular bone during press fit implantation, leads to higher frictional torques of the liners (inserts) used internally. Polyethylene, metal and ceramic inserts are therefore subjected to higher frictional forces which may lead to polyethylene and metal debris leading to osteolysis and metallosis, as well as damage and fracture to the ceramic heads.

An embodiment of the present invention may include a composite (metal and polymer) anisotropic implants which will exhibit asymmetrical stiffness properties based on the direction of applied load. A conventional acetabular cup is rotationally indifferent for installations within a prepared site; meaning the cup may be installed at any of 360 degrees rotation within the cavity. An embodiment of the present invention has a rotational directionality in that the implant is designed to be installed in a specific orientation within the prepared site. The implant site either has a native orientation specific stiffness characteristic (varies around a perimeter of the site) and/or is prepared with a desired rotational directionality. There may be just a single correct installation orientation for such an As an example, the medial border of the proximal femur known as calcar requires the ability to withstand high cyclic compressive loads and the lateral aspect of the proximal femur or the greater trochanter requires the ability to withstand tensile loads.

The production of a framework or reinforcement at least partially within a foundation (not exclusively on or within a surface layer) of the prosthesis. The foundation carries a bulk of the weight transferred to the implant. The framework can be accomplished through various different manufacturing techniques, including additive manufacturing. For example, the addition of a particular framework or pattern of metal, carbon, or glass fibers (reinforcement) within the foundation of the calcar may produce different material and/or mechanical properties of this particular section of the prosthesis.

This can be done by addition of tubes, sheets, slabs, walls, beams, columns, ribs, planks and other frames or frameworks within the foundation with any combination of arrangements to obtain the desired stiffness and strength mechanical properties for this section of the prosthesis. Similarly, a different pattern of framework can be produced on the lateral aspect of the femoral implant and pretensioned to counter the excessive tensive forces experienced on the lateral aspect of the prosthesis.

Figure 43:
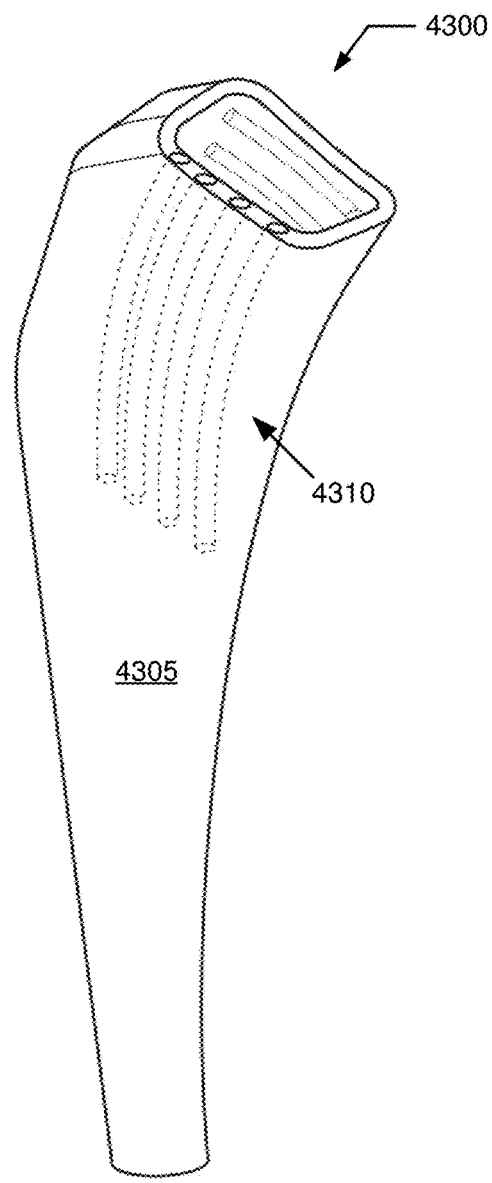
FIG. 43-FIG. 47 illustrate a set of prostheses, each including a body having a framework.
Figure 44:
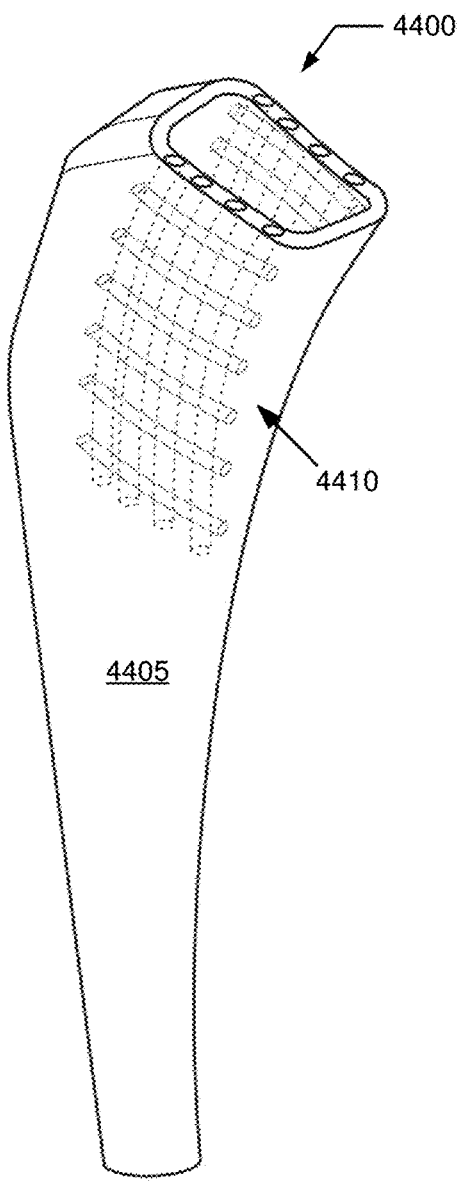
Figure 45:
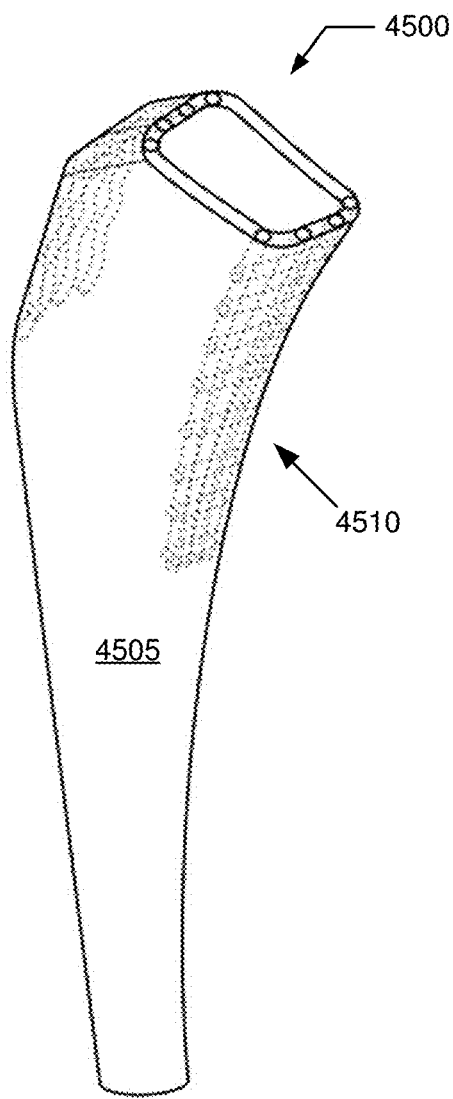
Figure 46:
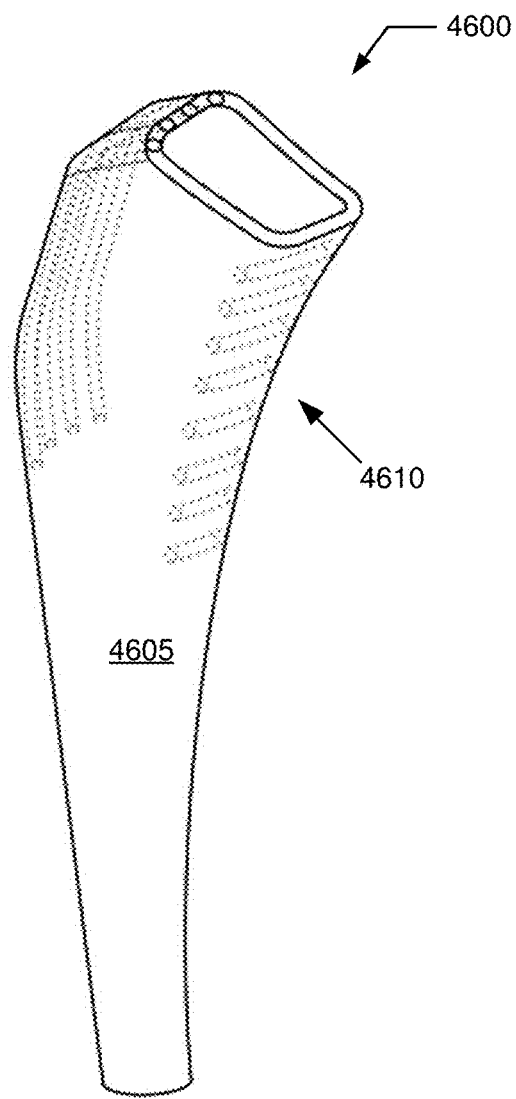
Figure 47:
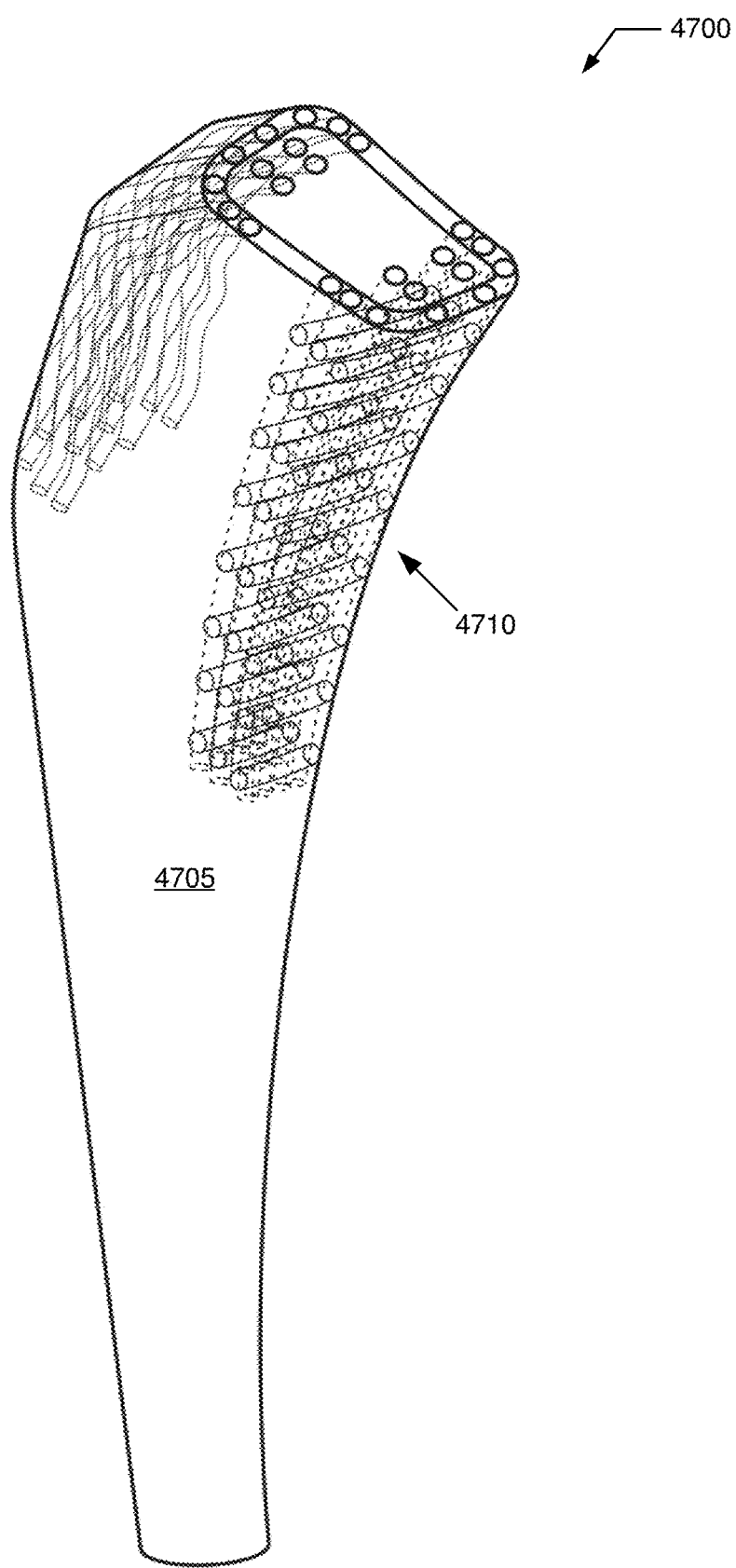
Figure 48:
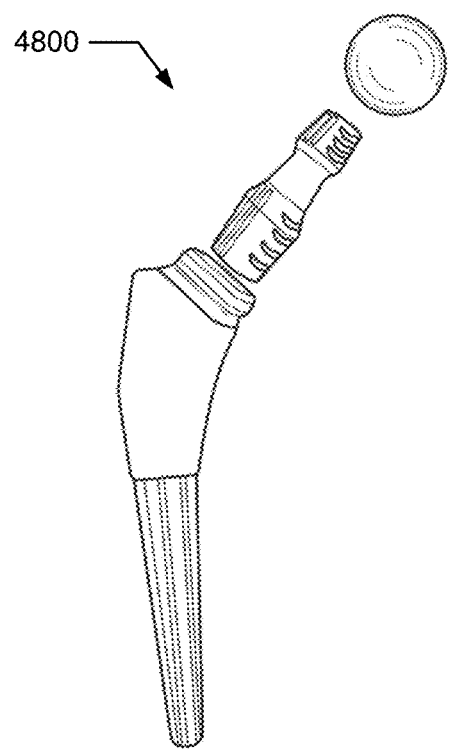
FIG. 48-FIG. 50 illustrate a set of modular prostheses, each set including a body, a head, and a neck, each neck including an anisotropic-defining framework producing a stiffness profile when assembled, the stiffness profiles different from each other.
Figure 49:
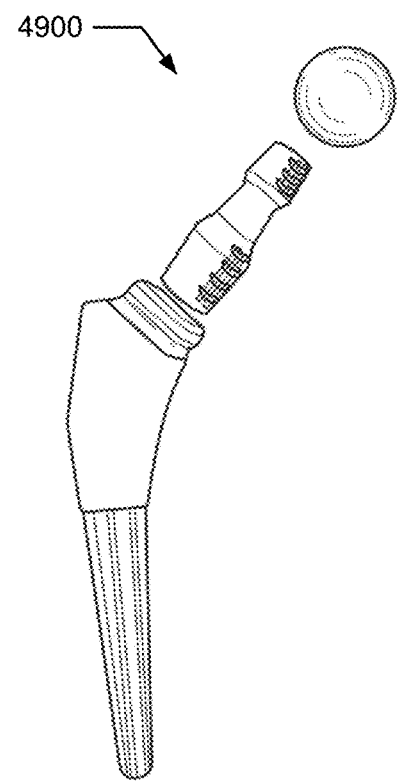
Figure 50:
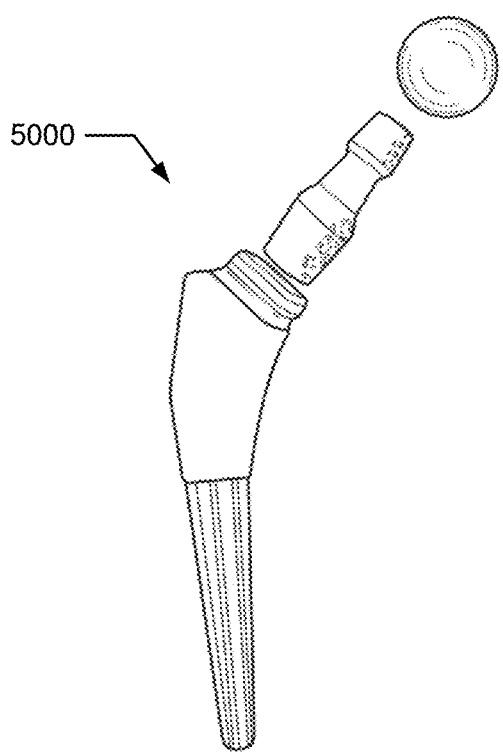
Figure 51:
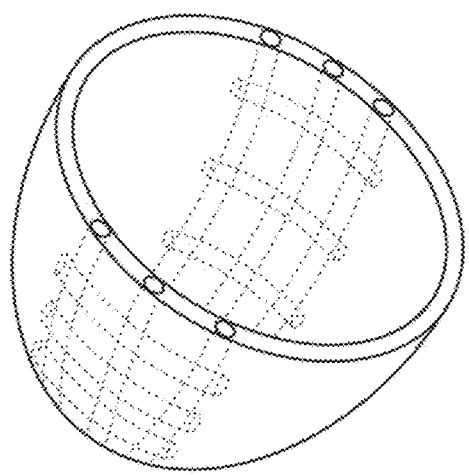
FIG. 51-FIG. 54 illustrate a set of implants, each implant including a body having an anisotropic-defining framework producing a stiffness profile when assembled, the stiffness profiles different from each other.
Figure 52:
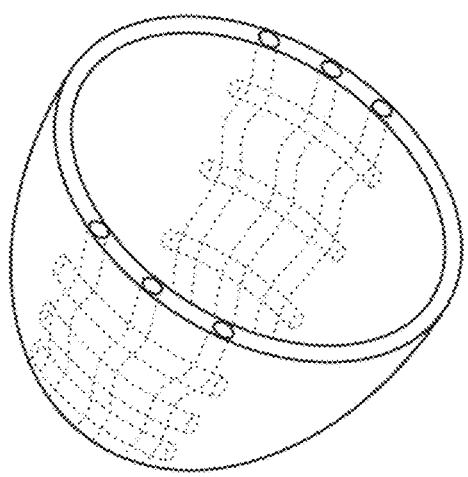
Figure 53:
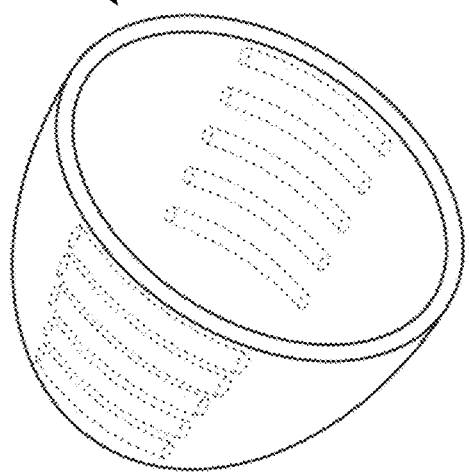
Figure 54:
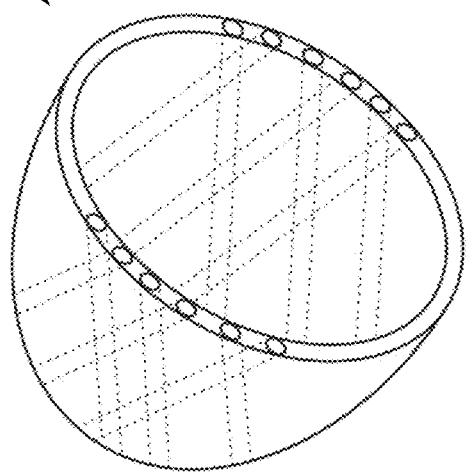

FIG. 43 illustrates a prosthesis including a femoral stem body having a first anisotropic-defining framework producing a desired stiffness profile;

FIG. 44 illustrates a prosthesis including a femoral stem body having a second anisotropic-defining framework producing a desired stiffness profile;

FIG. 45 illustrates a prosthesis including a femoral stem body having a third anisotropic-defining framework producing a desired stiffness profile;

FIG. 46 illustrates a prosthesis including a femoral stem body having a fourth anisotropic-defining framework producing a desired stiffness profile;

FIG. 47 illustrates a prosthesis including a femoral stem body having a fifth anisotropic-defining framework producing a desired stiffness profile;

FIG. 48-FIG. 50 illustrate a set of modular prostheses, each set including a body, a head, and a neck, each neck including an anisotropic-defining framework producing a stiffness profile when assembled, the stiffness profiles different from each other;

FIG. 48 illustrates a first modular prosthesis including a body, a head, and a neck, the neck including an anisotropic-defining framework producing a first stiffness profile when assembled;

FIG. 49 illustrates a second modular prosthesis including a body, a head, and a neck, the neck including an anisotropic-defining framework producing a second stiffness profile when assembled;

FIG. 50 illustrates a third modular prosthesis including a body, a head, and a neck, the neck including an anisotropic-defining framework producing a third stiffness profile when assembled;

FIG. 51-FIG. 54 illustrate a set of implants, each implant including a body having an anisotropic-defining framework producing a stiffness profile when assembled, the stiffness profiles different from each other;

FIG. 51 illustrates a first acetabular cup with a first anisotropic-defining framework producing a first stiffness profile for the cup;

FIG. 52 illustrates a second acetabular cup with a second anisotropic-defining framework producing a second stiffness profile for the cup;

FIG. 53 illustrates a third acetabular cup with a third anisotropic-defining framework producing a third stiffness profile for the cup; and FIG. 54 illustrates a fourth acetabular cup with a fourth anisotropic-defining framework producing a third stiffness profile for the cup.

FIG. 43-FIG. 47 illustrate a set of prostheses, each including a body having a framework. FIG. 43 illustrates a prosthesis 4300 including a femoral stem body 4305 having a first anisotropic-defining framework 4310 producing a desired stiffness profile. FIG. 44 illustrates a prosthesis 4400 including a femoral stem body 4405 having a second anisotropic-defining framework 4410 producing a desired stiffness profile. FIG. 45 illustrates a prosthesis 4500 including a femoral stem body 4505 having a third anisotropic-defining framework 4510 producing a desired stiffness profile. FIG. 46 illustrates a prosthesis 4600 including a femoral stem body 4605 having a third anisotropic-defining framework 4610 producing a desired stiffness profile. FIG. 47 illustrates a prosthesis 4700 including a femoral stem body 4705 having a third anisotropic-defining framework 4710 producing a desired stiffness profile.

These prostheses in FIG. 43-FIG. 47 differ in the incorporated framework within the femoral stem body. These frameworks include discrete structural elements in many different arrangements as illustrated in these figures. The framework elements may include one or more elements (parallel, matrix, woven elements) in different portions of the stem, different localized portions may include differently-oriented or same-oriented structural elements).

This concept also applies to creation of anisotropic head/trunnion interfaces where addition of tubes, sheets, slabs, walls, beams, columns, ribs, planks, crystalline structures, and other frames or frameworks within the foundation with any combination of arrangements to obtain the desired stiffness and strength mechanical properties for this section of the prosthesis, see FIG. 47. For example, the medial aspect of the trunnion can be made to be significantly more stiff and rigid than the lateral aspect of the trunnion with suggested modifications.

Similarly, this perimeter sensitive stiffness profile may be applied to other embodiments such as to anisotropic acetabular shells that can withstand the compression effects of the stiffer anterior and posterior columns without pinching and deforming the acetabular shell (See FIG. 51-FIG. 54).

Anisotropic implants, due to their ability to smoothly and fluidly transfer force between the environment, bone and prosthesis, have the potential for: (a) improved longevity over current isotropic implants (b) avoidance acute and chronic implant/bone bonding failures.

As discussed herein, bone is a naturally occurring hydroxyapatite-reinforced collagen composite structure whose behavior and response to applied load changes based on the direction of the applied load. The minerals calcium and phosphate and collagen constitute 60% to 70% of bone tissue. Collagen provides flexibility and ability to support tensile loads.

A composite material is made by combing two or more material. Often ones that have very different properties. The two material work together to give the composite unique properties. Natural composites exist in animals and plants. Wood is a composite. It is made of long cellulose fibers held together by much weaker substance lignin. Bone is another composite structure made from brittle material called hydroxyapatite (mainly calcium and phosphate) and soft flexible material collagen.

Humans have been using composites for thousands of years. One of the earliest examples are bricks which is a combination of mud and straw that give bricks both compressive and tensile strength.

Engineered composite structures in the industrial world are many including reinforced concrete, metal matrix composites, ceramic matrix composites, fibre-reinforced plastics.

A composite material is a material made from two or more constituent materials with significantly different physical or chemical properties, such that when combined, produce a material with different characteristics than the individual components. The new material may be preferred for many reasons, which may include material that is stronger, stiffer, lighter; or material that may have asymmetrical mechanical and anisotropic properties.

Composite material is used for spacecraft, aircraft, buildings, bridges, boats, hulls, swimming pools, cars, bikes, fishing rods, storage tanks etc.

Reinforced concrete is the most common example of composite materiel. Concrete is strong in compression, however, cannot survive tensile loads. Therefore, steel bars in different patterns are added to the foundation of concrete to give it the ability to withstand bending and tensile forces. Bone is similarly provides additional tensile strength by formation of certain tubular structures called osteon which are made of flexible collagen fibers.

Fiber reinforced polymers use similar concepts to incorporate fibre or fabric reinforcements in polymer resin as the matrix.

Composites can also use metal fibres reinforcing other metals, as in metal matrix composites (MMC), ceramic matrix composites (CMC), cermet (ceramic and metal). Wood is naturally occurring composite comprising of cellulise fibres in a lignin and hemicellulose matrix.

Composites are made of up individual materials referred to as constituent materials. There are two main categories of constituent materials: matrix (binder) and reinforcement. At least one portion of each type is required. The matrix material surrounds and supports the reinforcement materials by maintaining their relative positions. The reinforcements impart their special mechanical and physical properties to enhance the matrix properties. A synergism produces material properties unavailable from the individual constituent material, while the wide variety of matrix and reinforcement materials allows the design of product or structure to choose an optimum combination.

Typically, engineered composites material must be formed to shape. The matrix material can be introduced to the reinforcement material before or after the reinforcement material is placed in a mould cavity. The matrix material experiences a melding event, after which the part shape is set.

Inorganic matrices include concrete, metals, ceramics, glass. Organic matrices include polymers.

Reinforcements are typically fiber which include glass, carbon, high strength polymers (aramid-Kevlar), silicon carbide, fine fibers of pure carbon (graphite and carbon nanotubes), nanotubes of boron nitride. Woven and continuous fiber styles can be produced in a variety of forms.

Less commonly used forms of reinforcements include cores (honeycomb or foam), particles, and semi-crystalline polymers.

By choosing an appropriate combination of matrix and reinforcement material, a new material can be made that exactly meets the requirements of a particular application.

With the advent of additive manufacturing we believe metal-based implants which have so far been produced as isotropic implants can now be created as a composite structure, with anisotropic qualities, with a base metal as the matrix and various fiber frameworks as reinforcements, to produce generically customized implants for specific force, strength and stiffness requirements.

Non-metal implants such as fiber-reinforced care polymers can now be created as customized composite structure with a specific design parameter for specific anisotropic behavior.

The anisotropic implants can be produced with a single metallic material 3 D (three dimensional manufacturing— additive) printing or with multiple material 3 D printing.

With single material 3 D printing, as we have discussed before, the material properties of metal can be altered by adjusting density and porosity of crystalline metals. A metal alloy implant can be defined by a plurality of unit cells, which can be defined by their geometric properties and microstructure. The geometric properties of the unit cell can be manipulated to increase or decrease the density of a section of the implant. Any particular symmetrical or asymmetrical framework of higher and lower density metal can be 3 D printed within the structure and foundation of the prosthesis by alteration of the same metal. The framework may include any combination of patterns of tubes, sheets, slabs, walls, beams, columns, ribs, planks, helical structures and other frameworks (reinforcement structures) within the foundation of a particular implant. These reinforcements can have desired arrangements (including orthogonal and non-orthogonal cross sectional patterns) to obtain the desired stiffness and strength mechanical properties for a particular section of the prosthesis. Several embodiments of the concept are shown in figures A (proximal femur), B(acetabulum) C (trunnion), showing the alterations within the structural foundation of the metal prosthesis to enhance certain attributes of the implant.

Similar to single material 3D printing, we now have the capability of creating implants with multi-material 3 D printing. MultiFab: A Machine Vision Assisted Platform for Multi-material 3D Printing Pitchaya Sitthi-Amorn Javier E. Ramos Yuwang Wang Joyce Kwan Justin Lan Wenshou Wang Wojciech Matusik MIT CSAIL Chulalongkorn University Tsinghua University Additive manufacturing techniques continue to evolve and improve and processes exist to incorporate different materials such as glass, carbon, high strength polymers (aramid-Kevlar), silicon carbide, fine fibers of pure carbon (graphite and carbon nanotubes), nanotubes of boron nitride as reinforcement directly within or on an implant, including the structure and foundation of the prosthesis with 3D multi-material printing techniques. The variety of reinforcement material noted here produced in different geometric structures and directly embedded and additively printed within the foundation and structure of a Stainless steel, Titanium, Cobalt chrome and polymer implants as a matrix, provides for a vast variety of specialized implants with custom made areas of enhanced material and mechanical property, which can be produced for any specific need encountered in arthroplasty or trauma surgery.

The reinforcement frameworks within the structure of the prosthesis can produce asymmetrical stiffness and strength properties to the implant so as to produce an anisotropic implant that may for example resist compressive forces more effectively on its medial side and tensile forces more effectively on the lateral side of the femur. This would be a desirable configuration for a press fit femoral prosthesis. Similarly, an anisotropic acetabular shell would be able to resist compression more effectively about its anterior and posterior aspects (as compared to its inferior and superior aspects) since the pinching and compression of the acetabular shell which leads to shell deformation occurs through the more compact bones of the ischial and ilial columns.

Finally, the modular trunnion can have significantly stiffer portions medially than laterally due to specific design structures of a composite anisotropic prosthesis. For example carbon nanotubes fibers can be introduced as reinforcement within the base metal, via multi-material 3 D printing within the medial aspect of the trunnion, to enhance flexural rigidity. We note that with some of the designs of modular trunnions, a primary mode of failure was due increased flexibility, which led to increased micromotion, which ultimately lead to taper corrosion and trunnionosis. The ability to alter the flexural rigidity of the medial aspect of the trunnion to a desired effect may make this type of modular prosthesis viable again.

The system and methods above have been described in general terms as an aid to understanding details of preferred embodiments of the present invention. In the description herein, numerous specific details are provided, such as examples of components and/or methods, to provide a thorough understanding of embodiments of the present invention. Some features and benefits of the present invention are realized in such modes and are not required in every case. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as inoperable in certain cases, as is useful in accordance with a particular application.

Additionally, any signal arrows in the drawings/Figures should be considered only as exemplary, and not limiting, unless otherwise specifically noted. Combinations of components or steps will also be considered as being noted, where terminology is foreseen as rendering the ability to separate or combine is unclear.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. A structural medical device configured for installation into a prepared cavity, comprising:
    a body including a body portion sized for a pressfit fixation into the prepared cavity;
    a framework disposed within said body portion;
    wherein said framework includes a set of one or more structural elements configured to produce an anisotropic bulk material property in said body portion.

2. The device of claim 1 wherein the prepared cavity includes an area of an acetabulum and wherein said body includes an acetabular cup.

3. The device of claim 2 wherein said body portion includes a foundation layer of said acetabular cup.

4. The device of claim 2 wherein said framework includes a first set of one or more structural elements and a second set of one or more structural elements, each set of structural elements disposed in different non-overlapping regions of said acetabular cup.

5. The device of claim 4 wherein said first set of structural elements is different than said second set of structural elements.

6. The device of claim 4 wherein said body portion includes a surface, wherein said first set of structural elements are disposed beneath said surface, and wherein said second set of structural elements are disposed on said surface.

7. The device of claim 6 wherein said second set of structural elements includes at least a subset of structural elements selectively dissolvable within the prepared cavity and wherein a dissolution of said subset of structural elements is configured to alter said anisotropic bulk material property.

8. The device of claim 1 wherein said framework includes a first set of one or more structural elements and a second set of one or more structural elements, each set of structural elements disposed in different non-overlapping regions of said body portion.

9. The device of claim 8 wherein said first set of structural elements is different than said second set of structural elements.

10. The device of claim 8 wherein said body portion includes a surface, wherein said first set of structural elements are disposed beneath said surface, and wherein said second set of structural elements are disposed on said surface.

11. The device of claim 10 wherein said second set of structural elements includes at least a subset of structural elements selectively dissolvable within the prepared cavity and wherein a dissolution of said subset of structural elements is configured to alter said anisotropic bulk material property.

12. The device of claim 1 wherein the prepared cavity includes a channel prepared in a long bone and wherein said body includes a stem.

13. The device of claim 12 wherein said body portion includes a foundation layer of said stem.

14. The device of claim 12 wherein said framework includes a first set of one or more structural elements and a second set of one or more structural elements, each set of structural elements disposed in different non-overlapping regions of said stem.

15. The device of claim 14 wherein said first set of structural elements is different than said second set of structural elements.

16. The device of claim 12 wherein said body portion includes a surface, wherein said first set of structural elements are disposed beneath said surface, and wherein said second set of structural elements are disposed on said surface.

17. The device of claim 16 wherein said second set of structural elements includes at least a subset of structural elements selectively dissolvable within the prepared cavity and wherein a dissolution of said subset of structural elements is configured to alter said anisotropic bulk material property.

18. A modular structural medical device configured for installation into a prepared cavity, comprising:
a body including a body portion sized for a pressfit fixation into the prepared cavity, said body further including a neck socket;
a neck configured for a pressfit fixation engagement with said neck socket, said neck including a trunnion portion;
a head configured for a pressfit fixation engagement with said trunnion portion;
and
a framework disposed within said neck;
wherein said framework includes a set of one or more structural elements configured to produce an anisotropic bulk material property in said neck.

* * * * *